US012567144B2

(12) United States Patent
Sakamoto et al.

(10) Patent No.: US 12,567,144 B2
(45) Date of Patent: Mar. 3, 2026

(54) INFORMATION PROCESSING DEVICE, INFORMATION PROCESSING METHOD, AND PROGRAM

(71) Applicant: TERUMO KABUSHIKI KAISHA, Tokyo (JP)

(72) Inventors: Yasukazu Sakamoto, Ashigarakami-gun Kanagawa (JP); Katsuhiko Shimizu, Ashigarakami-gun Kanagawa (JP); Hiroyuki Ishihara, Kanagawa (JP); Shunsuke Yoshizawa, Kanagawa (JP); Thomas Henn, Sakai (JP); Clément Jacquet, Sakai (JP); Stephen Tchen, Sakai (JP); Ryosuke Saga, Sakai (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 365 days.

(21) Appl. No.: 18/190,257

(22) Filed: Mar. 27, 2023

(65) Prior Publication Data

US 2023/0260120 A1    Aug. 17, 2023

Related U.S. Application Data

(63) Continuation of application No. PCT/JP2021/035671, filed on Sep. 28, 2021.

(30) Foreign Application Priority Data

Sep. 29, 2020    (JP) ................................. 2020-163912

(51) Int. Cl.
G06T 7/00          (2017.01)
G06V 10/25        (2022.01)
(Continued)

(52) U.S. Cl.
CPC ............ *G06T 7/0012* (2013.01); *G06V 10/25* (2022.01); *G06V 10/764* (2022.01); *G16H 30/20* (2018.01); *G06T 2207/30021* (2013.01)

(58) Field of Classification Search
CPC .... A61B 2017/00243; A61B 2090/367; A61B 2090/3735; A61B 2090/376;
(Continued)

(56) References Cited

U.S. PATENT DOCUMENTS

2005/0249391 A1* 11/2005 Kimmel ................. G06T 7/143
                                                              382/128
2007/0165916 A1    7/2007 Cloutier et al.
(Continued)

FOREIGN PATENT DOCUMENTS

CN          102056547 A      5/2011
CN          104321007 A      1/2015
(Continued)

OTHER PUBLICATIONS

Extended European Search Report dated Jan. 29, 2024, issued in corresponding European Application No. 21875629.4. (9 pages).
(Continued)

*Primary Examiner* — Manuchehr Rahmjoo
(74) *Attorney, Agent, or Firm* — Buchanan Ingersoll & Rooney PC

(57) ABSTRACT

An information processing device that assists understanding of an image acquired by an image acquisition catheter. The information processing device includes: an image acquisition unit that acquires a catheter image including an inner cavity obtained by an image acquisition catheter; a position information acquisition unit that acquires position information regarding a position of a medical instrument inserted into the inner cavity included in the catheter image; and a first data output unit that inputs the acquired catheter image (Continued)

and the acquired position information to a first trained model that, upon receiving input of the catheter image and the position information, outputs first data in which each region of the catheter image is classified into at least three of a biological tissue region, a medical instrument region where the medical instrument exists, and a non-biological tissue region, and outputs the first data.

20 Claims, 34 Drawing Sheets

(51) Int. Cl.
*G06V 10/764* (2022.01)
*G16H 30/20* (2018.01)

(58) Field of Classification Search
CPC .......... A61B 2090/3782; A61B 5/0066; A61B 5/0084; A61B 6/12; A61B 8/0841; A61B 8/0883; A61B 8/0891; A61B 8/12; A61B 8/4461; A61B 8/483; A61B 8/5215; A61B 90/37; G06N 3/0442; G06N 3/0455; G06N 3/0464; G06N 3/0475; G06N 3/09; G06T 2207/30021; G06T 7/0012; G06V 10/25; G06V 10/764; G16H 30/20
See application file for complete search history.

(56) References Cited

U.S. PATENT DOCUMENTS

| | | | |
|---|---|---|---|
| 2011/0071404 A1 | 3/2011 | Schmitt et al. | |
| 2011/0082371 A1 | 4/2011 | Chono | |
| 2012/0075638 A1 | 3/2012 | Rollins et al. | |
| 2014/0100449 A1 | 4/2014 | Begin et al. | |
| 2014/0253685 A1 | 9/2014 | Akimoto et al. | |
| 2014/0350401 A1* | 11/2014 | Sinelnikov | A61B 18/1492 |
| | | | 606/169 |
| 2015/0182192 A1 | 7/2015 | Kaneko | |
| 2017/0193658 A1 | 7/2017 | Cardinal et al. | |
| 2019/0021694 A1 | 1/2019 | Sakaguchi | |
| 2020/0093543 A1 | 3/2020 | Takahashi et al. | |
| 2021/0090249 A1* | 3/2021 | Choi | A61B 8/461 |
| 2021/0137634 A1* | 5/2021 | Lang | A61B 90/00 |
| 2022/0347446 A1* | 11/2022 | Fahey | A61B 17/0057 |

FOREIGN PATENT DOCUMENTS

| | | | |
|---|---|---|---|
| CN | 110662491 A | 1/2020 | |
| JP | 2007512862 A | 5/2007 | |
| JP | 2013505782 A | 2/2013 | |
| JP | 2015532860 A | 11/2015 | |
| JP | 2019503833 A | 2/2019 | |
| JP | 6632020 B1 | 1/2020 | |
| WO | 2014041579 A1 | 3/2014 | |
| WO | 2017164071 A1 | 9/2017 | |
| WO | 2019135501 A1 | 7/2019 | |
| WO | 2020165389 A1 | 8/2020 | |

OTHER PUBLICATIONS

Villacastin et a., "Learning Process for Transseptal Puncture Guided by Intracardiac Echocardiography", Revista Espanola De Cardiologia, (English Edition) Elsevier, Amsterdam, NL, Apr. 1, 2004, vol. 57, No. 4, pp. 359-362, XP005642952.

International Search Report (PCT/ISA/210) with translation and Written Opinion (PCT/ISA/237) mailed on Dec. 28, 2021, by the Japanese Patent Office as the International Searching Authority for International Application No. PCT/JP2021/035671. (10 pages).

The First Office Action issued on Apr. 20, 2025, by the State Intellectual Property Office of the People's Republic of China in corresponding Chinese Patent Application No. 202180066292.7 and an English translation of the Action. (17 pages).

* cited by examiner

Catheter image

518

Medical instrument trained model

611

First position information

Catheter image

518

Classification model

62

Classification data

528

71

| Catheter image | Position information |
|---|---|
| img001 | p001 |
| img002 | p002 |
| img003 | p003 |
| img004 | p004 |
| img005 | p005 |

RT format                         XY format

612

Catheter image                              Scanning angle
                                                information

Fig. 19

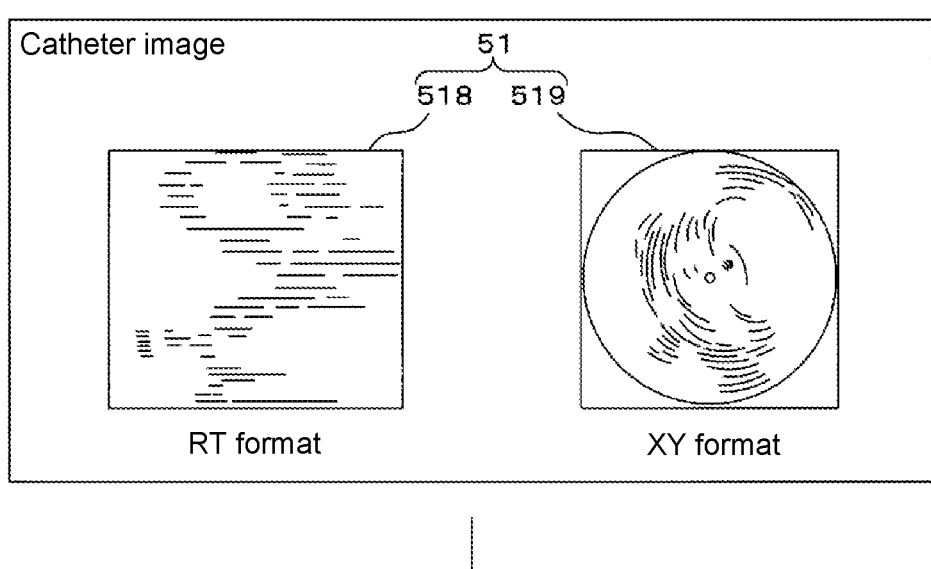

Catheter image    51

518    519

RT format    XY format

- Boundary line between first inner cavity region and biological tissue region
- Boundary line between second inner cavity region and biological tissue region
- Boundary line between non-inner cavity region and biological tissue region
- Visible outline of the medical instrument region

521

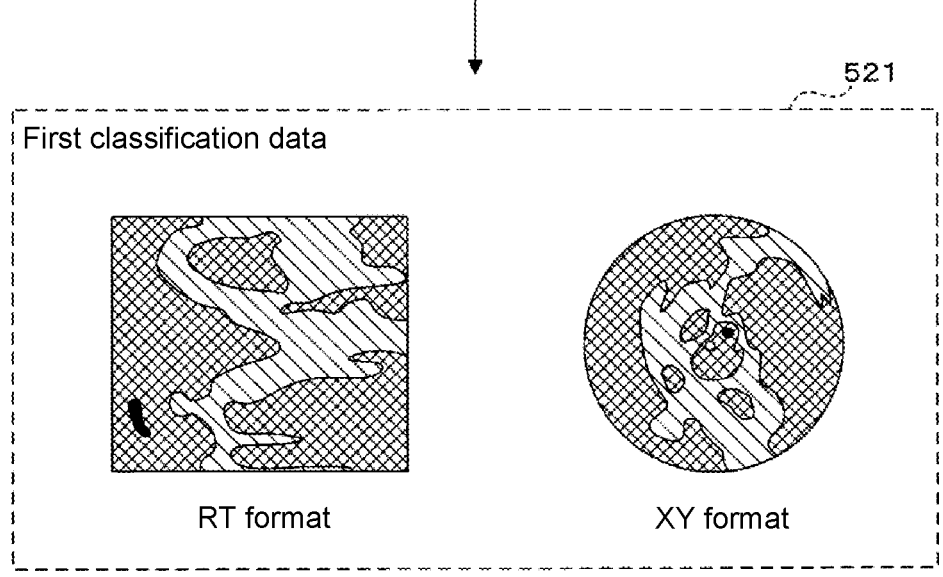

First classification data

RT format    XY format

Fig. 22
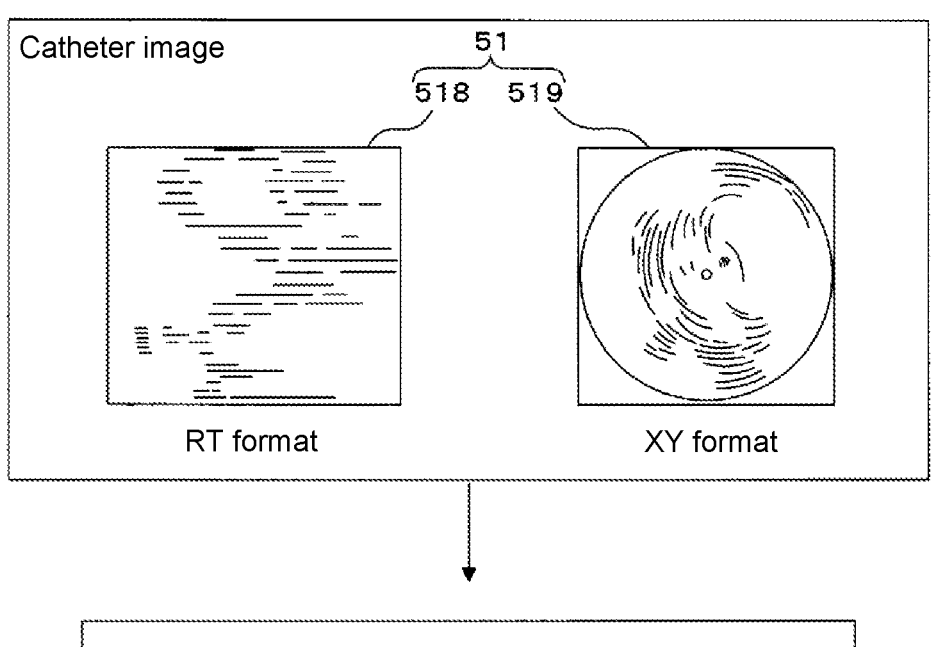
Catheter image    51
518    519
RT format    XY format
• Boundary between first inner cavity region and biological region
• Visible outline of the medical instrument region
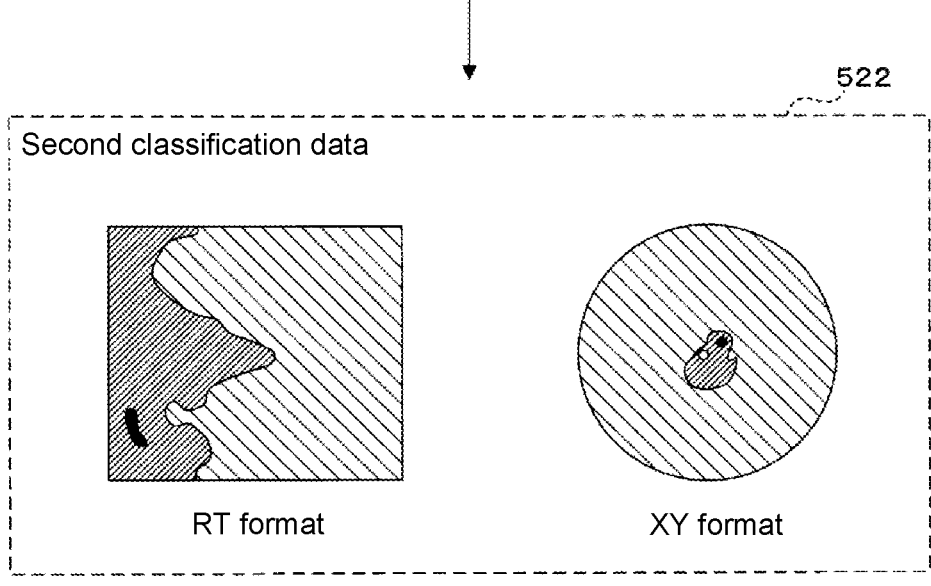
522
Second classification data
RT format    XY format

| Catheter image | Position information | Classification data |
|---|---|---|
| RT101 | r1, $\theta$1 | LRT101 |
| RT102 | r2, $\theta$2 | LRT102 |
| RT103 | r3, $\theta$3 | LRT103 |
| RT104 | r4, $\theta$4 | LRT104 |
| | . | |
| | . | |
| | . | |
| | . | |
| | . | |
| | . | |

INFORMATION PROCESSING DEVICE, INFORMATION PROCESSING METHOD, AND PROGRAM

CROSS-REFERENCES TO RELATED APPLICATIONS

This application is a continuation of International Application PCT/JP2021/035671 filed on Sep. 28, 2021, which claims priority to Japanese Application No. 2020-163912 filed on Sep. 29, 2020, the entire content of both of which is incorporated herein by reference.

TECHNOLOGICAL FIELD

The present disclosure generally relates to an information processing device, an information processing method, and a program.

BACKGROUND DISCUSSION

A catheter system that acquires an image by inserting an image acquisition catheter into a hollow organ such as a blood vessel is used (WO 2017/164071 A).

For example, in a place of a complicated structure such as an intracardiac region, it may be difficult to quickly understand an image acquired by an image acquisition catheter.

SUMMARY

An information processing device, an information processing method, and a non-transitory computer-readable medium are disclosed that assist in understanding of an image acquired by an image acquisition catheter.

An information processing device includes: an image acquisition unit that acquires a catheter image including an inner cavity obtained by an image acquisition catheter; a position information acquisition unit that acquires position information regarding a position of a medical instrument inserted into the inner cavity included in the catheter image; and a first data output unit that inputs the acquired catheter image and the acquired position information to a first trained model that, upon receiving input of the catheter image and the position information, outputs first data in which each region of the catheter image is classified into at least three of a biological tissue region, a medical instrument region where the medical instrument exists, and a non-biological tissue region, and outputs the first data.

In one aspect, it is possible to provide an information processing device and the like that assist in understanding of an image acquired by an image acquisition catheter.

BRIEF DESCRIPTION OF THE DRAWINGS

FIG. 19 is an explanatory view explaining first training data.

FIG. 22 is an explanatory view explaining second training data.

3

4

Figure 34:
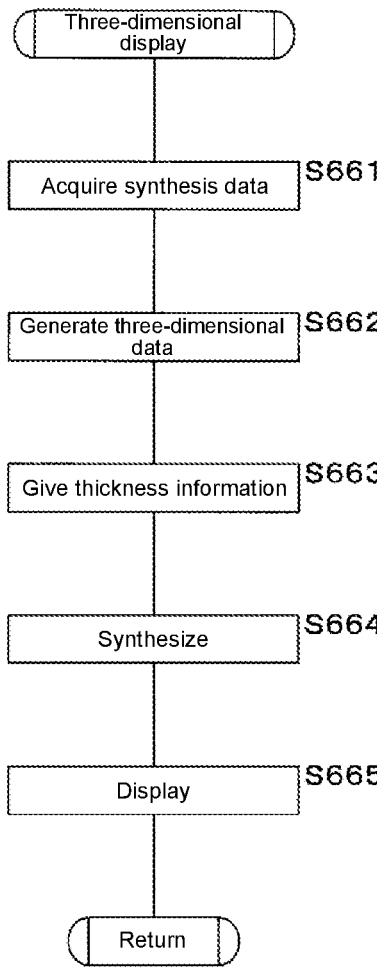

FIG. 34 is a flowchart explaining a flow of processing of a subroutine of three-dimensional display.

Figure 35:
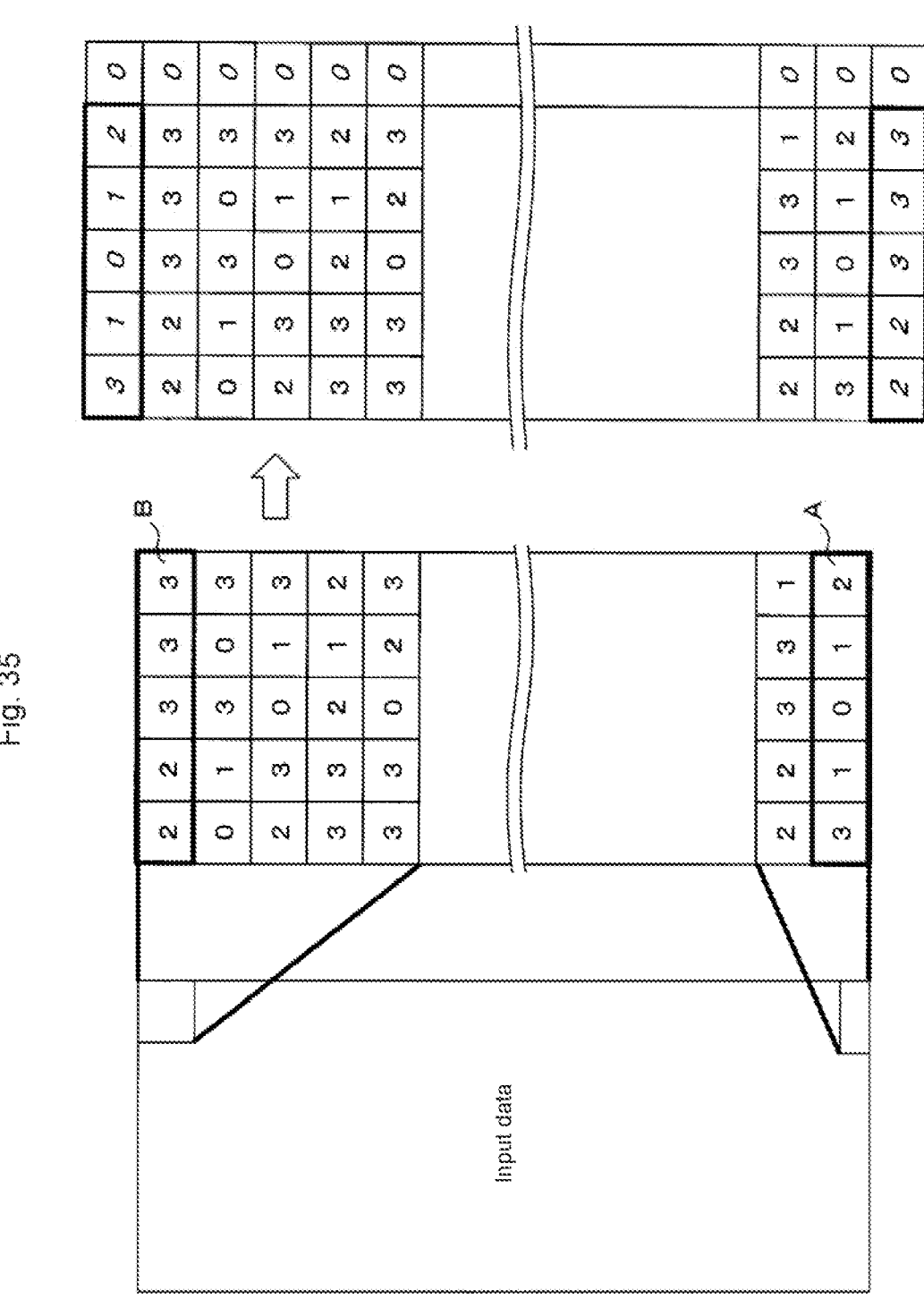

FIG. 35 is an explanatory view explaining padding processing of a ninth embodiment.

Figure 36:
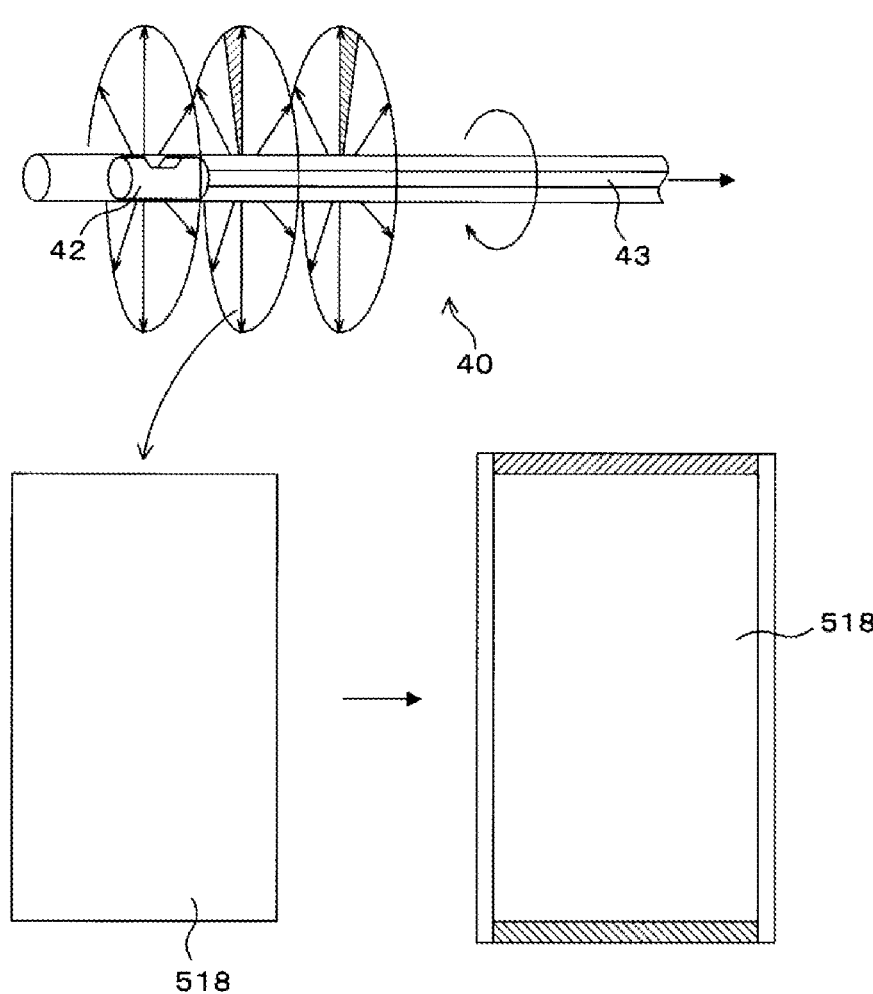

FIG. 36 is an explanatory view explaining polar padding processing of the modification.

Figure 37:
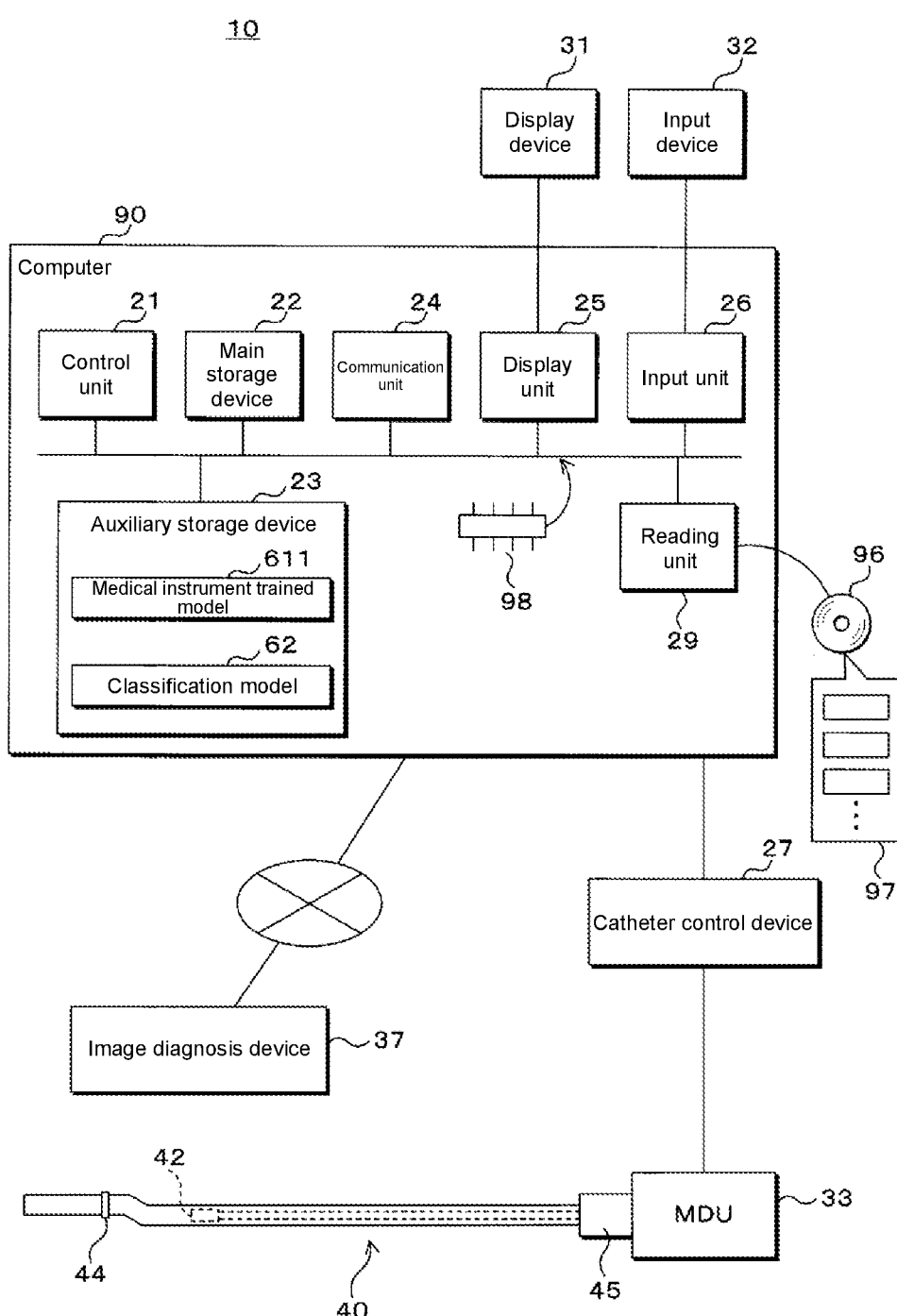

FIG. 37 is an explanatory view explaining a configuration of a catheter system of a tenth embodiment.

Figure 38:
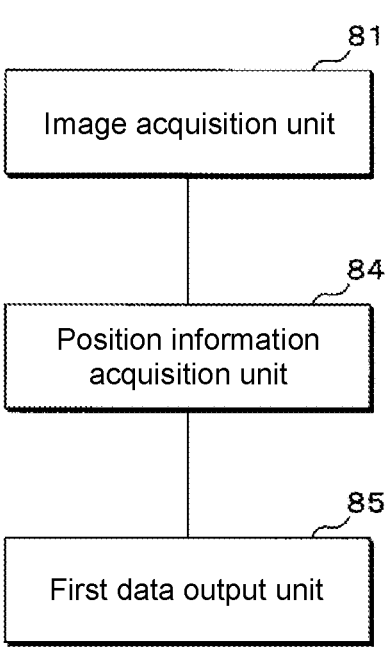

FIG. 38 is a functional block diagram of an information processing device according to an eleventh embodiment.

DETAILED DESCRIPTION

Set forth below with reference to the accompanying drawings is a detailed description of embodiments of an information processing device, an information processing method, and a program.

First Embodiment

Figure 1:
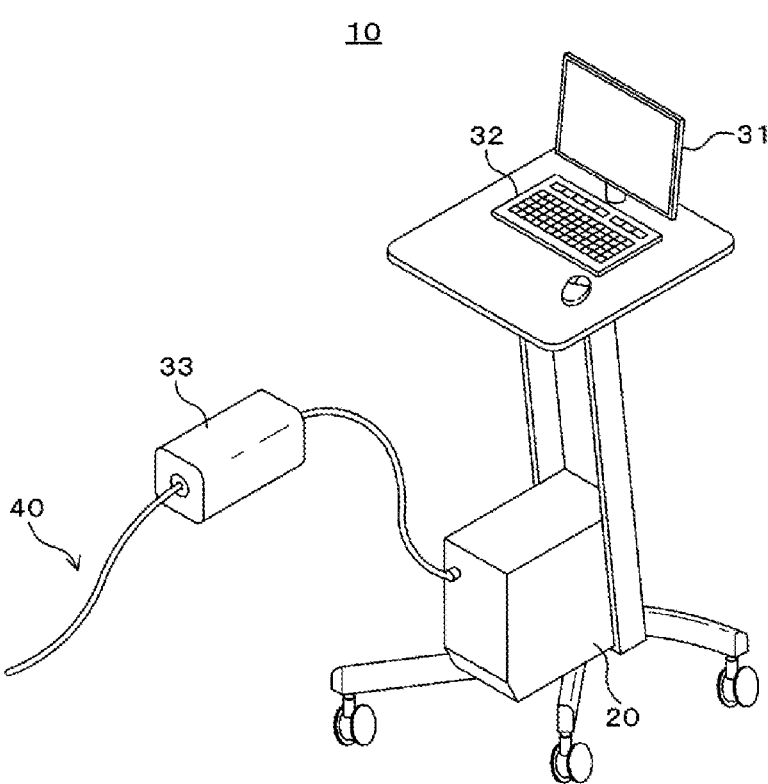
FIG. 1 is an explanatory view explaining an outline of a catheter system.

FIG. 1 is an explanatory view explaining an outline of a catheter system 10. The catheter system 10 of the present embodiment can be used for interventional radiology (IVR) that performs treatment of various organs while performing fluoroscopy using an image diagnosis device such as an X-ray fluoroscopic device. By referring to an image acquired by the catheter system 10 disposed in the vicinity of a treatment target site, the medical instrument for treatment can be accurately operated.

The catheter system 10 includes an image acquisition catheter 40, a motor driving unit (MDU) 33, and an information processing device 20. The image acquisition catheter 40 is connected to the information processing device 20 via the MDU 33. A display device 31 and an input device 32 are connected to the information processing device 20. The input device 32 is an input device such as a keyboard, a mouse, a trackball, or a microphone. The display device 31 and the input device 32 may be integrally laminated to constitute a touchscreen. The input device 32 and the information processing device 20 may be integrally configured (i.e., combined into a single unit).

Figure 2:
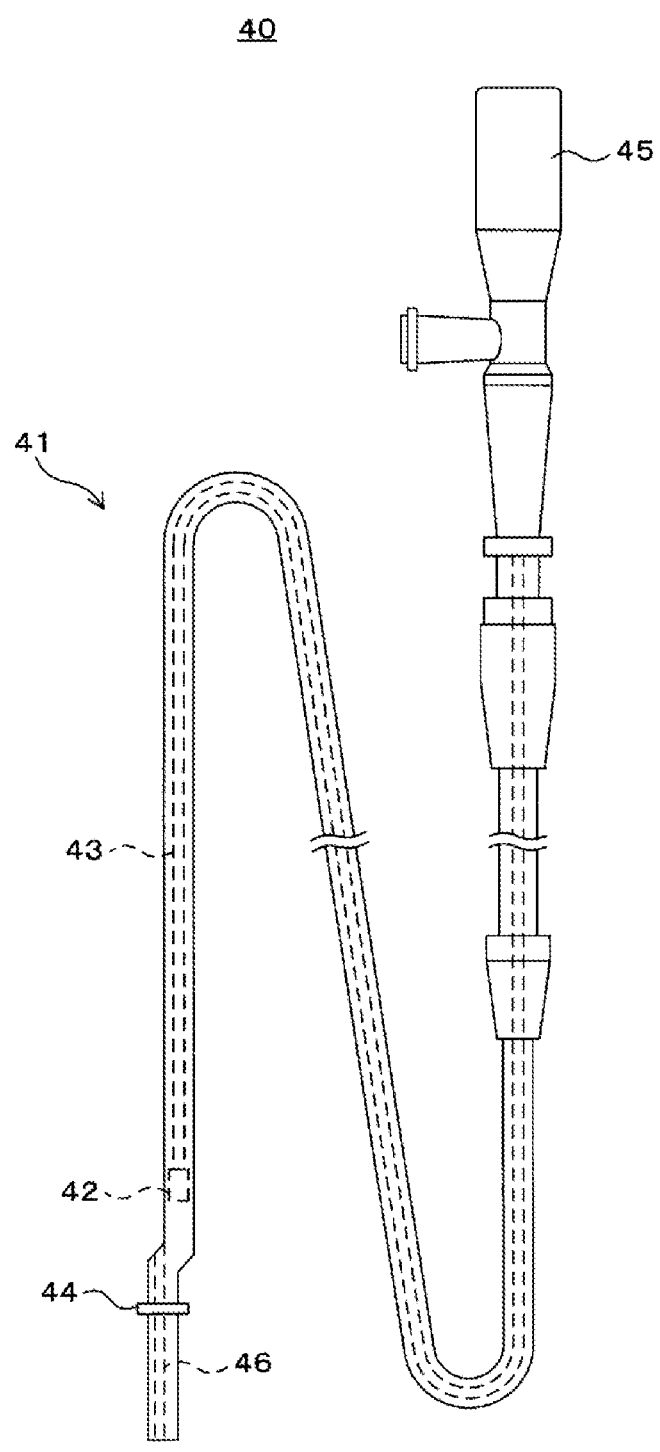
FIG. 2 is an explanatory view explaining an outline of an image acquisition catheter.

FIG. 2 is an explanatory view explaining an outline of an image acquisition catheter 40. The image acquisition catheter 40 includes a probe portion 41 and a connector portion 45 disposed at an end part of the probe portion 41. The probe portion 41 is connected to the MDU 33 via the connector portion 45. In the following description, a side far from the connector portion 45 of the image acquisition catheter 40 will be referred to as distal side.

A shaft 43 is inserted into the probe portion 41. A sensor 42 is connected to the distal side of the shaft 43. A guide wire lumen 46 is provided at the distal end of the probe portion 41. By inserting a guide wire to a position beyond the target site before inserting the guide wire into the guide wire lumen 46, the user can guide the sensor 42 to the target site. An annular distal marker 44 can be fixed in the vicinity of the distal part of the probe portion 41.

The sensor 42 can be, for example, an ultrasound transducer that transmits and receives ultrasound waves, or a transmission and reception unit for optical coherence tomography (OCT) that emits near-infrared light and receives reflected light. In the following description, a case where the image acquisition catheter 40 is an intravascular ultrasound (IVUS) catheter used when an ultrasound tomographic image is captured from the inside of a circulatory organ will be described as an example.

Figure 3:
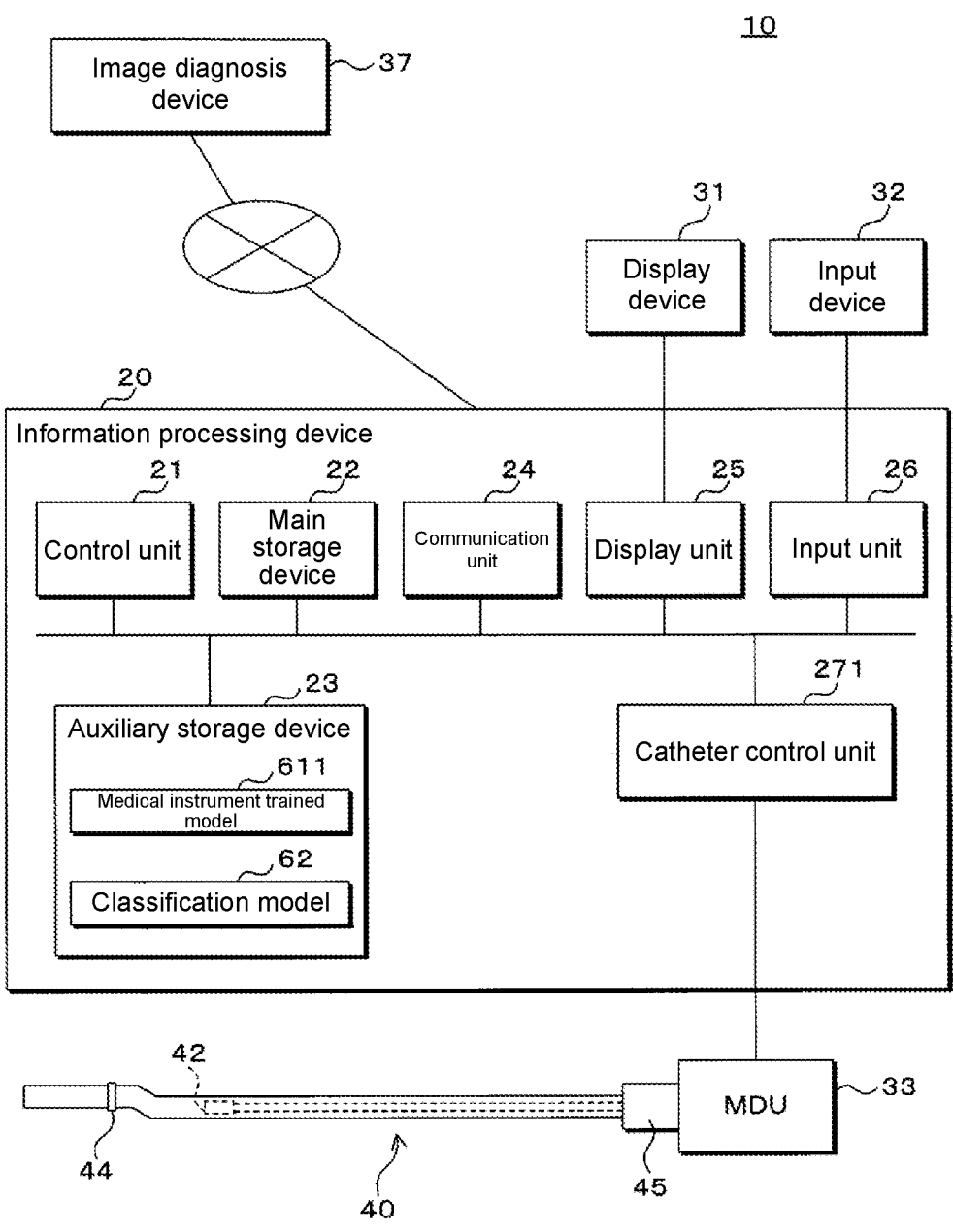
FIG. 3 is an explanatory view explaining a configuration of the catheter system.

FIG. 3 is an explanatory view explaining the configuration of the catheter system 10. As described above, the catheter system 10 includes the information processing device 20, the MDU 33, and the image acquisition catheter 40. The information processing device 20 includes a control unit 21, a main storage device 22, an auxiliary storage device 23, a communication unit 24, a display unit 25, an input unit 26, a catheter control unit 271, and a bus.

The control unit 21 can be an arithmetic control device that executes the program of the present embodiment. For the control unit 21, one or a plurality of central processing units (CPUs), graphics processing units (GPUs), tensor processing units (TPUs), multi-core CPUs, or the like can be used. The control unit 21 is connected to each hardware unit constituting the information processing device 20 via the bus.

The main storage device 22 is a storage device such as a static random access memory (SRAM), a dynamic random access memory (DRAM), or a flash memory. The main storage device 22 temporarily saves necessary information in the middle of processing performed by the control unit 21 and a program being executed by the control unit 21.

The auxiliary storage device 23 can be a storage device such as an SRAM, a flash memory, a hard disk, or a magnetic tape. The auxiliary storage device 23 saves a medical instrument trained model 611, a classification model 62, a program to be executed by the control unit 21, and various data necessary for executing the program. The communication unit 24 is an interface that performs communication between the information processing device 20 and a network.

The display unit 25 is an interface that connects the display device 31 and the bus. The input unit 26 is an interface that connects the input device 32 and the bus. The catheter control unit 271 performs control of the MDU 33, control of the sensor 42, generation of an image based on a signal received from the sensor 42, and the like.

The MDU 33 rotates the sensor 42 and the shaft 43 inside the probe portion 41. The catheter control unit 271 generates one catheter image 51 (see FIG. 4) for each rotation of the sensor 42. The generated catheter image 51 is a transverse tomographic image centered on the probe portion 41 and substantially perpendicular to the probe portion 41.

The MDU 33 can further advance and retract the sensor 42 while rotating the sensor 42 and the shaft 43 inside the probe portion 41. By an operation of rotating the sensor 42 while pulling or pushing the sensor 42, the catheter control unit 271 continuously generates a plurality of catheter images 51 substantially perpendicular to the probe portion 41. The continuously generated catheter images 51 can be used to construct a three-dimensional image. Therefore, the image acquisition catheter 40 implements the function of a three-dimensional scanning catheter that sequentially acquires the plurality of catheter images 51 along a longitudinal direction.

The advancing and retracting operation of the sensor 42 includes both an operation of advancing and retracting the entire probe portion 41 and an operation of advancing and retracting the sensor 42 inside the probe portion 41. The advancing and retracting operation may be automatically performed at a predetermined speed by the MDU 33 or may be manually performed by the user.

The image acquisition catheter 40 is not limited to a mechanical scanning method of mechanically performing rotation and advancing and retracting. The image acquisition catheter 40 may be an electronic radial scanning type using the sensor 42 in which a plurality of ultrasound transducers are annularly arranged.

Using the image acquisition catheter 40, it is possible to capture the catheter image 51 including a reflector present inside a circulatory organ such as red blood cells and an organ present outside the circulatory organ such as a respiratory organ and a digestive organ in addition to a biological tissue constituting the circulatory organ such as a heart wall and a blood vessel wall.

In the present embodiment, a case where the image acquisition catheter 40 is used for atrial septal puncture will be described as an example. In the atrial septal puncture, after the image acquisition catheter 40 is inserted into the right atrium, a Brockenbrough needle is punctured into the fossa ovalis, which is a thin portion of the atrial septal, under ultrasound guide. The distal end of the Brockenbrough needle reaches the inside of the left atrium.

In a case of performing atrial septal puncture, the catheter image 51 visualizes the Brockenbrough needle in addition to a biological tissue constituting a circulatory organ such as the atrial septal, the right atrium, the left atrium, and the aorta, and a reflector such as red blood cells contained in blood flowing inside the circulatory organ. A user such as a medical doctor can safely perform atrial septal puncture by confirming the positional relationship between the fossa ovalis and the distal end of the Brockenbrough needle using the catheter image 51. The Brockenbrough needle is an example of the medical instrument of the present embodiment.

The use of the catheter system 10 is not limited to the atrial septal puncture. For example, the catheter system 10 can be used for manipulations such as transcatheter myocardial ablation, transcatheter valve replacement, and stent placement in a coronary artery or the like. The site to be treated using the catheter system 10 is not limited to the periphery of the heart. For example, the catheter system 10 can be used for treatment of various sites such as a pancreatic duct, a bile duct, and a lower extremity vessel.

Since the function and configuration of the catheter control unit 271 are similar to those of a conventionally used ultrasound diagnosis device, the detailed description of catheter control unit 271 will be omitted. The control unit 21 may implement the function of the catheter control unit 271.

The information processing device 20 is connected to various image diagnosis devices 37 such as an X-ray angiography device, an X-ray computed tomography (CT) device, a magnetic resonance imaging (MRI) device, a positron emission tomography (PET) device, or an ultrasound diagnosis device via a hospital information system (HIS) or the like.

The information processing device 20 of the present embodiment, can be, for example, a dedicated ultrasound diagnosis device, or a personal computer, a tablet, a smartphone, or the like having the function of an ultrasound diagnosis device. In the following description, a case where the information processing device 20 is also used for learning of a trained model such as the medical instrument trained model 611 and creation of training data will be described as an example. A computer, a server, or the like different from the information processing device 20 may be used for learning of the trained model and creation of the training data.

In the following description, a case where mainly the control unit 21 performs software processing will be described as an example. The processing described using the flowchart and the various trained models may be implemented by dedicated hardware.

Figure 4:
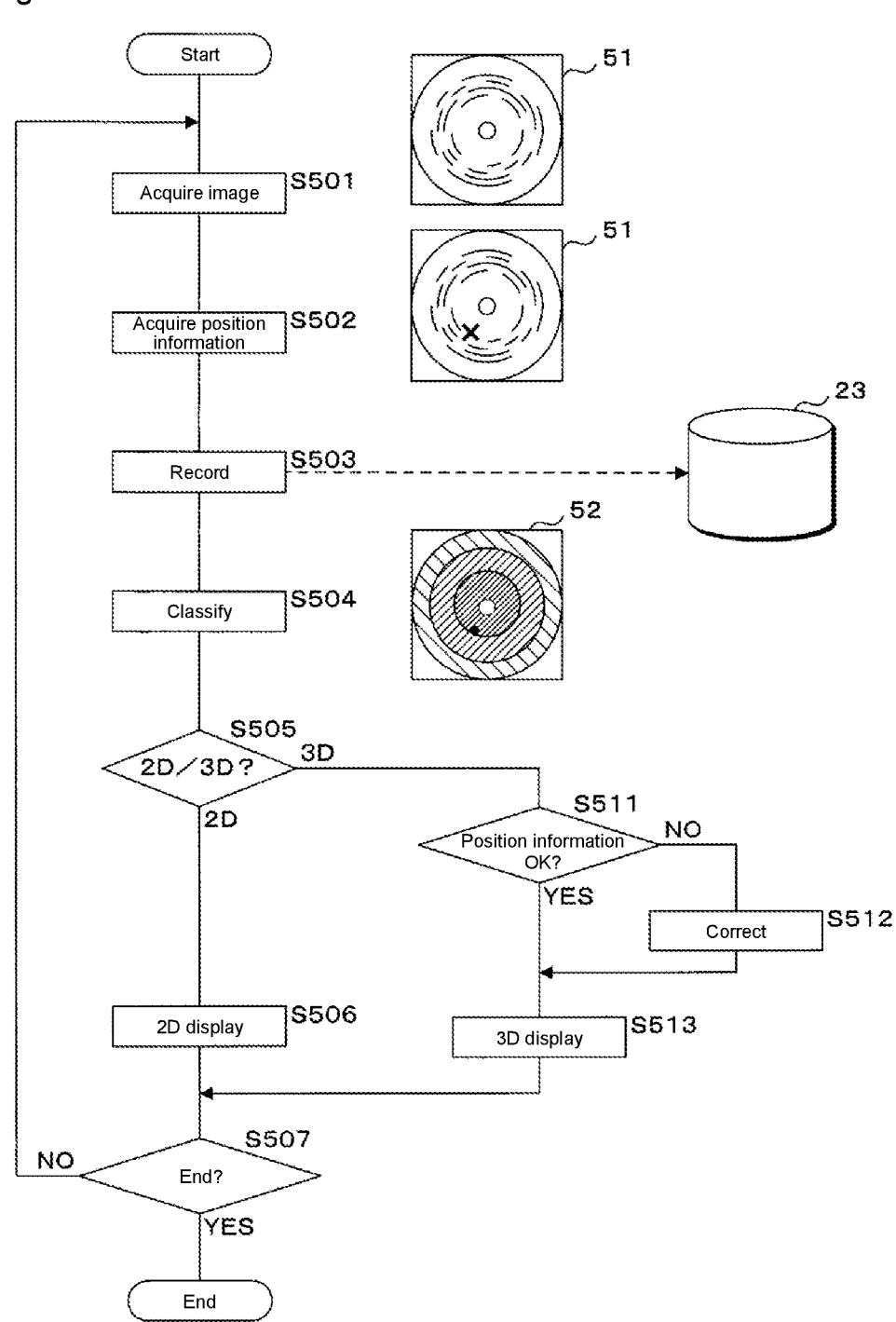
FIG. 4 is an explanatory view explaining an outline of an operation of the catheter system.

FIG. 4 is an explanatory view explaining an outline of the operation of the catheter system 10. In FIG. 4, a case of capturing a plurality of catheter images 51 while pulling the sensor 42 at a predetermined speed and displaying an image in real time will be described as an example.

The control unit 21 captures one catheter image 51 (S501). The control unit 21 acquires position information of the medical instrument visualized in the catheter image 51 (S502). In FIG. 4, the position of the medical instrument in the catheter image 51 is indicated by a cross mark (x).

The control unit 21 records the catheter image 51, the position of the catheter image 51 in the longitudinal direction of the image acquisition catheter 40, and the position information of the medical instrument in association with one another in the auxiliary storage device 23 or a mass storage device connected to the HIS (S503).

The control unit 21 generates classification data 52 classified for each visualized subject for each portion constituting the catheter image 51 (S504). In FIG. 4, the classification data 52 is illustrated by a schematic diagram in which the catheter image 51 is colored into each classification based on the classification result.

The control unit 21 determines whether the user designates two-dimensional display or designates three-dimensional display (S505). When determining that the user designates the two-dimensional display (2D in S505), the control unit 21 displays the catheter image 51 and the classification data 52 on the display device 31 by two-dimensional display (S506).

In S505 in FIG. 4, description is made as if selection is either "two-dimensional display" and "three-dimensional display" such as "2D/3D". However, when the user selects "3D", the control unit 21 may display both "two-dimensional display" and "three-dimensional display".

When determining that the user designates three-dimensional display (3D in S505), the control unit 21 determines whether or not the position information of the medical instrument sequentially recorded in S503 is normal (S511). When determining that the position information is not normal (NO in S511), the control unit 21 corrects the position information (S512). Details of the processing performed in S511 and S512 will be described later.

When determining that the position information is normal (YES in S511), or after the end of S512, the control unit 21 performs three-dimensional display illustrating the structure of the site being observed and the position of the medical instrument (S513). As described above, the control unit 21 may display both the three-dimensional display and the two-dimensional display on one screen.

After ending S506 or S513, the control unit 21 determines whether or not acquisition of the catheter image 51 has ended (S507). For example, when receiving an end instruction from the user, the control unit 21 determines to end the processing.

When determining not to end the processing (NO in S507), the control unit 21 returns to S501. When determining to end the processing (YES in S507), the control unit 21 ends the processing.

FIG. 4 explains the flow of processing in a case of performing the two-dimensional display (S506) or the three-dimensional display (S513) in real time during capturing of the series of catheter images 51. The control unit 21 may perform two-dimensional display or three-dimensional display in non-real time on the basis of the data recorded in S503.

Figure 5A:
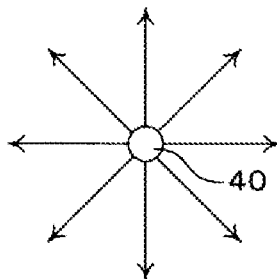
FIG. 5A is an explanatory view schematically illustrating an operation of the image acquisition catheter.
Figure 5B:
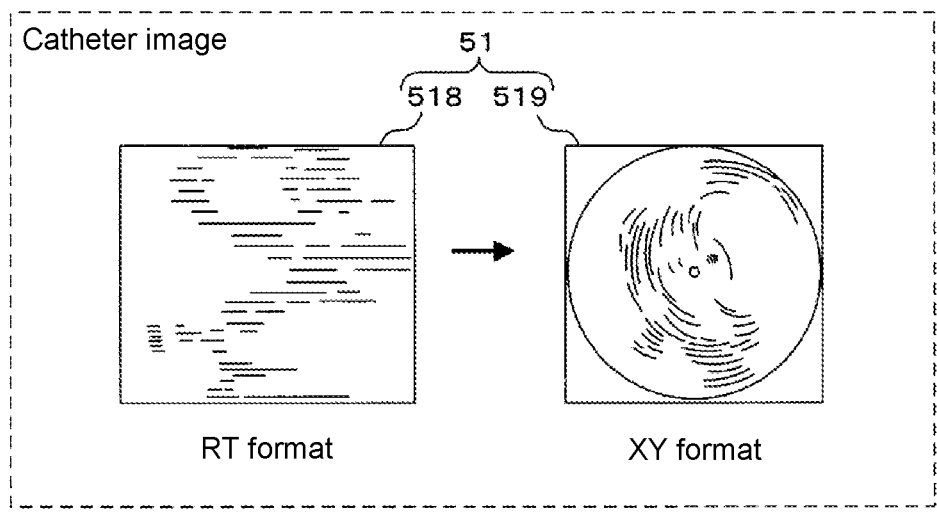
FIG. 5B is an explanatory view schematically illustrating a catheter image captured by the image acquisition catheter.
Figure 5C:
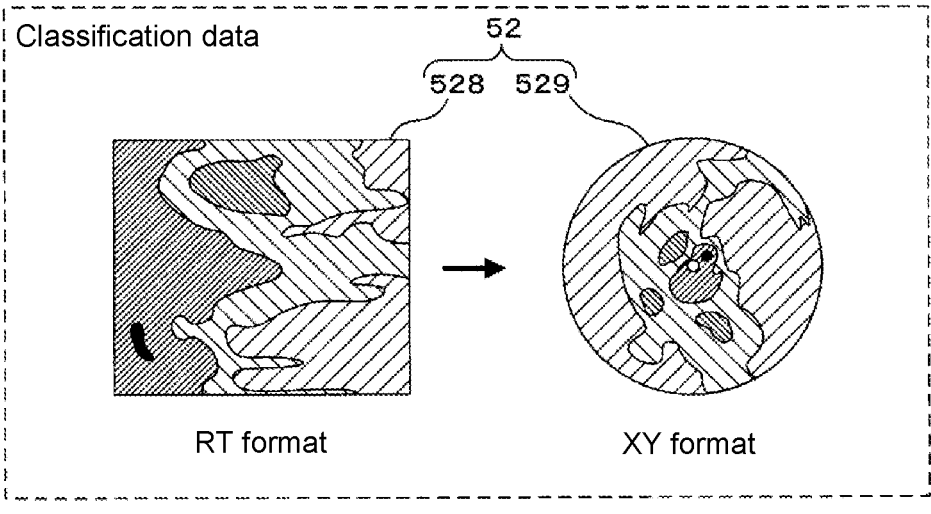
FIG. 5C is an explanatory view schematically explaining classification data generated on the basis of a catheter image.

FIG. 5A is an explanatory view schematically illustrating the operation of the image acquisition catheter 40. FIG. 5B is an explanatory view schematically illustrating the catheter image 51 captured by the image acquisition catheter 40. FIG. 5C is an explanatory view schematically explaining the classification data 52 generated on the basis of the catheter image 51. A radius-theta (RT) format and an XY format will be described with reference to FIGS. 5A to 5C.

As described above, the sensor 42 transmits and receives ultrasound waves while rotating inside the image acquisition catheter 40. As schematically indicated by eight arrows in FIG. 5A, the catheter control unit 271 acquires radial scanning line data around the image acquisition catheter 40.

The catheter control unit 271 can generate the catheter image 51 illustrated in FIG. 5B in two formats of an RT format catheter image 518 and an XY format catheter image 519 on the basis of the scanning line data. The RT format catheter image 518 is an image generated by arranging pieces of scanning line data in parallel with one another. The lateral direction of the RT format catheter image 518 indicates the distance from the image acquisition catheter 40.

The longitudinal direction of the RT format catheter image 518 indicates the scanning angle. One RT format catheter image 518 is formed by arraying, in parallel in the order of the scanning angle, the scanning line data acquired by the sensor 42 rotating by 360 degrees.

In FIG. 5B, the left side of the RT format catheter image 518 indicates a place close to the image acquisition catheter 40, and the right side of the RT format catheter image 518 indicates a place far from the image acquisition catheter 40.

The XY format catheter image 519 is an image generated by radially arranging and interpolating the pieces of scanning line data. The XY format catheter image 519 indicates a tomographic image of the subject being cut perpendicularly to the image acquisition catheter 40 at the position of the sensor 42.

FIG. 5C schematically illustrates the classification data 52 classified for each visualized subject for each portion constituting the catheter image 51. The classification data 52 can also be displayed in the two formats of RT format classification data 528 and XY format classification data 529. Since an image conversion method between the RT format and the XY format is known, description of the conversion method between the RT format and the XY formation is omitted.

In FIG. 5C, the thick right-downward hatching indicates a biological tissue region forming a cavity into which the image acquisition catheter 40 is inserted, such as an atrial wall and a ventricular wall. The thin left-downward hatching indicates the inside of the first cavity, which is a blood flow region into which the distal part of the image acquisition catheter 40 is inserted. The thin right-downward hatching indicates the inside of the second cavity, which is a blood flow region other than the first cavity.

In the case of performing atrial septal puncture from the right atrium to the left atrium, the first cavity is the right atrium, and the second cavity is the left atrium, the right ventricle, the left ventricle, the aorta, the coronary artery, and the like. In the following description, the inside of the first cavity is referred to as first inner cavity region, and the inside of the second cavity is referred to as second inner cavity region.

The thick left-downward hatching indicates a non-inner cavity region, which is neither the first inner cavity region nor the second inner cavity region of the non-biological tissue region. The non-inner cavity region includes an out-of-cardiac region and a region outside the heart structure. When the visualizable range of the image acquisition catheter 40 is too small to sufficiently visualize the wall on the distal side of the left atrium, the inside of the left atrium is also included in the non-inner cavity region. Similarly, the inner cavity such as the left ventricle, the pulmonary artery, the pulmonary vein, and the aortic arch are also included in the non-inner cavity region when the distal wall cannot be sufficiently visualized.

Black indicates a medical instrument region in which a medical instrument such as a Brockenbrough needle is visualized. In the following description, the biological tissue region and the non-biological tissue region may be collectively referred to as biological tissue-related region.

The medical instrument is not necessarily inserted into the same first cavity as the image acquisition catheter 40. Depending on the manipulation, the medical instrument may be inserted into the second cavity.

The hatching and the black illustrated in FIG. 5C are examples of modes in which those regions can be distinguished. Those regions are displayed on the display device 31 using, for example, different colors. The control unit 21 implements the function of a first mode output unit that outputs the first inner cavity region, the second inner cavity region, and the biological tissue region in a distinguishable mode. The control unit 21 also implements the function of a second mode output unit that outputs the first inner cavity region, the second inner cavity region, the non-inner cavity region, and the biological tissue region in a distinguishable mode.

For example, in the case of confirming the position of the Brockenbrough needle in order to perform the atrial septal puncture, the display in the XY format is suitable during the IVR manipulation. However, in the XY display, the information in the vicinity of the image acquisition catheter 40 is compressed and the data amount is reduced, and data that does not originally exist is added by interpolation at a position away from the image acquisition catheter 40. Therefore, when the catheter image 51 is analyzed, use of the RT format image can obtain a more accurate result than that by use of the XY format image.

In the following description, the control unit 21 generates the RT format classification data 528 on the basis of the RT format catheter image 518. The control unit 21 converts the XY format catheter image 519 to generate the RT format catheter image 518, and converts the RT format classification data 528 to generate the XY format classification data 529.

The classification data 52 will be described with a specific example. A "biological tissue region label" is recorded in a pixel classified into the "biological tissue region", a "first inner cavity region label" is recorded in a pixel classified into the "first inner cavity region", a "second inner cavity region label" is recorded in a pixel classified into the "second inner cavity region", a "non-inner cavity region label" is recorded in a pixel classified into the "non-inner cavity region", a "medical instrument region label" is recorded in a pixel classified into the "medical instrument region", and a "non-biological tissue region label" is recorded in a pixel classified into the "non-biological tissue region". Each label is indicated by an integer, for example.

The control unit 21 may generate the XY format classification data 529 on the basis of the XY format catheter image 519. The control unit 21 may generate the RT format classification data 528 on the basis of the XY format classification data 529.

Figure 6:
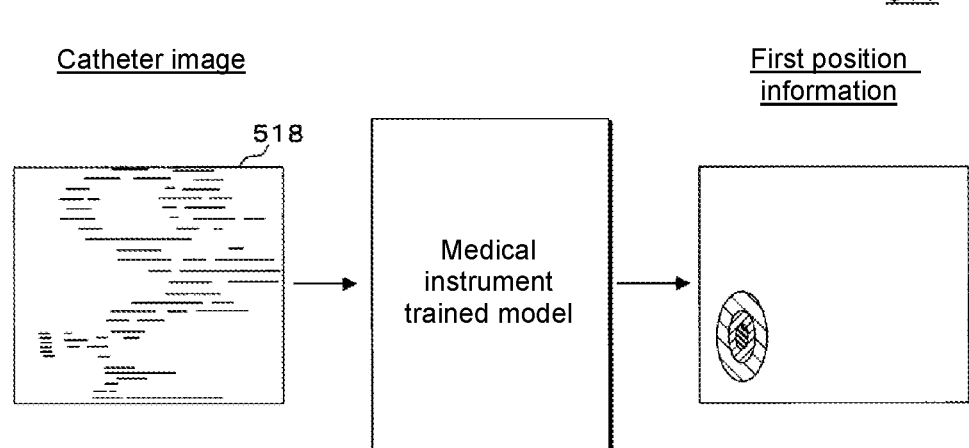
FIG. 6 is an explanatory view explaining a configuration of a medical instrument trained model.

FIG. 6 is an explanatory view explaining the configuration of a medical instrument trained model 611. The medical instrument trained model 611 is a model that receives the catheter image 51 and outputs the first position information regarding the position where the medical instrument is visualized. The medical instrument trained model 611 implements S502 described with reference to FIG. 4. An output layer of the medical instrument trained model 611 functions as a first position information output unit that outputs the first position information.

In FIG. 6, input of the medical instrument trained model 611 is the RT format catheter image 518. The first position information is a probability that the medical instrument for each portion on the RT format catheter image 518 is visualized. In FIG. 6, a place where the probability that the medical instrument is visualized is relatively high is indicated by dark hatching, and a place where the probability that the medical instrument is visualized is relatively low is indicated by no hatching.

The medical instrument trained model 611 is generated by machine learning using, for example, a neural network structure of a convolutional neural network (CNN). Examples of the CNN that can be used for generation of the medical instrument trained model 611 include a region based convolutional neural network (R-CNN), you only look once (YOLO), U-Net, and a generative adversarial network (GAN). The medical instrument trained model 611 may be generated using a neural network structure other than the CNN.

The medical instrument trained model 611 may be a model that receives a plurality of catheter images 51 acquired in time series and outputs the first position information with respect to the latest catheter image 51. The medical instrument trained model 611 can be generated by combining a model that receives time-series input such as a recurrent neural network (RNN) with the above-described neural network structure.

The RNN can be, for example, a long short-term memory (LSTM). When the LSTM is used, the medical instrument trained model 611 includes a memory portion that holds information regarding the catheter image 51 input in the past. The medical instrument trained model 611 outputs the first position information on the basis of the information held in the memory portion and the latest catheter image 51.

When the plurality of catheter images 51 acquired in time series is used, the medical instrument trained model 611 may include a recursive input portion that inputs, together with the next catheter image 51, an output based on the catheter image 51 input in the past. The medical instrument trained model 611 outputs the first position information on the basis of the latest catheter image 51 and the input from the recursive input portion. Use of the catheter images 51 acquired in time series makes it possible to implement the medical instrument trained model 611 that is hardly affected by image noise or the like and outputs the first position information with relatively high accuracy.

The medical instrument trained model 611 may output a place where the probability that the medical instrument is visualized is relatively high using the position of one pixel on the catheter image 51 that has received the input. For example, the medical instrument trained model 611 may be a model that, after calculating the probability that the medical instrument is visualized for each site on the catheter image 51 as illustrated in FIG. 6, outputs the position of the pixel having the highest probability. The medical instrument trained model 611 may output the position of the center of gravity of the region where the probability that the medical instrument is visualized exceeds a predetermined threshold. The medical instrument trained model 611 may output a region in which the probability that the medical instrument is visualized exceeds a predetermined threshold.

There is a case where a plurality of medical instruments are used simultaneously. When a plurality of medical instruments are visualized on the catheter image 51, the medical instrument trained model 611 is desirably a model that outputs the first position information of each of the plurality of medical instruments.

The medical instrument trained model 611 may be a model that outputs only the first position information of one medical instrument. The control unit 21 can input, to the medical instrument trained model 611, the RT format catheter image 518 with masking on the periphery of the first position information output from the medical instrument trained model 611 and acquire the first position information of the second medical instrument. By repeating the same processing, the control unit 21 can also acquire the first position information of the third and subsequent medical instruments.

Figure 7:
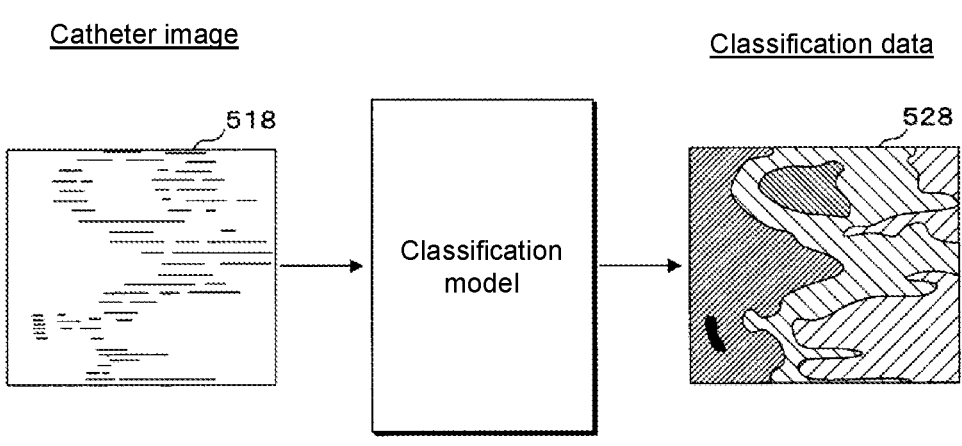
FIG. 7 is an explanatory view explaining a configuration of a classification model.

FIG. 7 is an explanatory view explaining the configuration of a classification model 62. The classification model 62 is a model that receives the catheter image 51 and outputs the classification data 52 classified for each visualized subject for each portion constituting the catheter image 51. The classification model 62 implements S504 described with reference to FIG. 4.

Specific examples will be described. The classification model 62 classifies each pixel constituting the input RT format catheter image 518 into, for example, the "biological tissue region", the "first inner cavity region", the "second inner cavity region", the "non-inner cavity region", and the "medical instrument region", and outputs the RT format classification data 528 in which the position of the pixel is associated with the label indicating the classification result.

The classification model 62 may divide the catheter image 51 into regions of optional size, for example, a total of 9 pixels including 3 vertical pixels and 3 horizontal pixels, and output classification data 52 obtained by classifying those regions. The classification model 62 can be, for example, a trained model that performs semantic segmentation on the catheter image 51. A specific example of the classification model 62 will be described later.

Figures 8, 9:
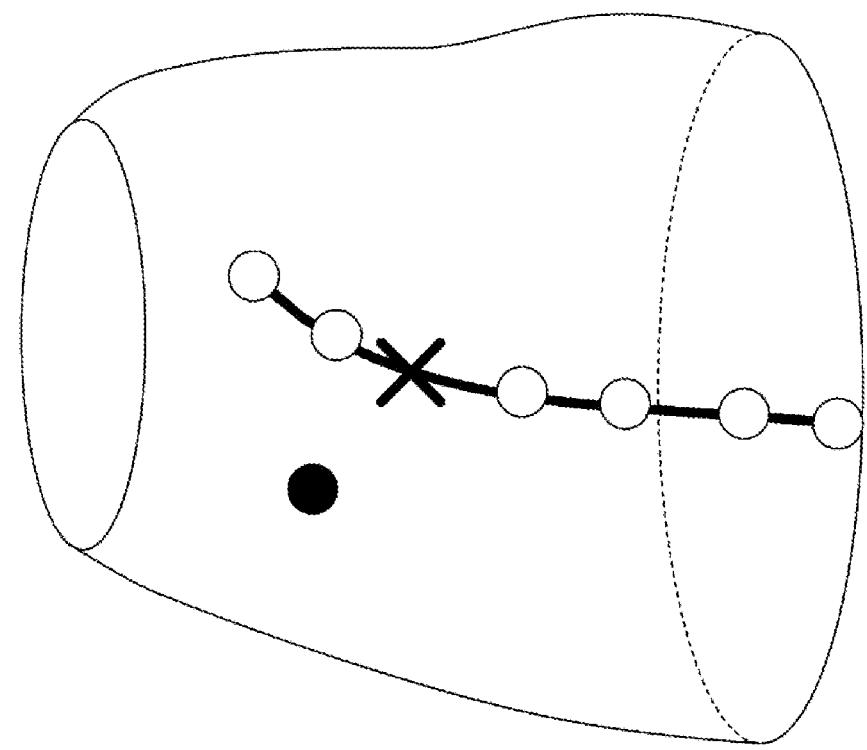
FIG. 8 is an explanatory view explaining an outline of processing regarding position information.
FIG. 9 is an explanatory view explaining a record layout of a medical instrument position training data database (DB).

FIG. 8 is an explanatory view explaining an outline of processing regarding position information. The plurality of catheter images 51 are captured while the sensor 42 is moved in the longitudinal direction of the image acquisition catheter 40. In FIG. 8, a substantially truncated cone line drawing schematically illustrates a biological tissue region three-dimensionally constructed on the basis of the plurality of catheter images 51. The inside of the substantially truncated cone means the first inner cavity region.

White and black circles indicate the positions of the medical instruments acquired from the respective catheter images 51. Among them, since the black circle is at a position far away from the white circle, it is determined to be an erroneous detection. The shape of the medical instrument can be reproduced by the thick line smoothly coupling the white circles. A cross mark (x) indicates complement information obtained by complementing the position information of an undetected medical instrument.

Details of the processing described with reference to FIG. 8 will be described in the eighth embodiment. The processing in S511 and S512 described with reference to FIG. 4 is implemented by the processing described with reference to FIG. 8.

It is known that for example, in a case where the medical instrument and the biological tissue region are in contact with each other, there is a case where it is difficult to identify where the medical instrument is visualized even if a user such as a skilled medical doctor or a medical technician interprets one catheter image 51 in a still image state. However, in a case where of observing the catheter image 51 as a moving image, the user can relatively easily determine the position of the medical instrument. This is because the user interprets the image while expecting that the medical instrument exists at the similar position to that in the previous frame.

In the processing described with reference to FIG. 8, the medical instrument is reconstructed so as not to cause inconsistency using the position information of the medical instrument acquired from each of the plurality of catheter images 51. By performing such processing, similarly to the case where the user observes the moving image, it is possible to achieve the catheter system 10 that accurately determines the position of the medical instrument and displays the shape of the medical instrument in the three-dimensional image.

According to the present embodiment, it is possible to provide the catheter system 10 that assists understanding of the catheter image 51 acquired using the image acquisition catheter 40 by the display of S506 and S513. By using the catheter system 10 of the present embodiment, the user can accurately grasp the position of the medical instrument, and can safely perform IVR.

Second Embodiment

The present embodiment relates to a generation method for the medical instrument trained model 611. Description of parts common to the first embodiment will be omitted. In the present embodiment, a case where the medical instrument trained model 611 is generated using the information processing device 20 described with reference to FIG. 3 will be described as an example.

The medical instrument trained model 611 may be created using a computer or the like different from the information processing device 20. The medical instrument trained model 611 on which the machine learning is completed may be copied to the auxiliary storage device 23 via the network. The medical instrument trained model 611 trained by one piece of hardware can be used by the plurality of information processing devices 20.

FIG. 9 is an explanatory view explaining a record layout of a medical instrument position training data database (DB) 71. The medical instrument position training data DB 71 is a database in which the catheter image 51 and the position information of the medical instrument are recorded in association with each other, and is used for training of the medical instrument trained model 611 by machine learning.

The medical instrument position training data DB 71 has a catheter image field and a position information field. In the catheter image field, the catheter image 51 such as the RT format catheter image 518 is recorded. In the catheter image field, what is called sound ray data indicating an ultrasound signal received by the sensor 42 may be recorded. In the catheter image field, scanning line data generated on the basis of the sound ray data may be recorded.

In the position information field, position information of the medical instrument visualized in the catheter image 51 is recorded. The position information is information indicating the position of one pixel marked on the catheter image 51 by a labeler as described later, for example. The position information may be information indicating a region of a circle centered around a point marked on the catheter image

51 by the labeler. The circle has a dimension that does not exceed the size of the medical instrument visualized in the catheter image 51. The circle has a size inscribed in a square having 50 vertical and horizontal pixels or less, for example.

Figure 10:
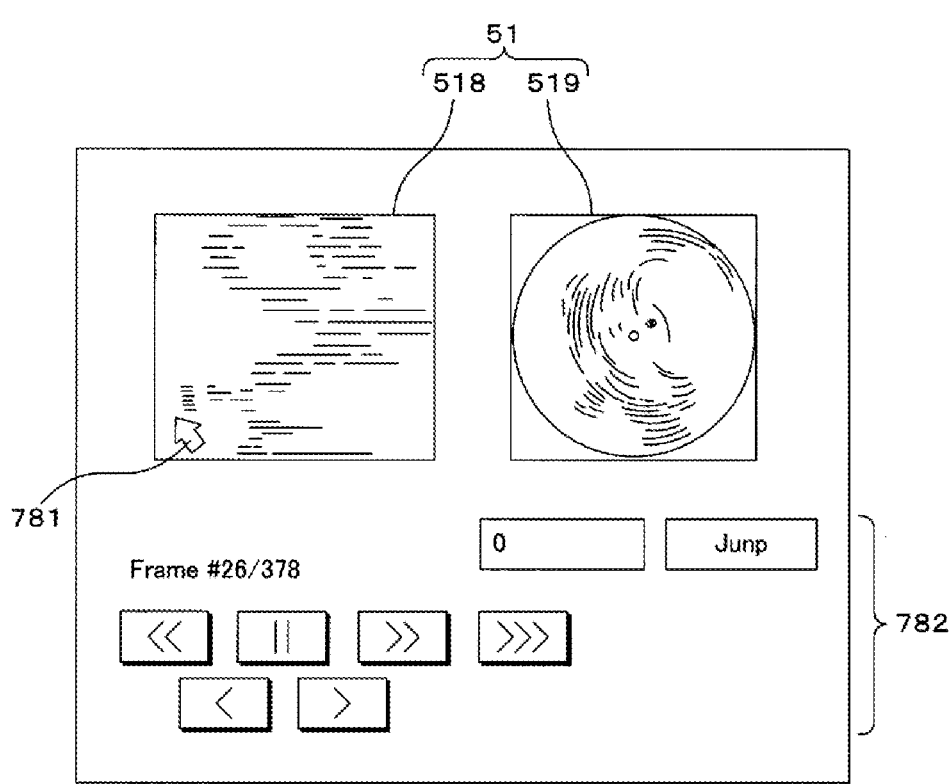
FIG. 10 is an example of a screen used for creation of the medical instrument position training data DB.

FIG. 10 is an example of a screen used for creation of the medical instrument position training data DB 71. A set of catheter images 51 of the RT format catheter image 518 and the XY format catheter image 519 are displayed on the screen of FIG. 10. The RT format catheter image 518 and the XY format catheter image 519 are images created on the basis of the same sound ray data.

A control button area 782 is displayed below the catheter image 51. In an upper part of the control button area 782, a frame number of the catheter image 51 being displayed and a jump button used when the user inputs an optional frame number and jumps the display are arranged.

Various buttons used when the user performs operations such as fast delivery, rewind, and frame advance are arranged below the frame number and the like. Since these buttons are similar to those generally used in various image reproduction devices and the like, the description of the various buttons will be omitted.

The user of the present embodiment is a person in charge of creating training data by viewing the catheter image 51 recorded in advance and labeling the position of the medical instrument. In the following description, a person in charge of creating training data is referred to as labeler. The labeler can be, for example, a medical doctor skilled in the interpretation of the catheter image 51, a laboratory technician, or a person trained to perform accurate labeling. In the following description, there is a case where an operation of marking the catheter image 51 by the labeler to apply a label is referred to as marking.

The labeler observes the displayed catheter image 51 to determine the position where the medical instrument is visualized. In general, the region where the medical instrument is visualized is very small with respect to the area of the entire catheter image 51. The labeler moves a cursor 781 to substantially the center of the region where the medical instrument is visualized, and performs marking by a click operation or the like. When the display device 31 is a touchscreen, the labeler may perform marking by a tap operation using a finger, a stylus pen, or the like. The labeler may perform marking by what is called flick operation.

The labeler may perform marking on the catheter image 51 of either of the RT format catheter image 518 and the XY format catheter image 519. The control unit 21 may display a mark at a corresponding position in the other catheter image 51.

The control unit 21 creates a new record in the medical instrument position training data DB 71, and records the catheter image 51 and the position marked by the labeler in association with each other. The control unit 21 displays the next catheter image 51 on the display device 31. By repeating the above processing many times (i.e., a relatively large number of times), the medical instrument position training data DB 71 is created.

That is, the labeler can sequentially perform marking on the plurality of catheter images 51 only by performing a click operation or the like on the catheter image 51 without operating each button in the control button area 782. All the operation performed by the labeler on one catheter image 51 in which one medical instrument is visualized is only one click operation or the like.

As described above, there is a case where a plurality of medical instruments are visualized on the catheter image 51. The labeler can perform marking on each medical instrument by one click operation or the like. In the following description, a case where one medical instrument is visualized in one catheter image 51 will be described as an example.

Figure 11:
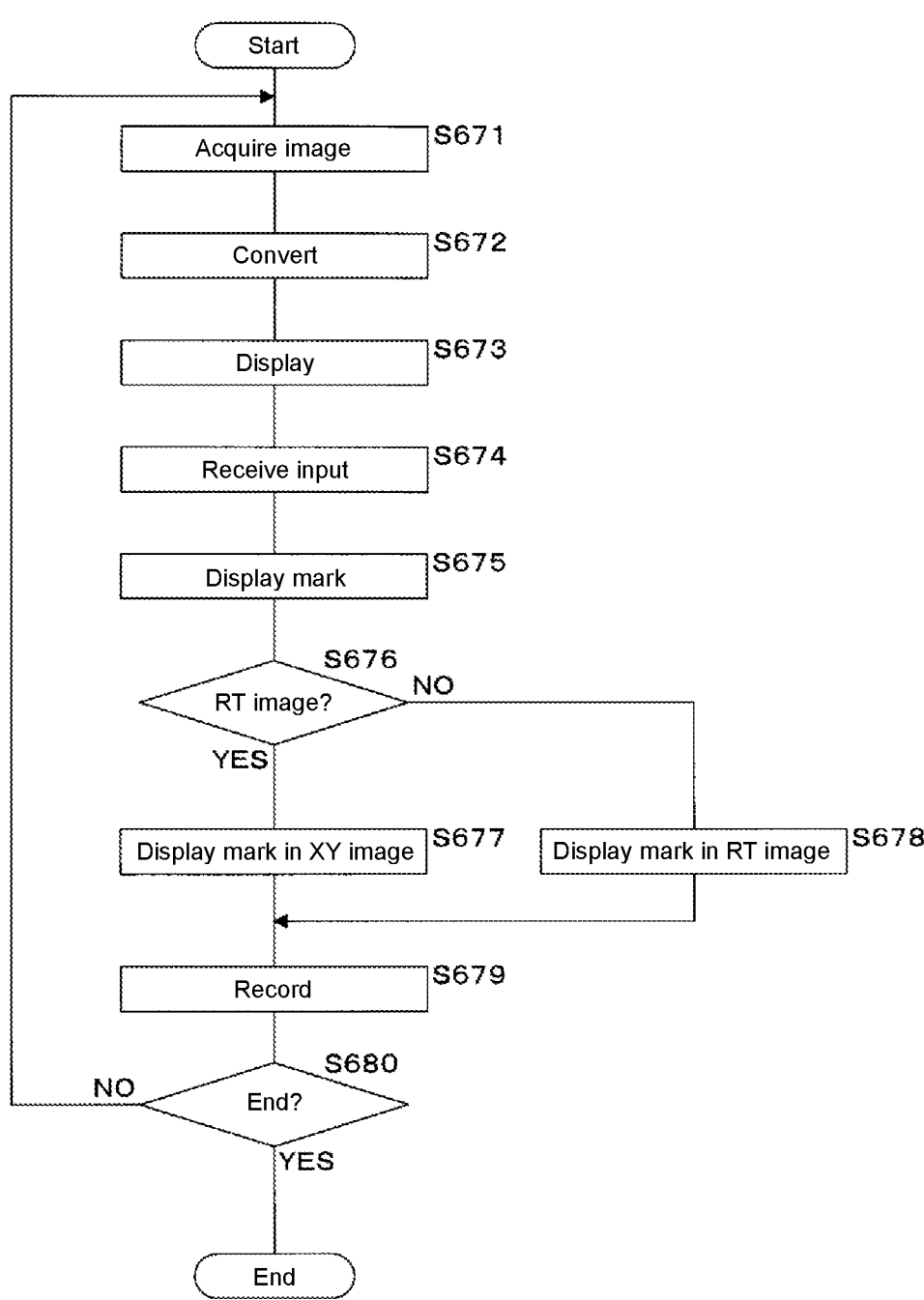
FIG. 11 is a flowchart explaining a flow of processing of a program for creating the medical instrument position training data DB.

FIG. 11 is a flowchart explaining the flow of the processing of a program for creating the medical instrument position training data DB 71. A case where the medical instrument position training data DB 71 is created using the information processing device 20 will be described as an example. The program of FIG. 11 may be executed by hardware different from the information processing device 20.

Prior to execution of the program of FIG. 11, a large number of catheter images 51 are recorded in the auxiliary storage device 23 or an external mass storage device. In the following description, a case where the catheter image 51 is recorded in the auxiliary storage device 23 in the form of moving image data including a plurality of RT format catheter images 518 captured in time series will be described as an example.

The control unit 21 acquires the RT format catheter image 518 of one frame from the auxiliary storage device 23 (S671). By converting the RT format catheter image 518, the control unit 21 generates the XY format catheter image 519 (S672). The control unit 21 displays, on the display device 31, the screen described with reference to FIG. 10 (S673).

The control unit 21 receives an input operation of the position information by the labeler via the input device 32 (S674). Specifically, the input operation is a click operation or a tap operation on the RT format catheter image 518 or the XY format catheter image 519.

The control unit 21 displays a mark such as a small circle at a position where the input operation has been received (S675). Detailed description of the reception of the input operation on the image displayed on the display device 31 via the input device 32 and the display of a mark on the display device 31 will be omitted because they are user interfaces that have been conventionally used.

The control unit 21 determines whether or not the image for which the input operation has been received in S674 is the RT format catheter image 518 (S676). When determining that the catheter image is the RT format catheter image 518 (YES in S676), the control unit 21 displays a mark also at a corresponding position in the XY format catheter image 519 (S677). When determining that the catheter image is not the RT format catheter image 518 (NO in S676), the control unit 21 displays a mark also at a corresponding position in the RT format catheter image 518 (S678).

The control unit 21 creates a new record in the medical instrument position training data DB 71. The control unit 21 records the catheter image 51 and the position information input by the labeler in association with each other in the medical instrument position training data DB 71 (S679).

The catheter image 51 recorded in S679 may be only the RT format catheter image 518 acquired in S671 or both the RT format catheter image 518 and the XY format catheter image 519 generated in S672. The catheter image 51 recorded in S679 may be sound ray data for one rotation received by the sensor 42 or scanning line data generated by performing signal processing on the sound ray data.

The position information recorded in S679 is information indicating the position of one pixel on the RT format catheter image 518 corresponding to, for example, the position where the labeler has performed a click operation or the like using the input device 32. The position information may be information indicating a position where the labeler has performed a click operation or the like and a range around the position.

The control unit 21 determines whether or not to end the processing (S680). For example, when the processing of the catheter image 51 recorded in the auxiliary storage device 23 is ended, the control unit 21 determines to end the processing. When determining to end the processing (YES in S680), the control unit 21 ends the processing.

When determining not to end the processing (NO in S680), the control unit 21 returns to S671. In S671, the control unit 21 acquires the next RT format catheter image 518, and executes the processing in S672 and subsequent processes or steps. That is, the control unit 21 automatically acquires and displays the next RT format catheter image 518 without waiting for an operation on the button displayed in the control button area 782.

By the loop of S671 to S680, the control unit 21 records, in the medical instrument position training data DB 71, the training data based on the large number of RT format catheter images 518 recorded in the auxiliary storage device 23.

The control unit 21 may display, for example, a "save button" on the screen described with reference to FIG. 10, and execute S679 when receiving selection of the "save button". Furthermore, the control unit 21 may display, for example, an "AUTO button" on the screen described with reference to FIG. 10, and may automatically execute S679 without waiting for selection of the "save button" while receiving the selection of the "AUTO button".

In the following description, a case where the catheter image 51 recorded in the medical instrument position training data DB 71 in S679 is the RT format catheter image 518, and the position information is the position of one pixel on the RT format catheter image 518 will be described as an example.

Figure 12:
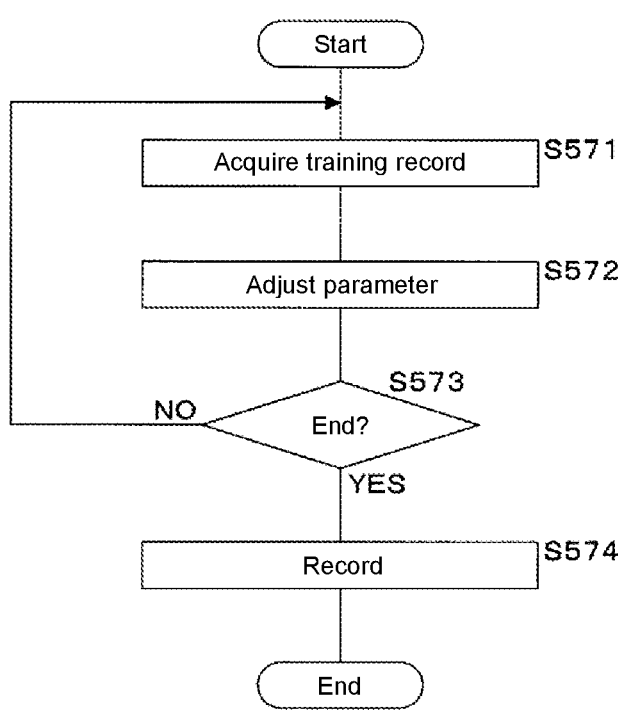
FIG. 12 is a flowchart explaining a flow of processing of a medical instrument trained model generation program.

FIG. 12 is a flowchart explaining the flow of the processing of a generation program of the medical instrument trained model 611. Prior to execution of the program of FIG. 12, an untrained model in which, for example, a convolution layer, a pooling layer, and a fully connected layer are combined is prepared. As described above, the untrained model can be, for example, a CNN model. Examples of the CNN that can be used for generation of the medical instrument trained model 611 include R-CNN, YOLO, U-Net, GAN, and the like. The medical instrument trained model 611 may be generated using a neural network structure other than the CNN.

The control unit 21 acquires a training record used for training of one epoch (i.e., one entire passing of training data through an algorithm) from the medical instrument position training data DB 71 (S571). As described above, the training record recorded in the medical instrument position training data DB 71 is a combination of the RT format catheter image 518 and the coordinates indicating the position of the medical instrument visualized in the RT format catheter image 518.

When the RT format catheter image 518 is input to the input layer of the model, the control unit 21 adjusts a parameter of the model so that the position of the pixel corresponding to the position information is output from the output layer (S572). In the acquisition of the training record and the parameter adjustment of the model, the program may appropriately have a function of causing the control unit 21 to execute reception of correction by the user, presentation of a basis of determination, additional learning, and the like.

The control unit 21 determines whether or not to end the processing (S573). For example, when ending the learning of the predetermined number of epochs, the control unit 21 determines to finish the processing. The control unit 21 may acquire test data from the medical instrument position training data DB 71, input the test data to the model under machine learning, and determine to end the processing in a case where an output with predetermined accuracy is obtained.

When determining not to end the processing (NO in S573), the control unit 21 returns to S571. When determining to end the processing (YES in S573), the control unit 21 records, in the auxiliary storage device 23, the parameter of the trained medical instrument position training data DB 71 (S574). Thereafter, the control unit 21 ends the processing. By the above processing, the medical instrument trained model 611 that receives the catheter image 51 and outputs the first position information is generated.

Prior to the execution of the program of FIG. 12, a model that receives time-series input such as RNN may be prepared. The RNN is, for example, an LSTM. In S572, when the plurality of RT format catheter images 518 captured in time series is input to the input layer of the model, the control unit 21 adjusts the parameter of the model so that the position of the pixel corresponding to the position information associated with the final RT format catheter image 518 is output in time series from the output layer.

Figure 13:
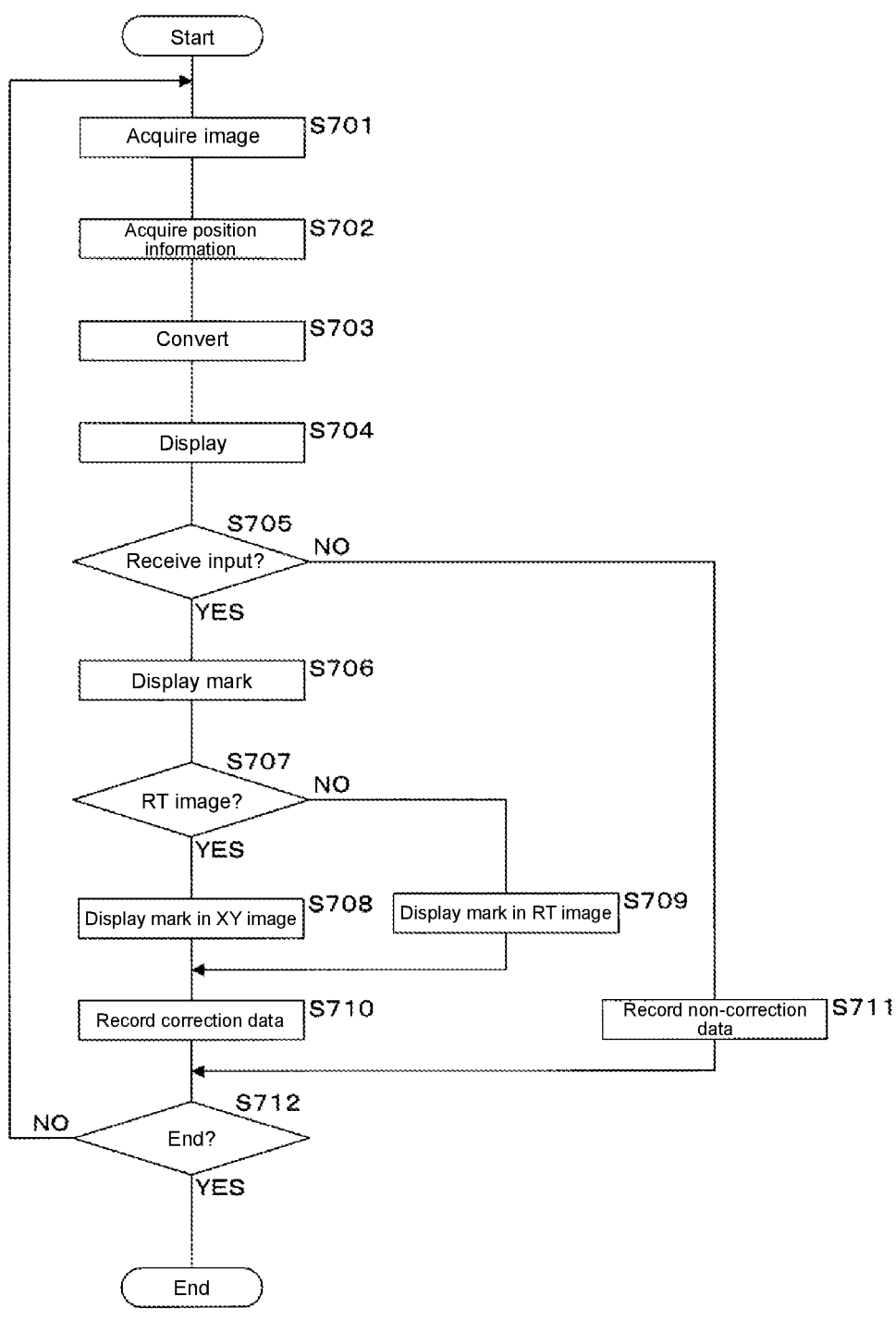
FIG. 13 is a flowchart explaining a flow of processing of a program for adding data to the medical instrument position training data DB.

FIG. 13 is a flowchart explaining the flow of the processing of a program for adding data to the medical instrument position training data DB 71. The program of FIG. 13 is a program for adding training data to the medical instrument position training data DB 71 after creating the medical instrument trained model 611. The added training data is used for additional learning of the medical instrument trained model 611.

Prior to execution of the program of FIG. 13, a large number of catheter images 51 that have not yet been used for creation of the medical instrument position training data DB 71 are recorded in the auxiliary storage device 23 or the external mass storage device. In the following description, a case where the catheter image 51 is recorded in the auxiliary storage device 23 in the form of moving image data including a plurality of RT format catheter images 518 captured in time series will be described as an example.

The control unit 21 acquires the RT format catheter image 518 of one frame from the auxiliary storage device 23 (S701). The control unit 21 inputs the RT format catheter image 518 to the medical instrument trained model 611 and acquires the first position information (S702).

By converting the RT format catheter image 518, the control unit 21 generates the XY format catheter image 519 (S703). The control unit 21 displays, on the display device 31, the screen described with reference to FIG. 10 in a state where the mark indicating the first position information acquired in S702 is superimposed on each of the RT format catheter image 518 and the XY format catheter image 519 (S704).

When determining that the position of the automatically displayed mark is inappropriate, the labeler performs one click operation or the like to input the correct position of the medical instrument. That is, the labeler inputs a correction instruction for the automatically displayed mark.

The control unit 21 determines whether or not to have received an input operation by the labeler via the input device 32 within a predetermined time (S705). It is desirable that the labeler can appropriately set the predetermined time.

Specifically, the input operation is a click operation or a tap operation on the RT format catheter image 518 or the XY format catheter image 519.

When determining to have received the input operation (YES in S705), the control unit 21 displays a mark such as a small circle at the position where the input operation has been received (S706). The mark displayed in S706 desirably has a color, a shape, or the like different from those of the mark indicating the position information acquired in S702. The control unit 21 may delete the mark indicating the position information acquired in S702.

The control unit 21 determines whether or not the image for which the input operation has been received in S705 is the RT format catheter image 518 (S707). When determining that the catheter image is the RT format catheter image 518 (YES in S707)), the control unit 21 displays a mark also at a corresponding position in the XY format catheter image 519 (S708). When determining that the catheter image is not the RT format catheter image 518 (NO in S707), the control unit 21 displays a mark also at a corresponding position in the RT format catheter image 518 (S709).

The control unit 21 creates a new record in the medical instrument position training data DB 71. The control unit 21 records, in the medical instrument position training data DB 71, correction data in which the catheter image 51 is associated with the position information input by the labeler (S710).

When determining to have not received the input operation (NO in S705), the control unit 21 creates a new record in the medical instrument position training data DB 71. The control unit 21 records, in the medical instrument position training data DB 71, non-correction data in which the catheter image 51 is associated with the first position information acquired in S532 (S711).

After S710 or S711 ends, the control unit 21 determines whether or not to end the processing (S712). For example, when the processing of the catheter image 51 recorded in the auxiliary storage device 23 is ended, the control unit 21 determines to end the processing. When determining to end the processing (YES in S712), the control unit 21 ends the processing.

When determining not to end the processing (NO in S712), the control unit 21 returns to S701. In S701, the control unit 21 acquires the next RT format catheter image 518, and executes the processing in S702 and subsequent steps. By the loop of S701 to S712, the control unit 21 adds, in the medical instrument position training data DB 71, the training data based on the large number of RT format catheter images 518 recorded in the auxiliary storage device 23.

The control unit 21 may display an "OK button" for approving output by the medical instrument trained model 611, for example, on the screen described with reference to FIG. 10. When receiving the selection of the "OK button", the control unit 21 determines that an instruction indicating "NO" is received in S705 and executes S711.

According to the present embodiment, the labeler can perform marking on one medical instrument visualized in the catheter image 51 only by one operation such as one click operation or one tap operation. The control unit 21 may receive an operation of marking one medical instrument by what is called a double click operation or a double tap operation. Since the marking work can be greatly saved as compared with the case of marking the boundary line of the medical instrument, the burden on the labeler can be reduced. According to the present embodiment, it is possible to create a large amount of training data in a relatively short time.

According to the present embodiment, when a plurality of medical instruments are visualized on the catheter image 51, the labeler can perform marking on each medical instrument by one click operation or the like.

The control unit 21 may display, for example, an "OK button" on the screen described with reference to FIG. 10, and execute S679 when receiving selection of the "OK button".

According to the present embodiment, by superimposing and displaying, on the catheter image 51, the position information acquired by the medical instrument trained model 611, it is possible to relatively quickly create additional training data while reducing the burden on the labeler.

Modification 2-1

The medical instrument position training data DB 71 may have a field for recording the type of medical instrument. In such a case, on the screen described with reference to FIG. 10, the control unit 21 receives an input of the type of the medical instruments such as a "Brockenbrough needle", a "guide wire", or a "balloon catheter".

By performing machine learning using the medical instrument position training data DB 71 created in this manner, the medical instrument trained model 611 that outputs the type of the medical instrument in addition to the position of the medical instrument can be generated.

Third Embodiment

The present embodiment relates to the catheter system 10 that acquires second position information regarding the position of a medical instrument from the catheter image 51 using two trained models. Description of parts common to the second embodiment will be omitted.

Figure 14:
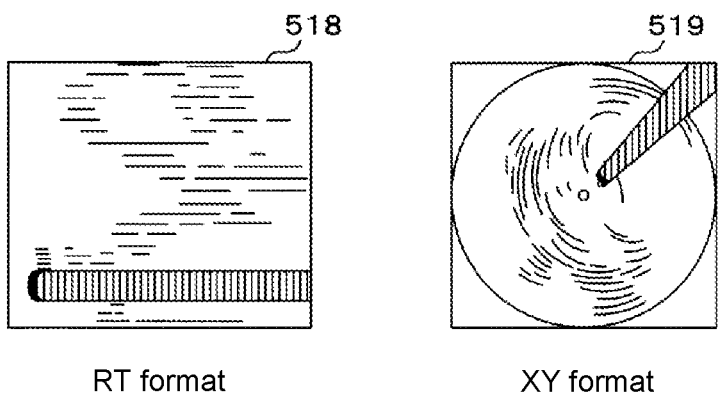
FIG. 14 is an explanatory view explaining visualization of a medical instrument.

FIG. 14 is an explanatory view explaining visualization of a medical instrument. In FIG. 14, the medical instrument visualized in the RT format catheter image 518 and the XY format catheter image 519 is emphasized.

In general, medical instruments strongly reflect ultrasound waves as compared to biological tissues. The ultrasound wave irradiated from the sensor 42 is less likely to reach farther than the medical instrument. Therefore, the medical instrument is visualized by a high echo region indicating a side close to the image acquisition catheter 40 and a low echo region following the rear of the high echo region. A low echo region following the rear of the medical instrument is described as an acoustic shadow. In FIG. 14, a part of the acoustic shadow is indicated by vertical hatching.

In the RT format catheter image 518, the acoustic shadow is visualized linearly in the horizontal direction. In the XY format catheter image 519, the acoustic shadow is visualized in a fan shape. In either case, a high luminance region is visualized in a site closer to the image acquisition catheter 40 than the acoustic shadow. The high luminance region may be visualized in a mode of what is called multiple echoes that regularly repeat along the scanning line direction.

On the basis of the scanning angle direction of the RT format catheter image 518, i.e., the lateral features in FIG. 14, the scanning angle at which the medical instrument is being visualized can be determined.

Figure 15:
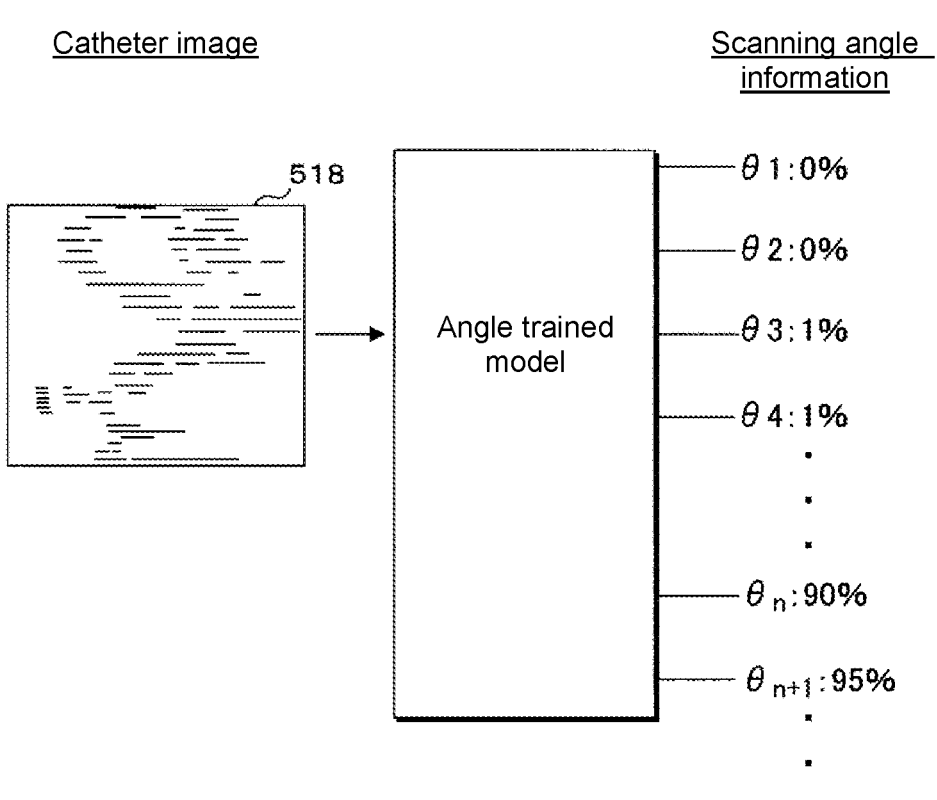
FIG. 15 is an explanatory view explaining a configuration of an angle trained model.

FIG. 15 is an explanatory view explaining the configuration of an angle trained model 612. The angle trained model 612 is a model that receives the catheter image 51 and outputs the scanning angle information regarding the scanning angle at which the medical instrument is visualized.

FIG. 15 schematically illustrates the angle trained model 612 that receives the RT format catheter image 518 and outputs the scanning angle information indicating the probability that the medical instrument is visualized at each scanning angle, that is, in the longitudinal direction of the RT format catheter image 518. Since the medical instrument is visualized over a plurality of scanning angles, the total probability of outputting the scanning angle information exceeds 100%. The angle trained model 612 may extract and output an angle having a relatively high probability that the medical instrument is visualized.

The angle trained model 612 is generated by machine learning. By extracting the scanning angle of the position information from the position information field of the medical instrument position training data DB 71 described with reference to FIG. 9, the scanning angle can be used for training data for generating the angle trained model 612.

The outline of the processing of generating the angle trained model 612 will be described using the flowchart of FIG. 12. Prior to the execution of the program of FIG. 12, an untrained model such as a CNN or the like in which, for example, a convolution layer, a pooling layer, and a fully connected layer are combined is prepared. Each parameter of the prepared model is adjusted by the program of FIG. 12, and machine learning is performed.

The control unit 21 acquires a training record used for training of one epoch from the medical instrument position training data DB 71 (S571). As described above, the training record recorded in the medical instrument position training data DB 71 is a combination of the RT format catheter image 518 and the coordinates indicating the position of the medical instrument visualized in the RT format catheter image 518.

When the RT format catheter image 518 is input to the input layer of the model, the control unit 21 adjusts the parameter of the model so that the scanning angle corresponding to the position information is output from the output layer (S572). In the acquisition of the training record and the parameter adjustment of the model, the program may appropriately have a function of causing the control unit 21 to execute reception of correction by the user, presentation of a basis of determination, additional learning, and the like.

The control unit 21 determines whether or not to end the processing (S573). For example, when ending the learning of the predetermined number of epochs, the control unit 21 determines to finish the processing. The control unit 21 may acquire test data from the medical instrument position training data DB 71, input the test data to the model under machine learning, and determine to end the processing in a case where an output with predetermined accuracy is obtained.

When determining not to end the processing (NO in S573), the control unit 21 returns to S571. When determining to end the processing (YES in S573), the control unit 21 records, in the auxiliary storage device 23, the parameter of the trained medical instrument position training data DB 71 (S574). Thereafter, the control unit 21 ends the processing. By the above processing, the angle trained model 612 that receives the catheter image 51 and outputs the information regarding the scanning angle can be generated.

Prior to the execution of the program of FIG. 12, a model that receives time-series input such as RNN may be prepared. The RNN can be, for example, an LSTM. In S572, when the plurality of RT format catheter images 518 captured in time series is input to the input layer of the model, the control unit 21 adjusts the parameter of the model so that the information regarding the scanning angle associated with the final RT format catheter image 518 is output in time series from the output layer.

Instead of using the angle trained model 612, the control unit 21 may determine the scanning angle at which the medical instrument is visualized by pattern matching.

Figure 16:
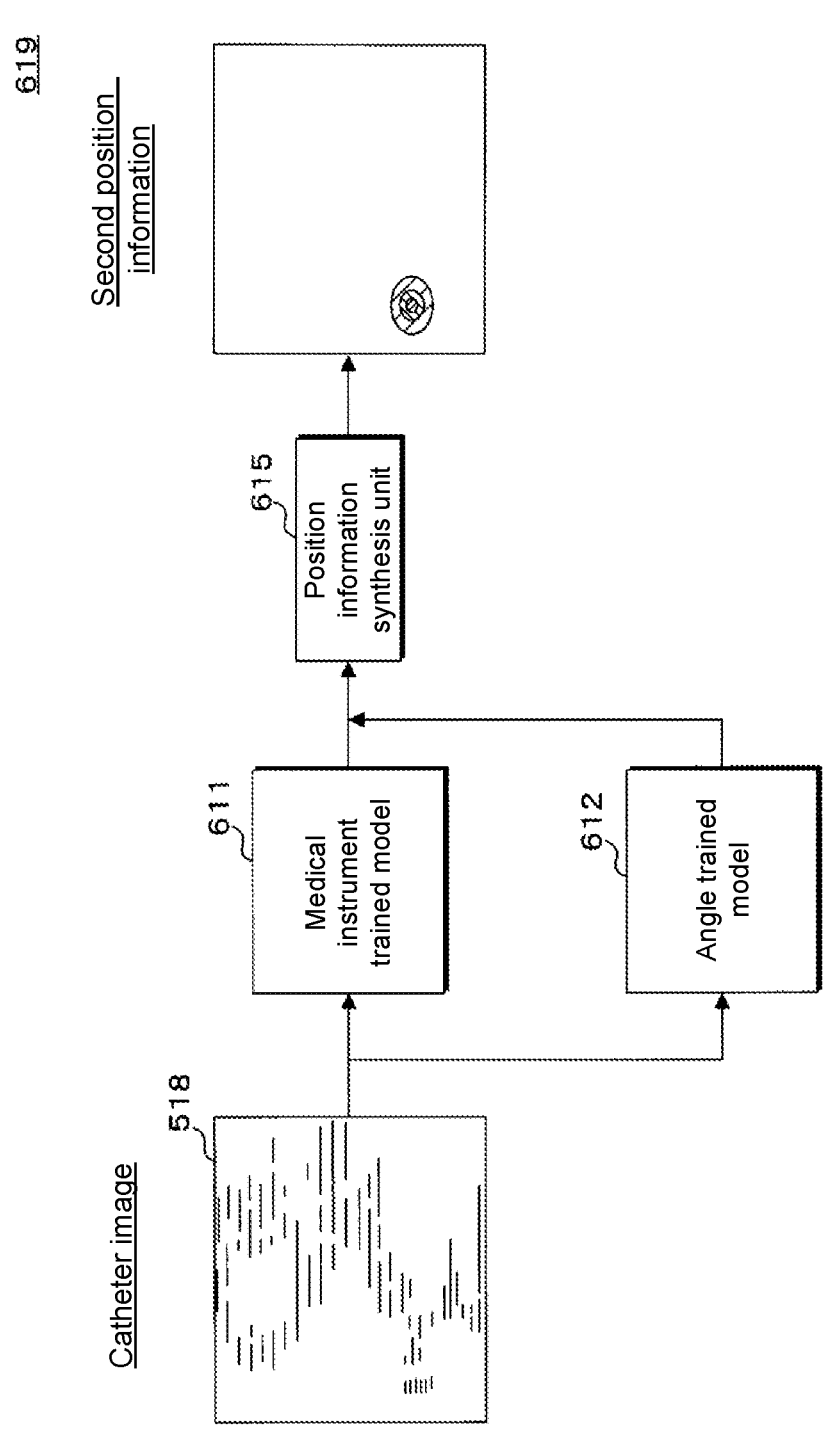
FIG. 16 is an explanatory view explaining a position information model.

FIG. 16 is an explanatory view explaining a position information model 619. The position information model 619 is a model that receives the RT format catheter image 518 and outputs the second position information indicating the position of the medical instrument being visualized. The position information model 619 includes the medical instrument trained model 611, the angle trained model 612, and a position information synthesis unit 615.

The same RT format catheter image 518 is input to both the medical instrument trained model 611 and the angle trained model 612. The first position information is output from the medical instrument trained model 611. As described with reference to FIG. 6, the first position information is a probability that the medical instrument is visualized at each site on the RT format catheter image 518. In the following description, the probability that the medical instrument is visualized at the position where the distance from the center of the image acquisition catheter 40 is r and the scanning angle is θ is indicated by P1 (r, θ).

The scanning angle information is output from the angle trained model 612. The scanning angle information is a probability that the medical instrument is visualized at each scanning angle. In the following description, the probability that the medical instrument is visualized in the direction of the scanning angle θ is indicated by Pt (θ).

The position information synthesis unit 615 synthesizes the first position information and the scanning angle information to generate the second position information. Similarly to the first position information, the second position information is a probability that the medical instrument is visualized at each site on the RT format catheter image 518. The input end of the position information synthesis unit 615 functions as a first position information acquisition unit and functions as a scanning angle information acquisition unit.

Since the medical instrument is visualized in the RT format catheter image 518 as a reason having a certain amount of area, both the sum of P1 and the sum of Pt may be larger than 1. The second position information P2 (r, θ) at the position where the distance from the center of the image acquisition catheter 40 is r and the scanning angle is θ is calculated by, for example, Expression (1-1).

$$P2(r,\theta)=P1(r,\theta)+kPt(\theta) \qquad (1\text{-}1)$$

k is a coefficient related to weighting between the first position information and the scanning angle information.

The second position information P2 (r, θ) may be calculated by Expression (1-2).

$$P2(r,\theta)=P1(r,\theta)\times Pt(\theta) \qquad (1\text{-}2)$$

The second position information P2 (r, θ) may be calculated by Expression (1-3). Expression (1-3) is an expression for calculating an average value of the first position information and the scanning angle information.

$$P2(r,\theta)=(P1(r,\theta)+Pt(\theta))/2 \qquad (1\text{-}3)$$

Each of the second position information P2 (r, θ) in Expressions (1-1) to (1-3) is not a probability but a numerical value relatively indicating the magnitude of the possibility that the medical instrument is visualized. By synthesizing the first position information and the scanning angle information, accuracy in the scanning angle direction can be improved. The second position information may be information regarding a position where the value of P2 (r, θ) is the largest. The second position information may be determined by a function other than the expressions exemplified in Expressions (1-1) to (1-3).

The second position information is an example of the position information of the medical instrument acquired in S502 described with reference to FIG. 4. The medical instrument trained model 611, the angle trained model 612, and the position information synthesis unit 615 cooperate to implement S502 described with reference to FIG. 4. The output end of the position information synthesis unit 615 functions as the second position information output unit that outputs the second position information on the basis of the first position information and the scanning angle information.

Figure 17:
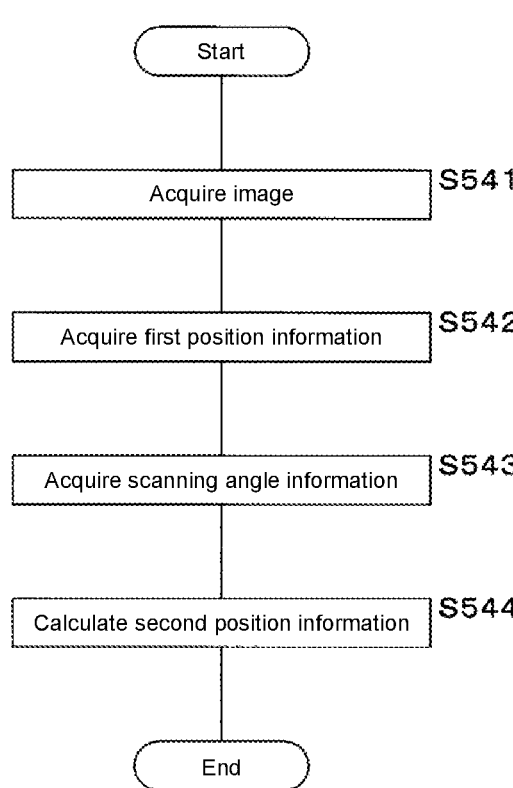
FIG. 17 is a flowchart explaining a flow of processing of a program of a third embodiment.

FIG. 17 is a flowchart explaining a flow of the processing of the program of the third embodiment. The flowchart described with reference to FIG. 17 illustrates details of the processing in S502 described with reference to FIG. 4.

The control unit 21 acquires one frame of the RT format catheter image 518 (S541). The control unit 21 inputs the RT format catheter image 518 to the medical instrument trained model 611 and acquires the first position information (S542). The control unit 21 inputs the RT format catheter image 518 to the angle trained model 612 and acquires the scanning angle information (S543).

The control unit 21 calculates the second position information on the basis of, for example, Expression (1-1) or Expression (1-2) (S544). Thereafter, the control unit 21 ends the processing. Thereafter, the control unit 21 uses, as the position information in S502, the second position information calculated in S544.

According to the present embodiment, it is possible to provide the catheter system 10 that accurately calculates the position information of the medical instrument visualized in the catheter image 51.

Fourth Embodiment

Figure 18:
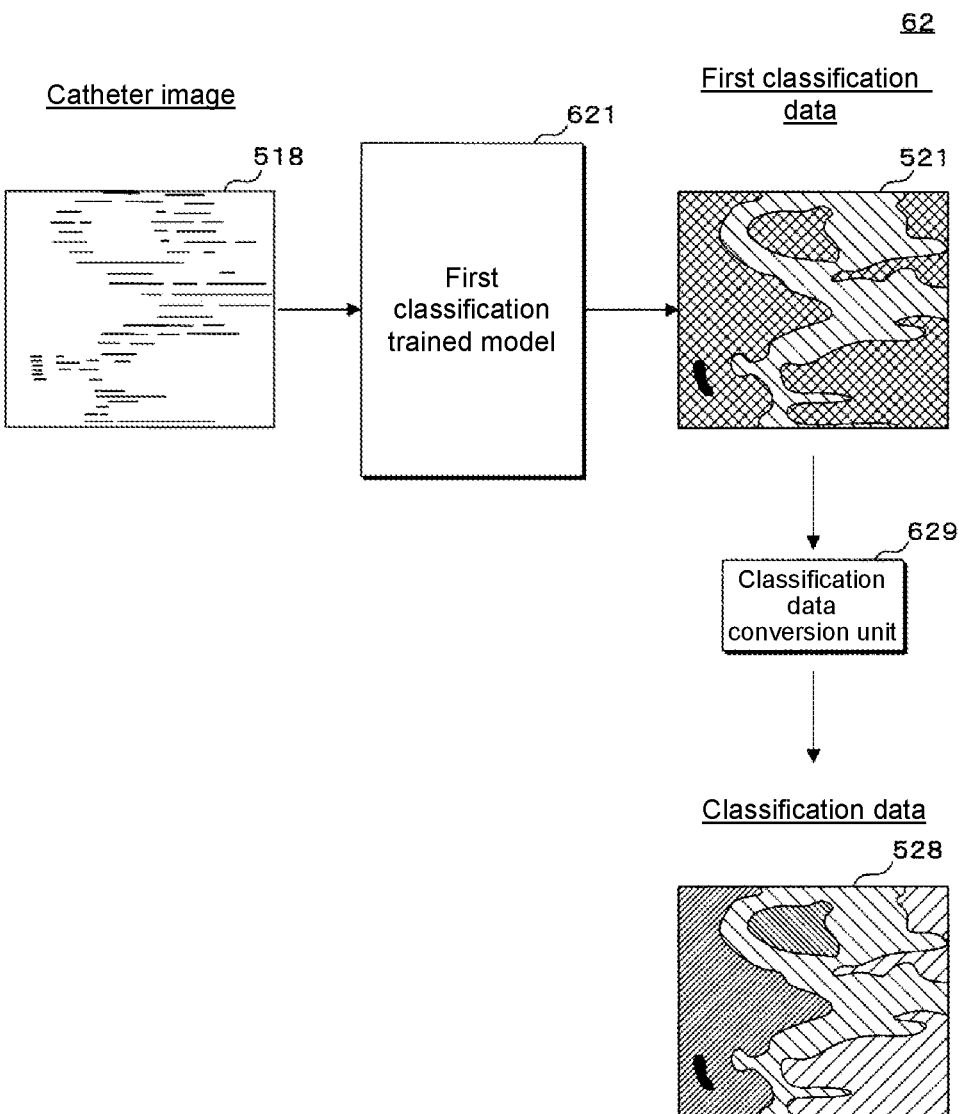
FIG. 18 is an explanatory view explaining a configuration of a classification model.

The present embodiment relates to a specific example of the classification model 62 described with reference to FIG. 7. FIG. 18 is an explanatory view explaining the configuration of the classification model 62. The classification model 62 includes a first classification trained model 621 and a classification data conversion unit 629.

The first classification trained model 621 receives the RT format catheter image 518 and outputs first classification data 521 classified into the "biological tissue region", the "non-biological tissue region", and the "medical instrument region" for each portion constituting the RT format catheter image 518. The first classification trained model 621 further outputs the reliability of the classification result for each portion, that is, the probability that the classification result is correct. The output layer of the first classification trained model 621 functions as the first classification data output unit that outputs the first classification data 521.

The upper right view of FIG. 18 schematically illustrates the first classification data 521 in the RT format. Thick right-downward hatching indicates biological tissue regions such as the atrial wall and the ventricular wall. Black indicates a medical instrument region in which a medical instrument such as a Brockenbrough needle is visualized. The lattice-like hatching indicates a non-biological tissue region that is neither a medical instrument region nor a biological tissue region.

The first classification data 521 is converted into the classification data 52 by the classification data conversion unit 629. The lower right view of FIG. 18 schematically illustrates the RT format classification data 528. The non-biological tissue region is classified into three types, the first inner cavity region, the second inner cavity region, and the non-inner cavity region. Similarly to FIG. 5C, the thin left-downward hatching indicates the first inner cavity region. The thin right-downward hatching indicates the second inner cavity region. The thick left-downward hatching indicates the non-inner cavity region.

An outline of the processing performed by the classification data conversion unit 629 will be described. Of the non-biological tissue region, a region in contact with the image acquisition catheter 40, that is, the rightmost region in the first classification data 521 is classified as the first inner cavity region. In the non-biological tissue region, a region surrounded by the biological tissue region is classified into the second inner cavity region. The classification of the second inner cavity region is desirably determined in a state where the upper end and the lower end of the RT format catheter image 518 are connected to form a cylindrical shape. A region that is neither the first inner cavity region nor the second inner cavity region of the non-biological tissue region is classified as the non-inner cavity region.

FIG. 19 is an explanatory view explaining the first training data. The first training data is used when the first classification trained model 621 is generated by machine learning. In the following description, a case where the first training data is created using the information processing device 20 described with reference to FIG. 3 will be described as an example. The first training data may be created using a computer or the like different from the information processing device 20.

The control unit 21 displays two types of the catheter images 51 of the RT format catheter image 518 and the XY format catheter image 519 on the display device 31. The labeler observes the displayed catheter image 51 and performs marking on four types of boundary line data of a "boundary line between the first inner cavity region and the biological tissue region", a "boundary line between the second inner cavity region and the biological tissue region", a "boundary line between the non-inner cavity region and the biological tissue region", and a "visible outline of the medical instrument region".

The labeler may perform marking on the catheter image 51 of either of the RT format catheter image 518 and the XY format catheter image 519. The control unit 21 displays a boundary line corresponding to the marking at a corresponding position in the other catheter image 51. As described above, the labeler can check both the RT format catheter image 518 and the XY format catheter image 519 and perform appropriate marking.

The labeler inputs which of the "biological tissue region", the "non-biological tissue region", and the "medical instrument region" each region divided by the four types of marked boundary line data is. The control unit 21 may automatically determine the region, and the labeler may issue a correction instruction as necessary. By the above processing, the first classification data 521 clearly indicating which of the "biological tissue region", the "non-biological tissue region", and the "medical instrument region" each region of the catheter image 51 is classified into is created.

The first classification data 521 will be described with a specific example. A "biological tissue region label" is recorded in a pixel classified into the "biological tissue region", a "first inner cavity region label" is recorded in a pixel classified into the "first inner cavity region", a "second inner cavity region label" is recorded in a pixel classified into the "second inner cavity region", a "non-inner cavity region label" is recorded in a pixel classified into the "non-inner cavity region", a "medical instrument region label" is recorded in a pixel classified into the "medical instrument region", and a "non-biological tissue region label" is recorded in a pixel classified into the "non-biological tissue region". Each label is indicated by an integer, for example. The first classification data 521 is an example of label data in which position of a pixel is associated with a label.

The control unit 21 records the catheter image 51 and the first classification data 521 in association with each other. A first training data DB is created by repeating the above processing and recording a large number of sets of data. In the following description, the first training data DB in which the RT format catheter image 518 and the first classification data 521 in the RT format are recorded in association with each other in the first training data DB will be described as an example.

The control unit 21 may generate the XY format classification data 529 on the basis of the XY format catheter image 519. The control unit 21 may generate the RT format classification data 528 on the basis of the XY format classification data 529.

The outline of the processing of generating the first classification trained model 621 will be described using the flowchart of FIG. 12. Prior to the execution of the program of FIG. 12, an untrained model such as a U-Net structure that implements, for example, semantic segmentation is prepared.

The U-Net structure includes a multi-layer encoder layer and a multi-layer decoder layer connected to the rear of the multi-layer encoder layer. Each encoder layer includes a pooling layer and a convolution layer. By semantic segmentation, a label is given to each pixel constituting an input image. The untrained model may be a Mask R-CNN model or a model that implements segmentation of another optional image.

The control unit 21 acquires a training record used for training of one epoch from the first training data DB (S571). When the RT format catheter image 518 is input to the input layer of the model, the control unit 21 adjusts the parameter of the model so that the first classification data 521 in the RT format is output from the output layer (S572). In the acquisition of the training record and the parameter adjustment of the model, the program may appropriately have a function of causing the control unit 21 to execute reception of correction by the user, presentation of a basis of determination, additional learning, and the like.

The control unit 21 determines whether or not to end the processing (S573). For example, when ending the learning of the predetermined number of epochs, the control unit 21 determines to finish the processing. The control unit 21 may acquire test data from the first training data DB, input the test data to the model under machine learning, and determine to end the processing when an output with predetermined accuracy is obtained.

When determining not to end the processing (NO in S573), the control unit 21 returns to S571. When determining to end the processing (YES in S573), the control unit 21 records the parameter of the trained first classification trained model 621 in the auxiliary storage device 23 (S574). Thereafter, the control unit 21 ends the processing. By the above processing, the first classification trained model 621 that receives the catheter image 51 and outputs the first classification data 521 is generated.

Prior to the execution of the program of FIG. 12, a model that receives time-series input may be prepared. The model that receives the time-series input includes a memory portion that holds information regarding the RT format catheter image 518 input in the past, for example. The model that receives the time-series input may include a recursive input portion that inputs, together with the next RT format catheter image 518, an output to the RT format catheter image 518 input in the past.

Use of the catheter images 51 acquired in time series makes it possible to implement the first classification trained model 621 that is hardly affected by image noise or the like and outputs the first classification data 521 with relatively high accuracy.

The first classification trained model 621 may be created using a computer or the like different from the information processing device 20. The first classification trained model 621 on which the machine learning is completed may be copied to the auxiliary storage device 23 via the network. The first classification trained model 621 trained by one piece of hardware can be used by the plurality of information processing devices 20.

Figure 20:
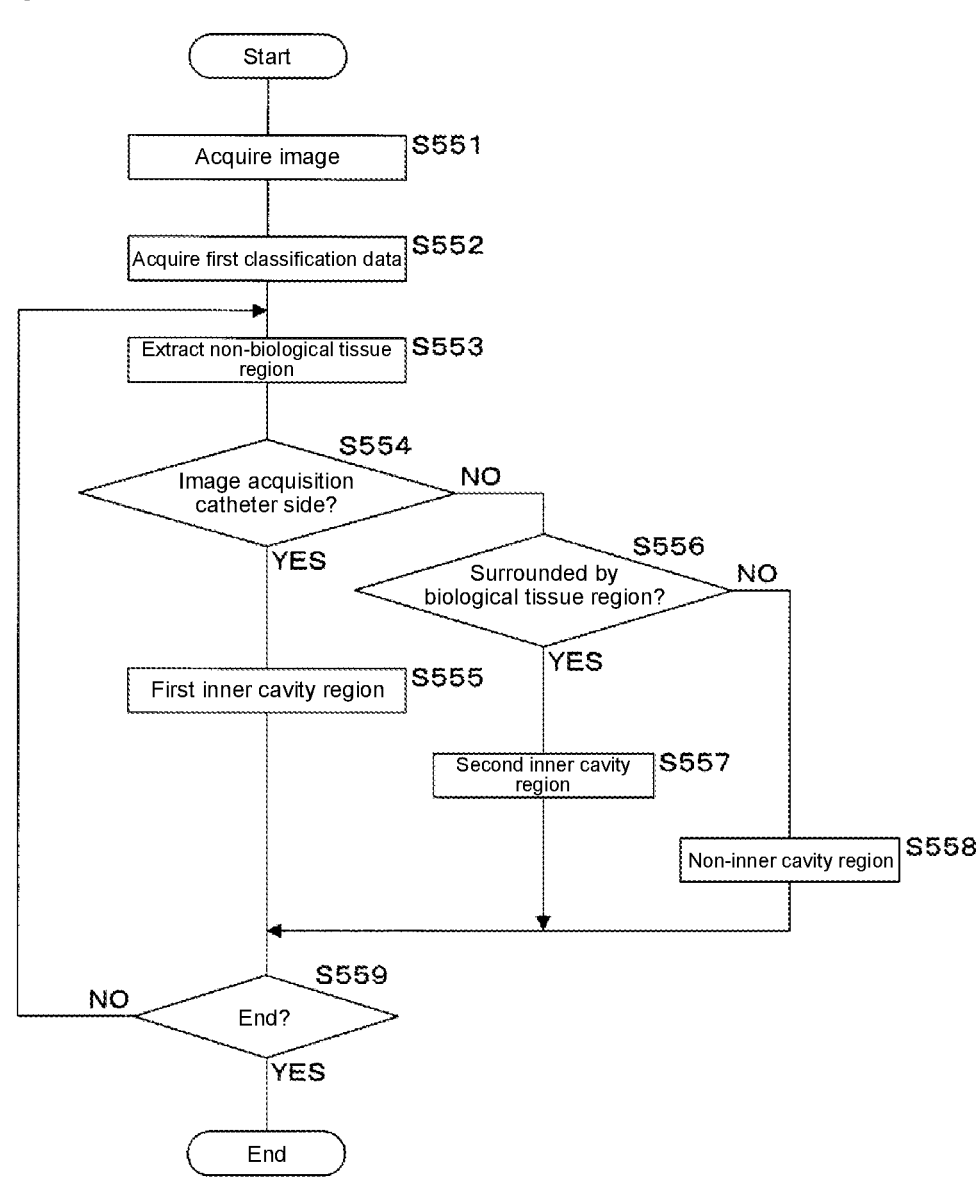
FIG. 20 is a flowchart explaining a flow of processing of a program of a fourth embodiment.

FIG. 20 is a flowchart explaining a flow of the processing of the program of the fourth embodiment. The flowchart described with reference to FIG. 20 illustrates details of the processing performed by the classification model 62 described with reference to FIG. 7.

The control unit 21 acquires one frame of the RT format catheter image 518 (S551). The control unit 21 inputs the RT format catheter image 518 to the first classification trained model 621 and acquires the first classification data 521 (S552). The control unit 21 extracts one continuous non-biological tissue region from the first classification data 521 (S553). The processing on and after the extraction of the non-biological tissue region is desirably performed in a state where the upper end and the lower end of the RT format catheter image 518 are connected to form a cylindrical shape.

The control unit 21 determines whether or not the non-biological tissue region extracted in S552 is on a side in contact with the image acquisition catheter 40, that is, a part in contact with the left end of the RT format catheter image 518 (S554). When determining that the non-biological tissue region is on the side in contact with the image acquisition catheter 40 (YES in S554), the control unit 21 determines that the non-biological tissue region extracted in S553 is the first inner cavity region (S555).

When determining that the non-biological tissue region is not a part in contact with the image acquisition catheter 40 (NO in S554), the control unit 21 determines whether or not the non-biological tissue region extracted in S552 is surrounded by the biological tissue region (S556). When determining that the non-biological tissue region is surrounded by the biological tissue region (YES in S556), the control unit 21 determines that the non-biological tissue region extracted in S553 is the second inner cavity region (S557). By S555 and S557, the control unit 21 implements the function of an inner cavity region extraction unit.

When determining that the non-biological tissue region is not surrounded by the biological tissue region (NO in S556), the control unit 21 determines that the non-biological tissue region extracted in S553 is the non-inner cavity region (S558).

After ending of S555, S557, or S558, the control unit 21 determines whether or not to have ended the processing of all non-biological tissue regions (S559). When determining not to have ended the processing (NO in S559), the control unit 21 returns to S553. When determining that the processing has ended (YES in S559), the control unit 21 ends the processing.

The control unit 21 implements the function of the classification data conversion unit 629 by the processing from S553 to S559.

The first classification trained model 621 may be a model that classifies the XY format catheter image 519 into a biological tissue region, a non-biological tissue region, and a medical instrument region. The first classification trained model 621 may be a model that classifies the RT format catheter image 518 into the biological tissue region and the non-biological tissue region. In such a case, the labeler needs not perform marking on the medical instrument region.

According to the present embodiment, it is possible to generate the first classification trained model 621 that classifies the catheter image 51 into the biological tissue region, the non-biological tissue region, and the medical instrument region. According to the present embodiment, it is possible to provide the catheter system 10 that generates the classification data 52 using the generated first classification trained model 621.

Modification 4-1

The labeler may input which of the "biological tissue region", the "first inner cavity region", the "second inner cavity region", the "non-inner cavity region", and the "medical instrument region" each region divided by the four types of boundary line data having been marked. By performing machine learning using the first training data DB created in this manner, it is possible to generate the first classification trained model 621 that classifies the catheter image 51 into the "biological tissue region", the "first inner cavity region", the "second inner cavity region", the "non-inner cavity region", and the "medical instrument region".

As described above, it is possible to implement the classification model 62 that classifies the catheter image 51 into the "biological tissue region", the "first inner cavity region", the "second inner cavity region", the "non-inner cavity region", and the "medical instrument region" without using the classification data conversion unit 629.

Fifth Embodiment

The present embodiment relates to the catheter system 10 using a synthesis classification model 626 that synthesizes the classification data 52 output from each of the two classification trained models. Description of parts common to the fourth embodiment will be omitted.

Figure 21:
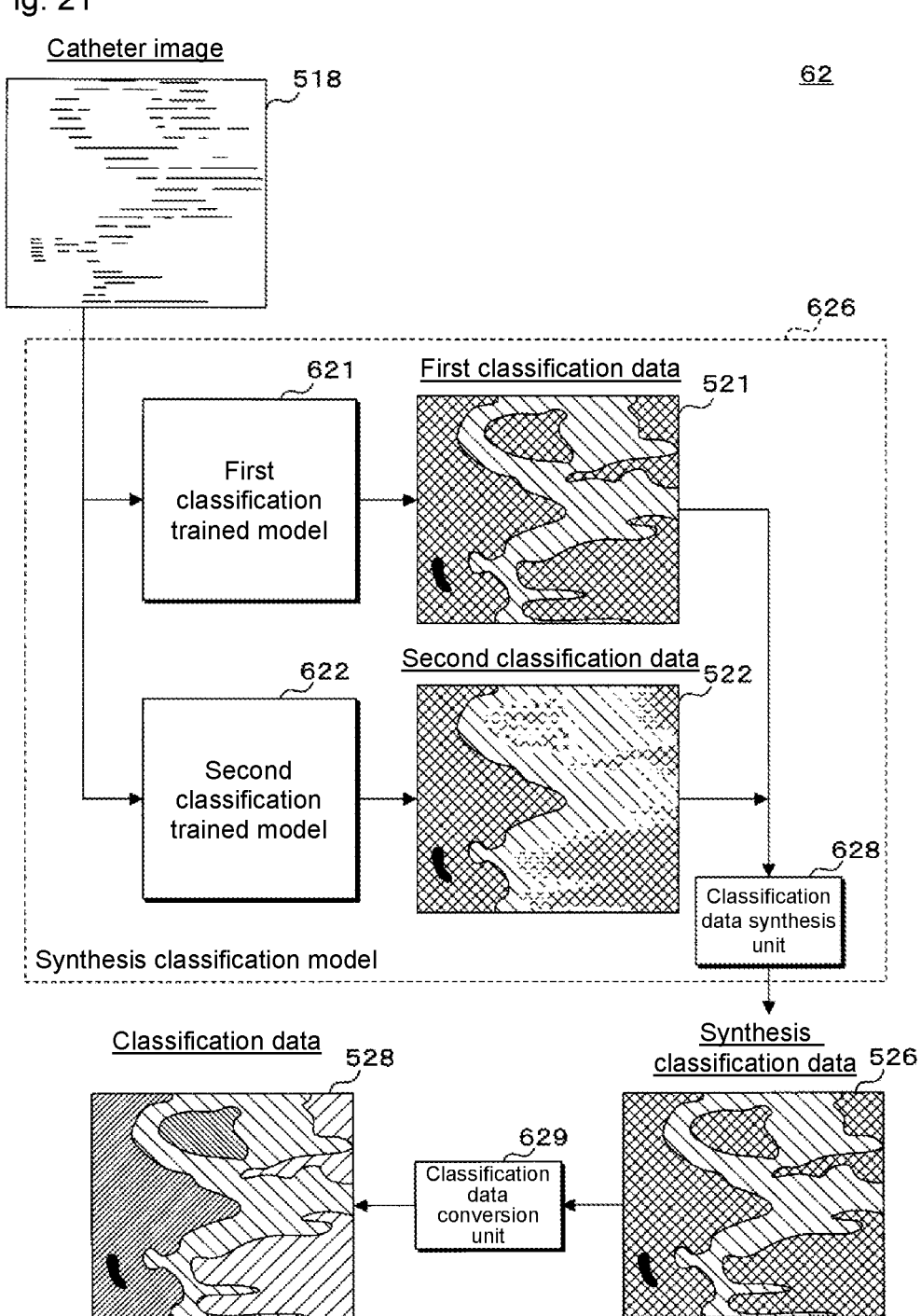
FIG. 21 is an explanatory view explaining a configuration of a classification model of a fifth embodiment.

FIG. 21 is an explanatory view explaining the configuration of the classification model 62 of the fifth embodiment. The classification model 62 includes the synthesis classification model 626 and the classification data conversion unit 629. The synthesis classification model 626 includes the first classification trained model 621, a second classification trained model 622, and a classification data synthesis unit 628. Since the first classification trained model 621 is similar to that of the fourth embodiment, the description of the first classification trained model 621 will be omitted.

The second classification trained model 622 is a model that receives the RT format catheter image 518 and outputs the second classification data 522 classified into the "biological tissue region", the "non-biological tissue region", and the "medical instrument region" for each portion constituting the RT format catheter image 518. The second classification trained model 622 further outputs the reliability of the classification result for each portion, that is, the probability that the classification result is correct. Details of the second classification trained model 622 will be described later.

The classification data synthesis unit 628 synthesizes the first classification data 521 and the second classification data 522 to generate synthesis classification data 526. That is, the input end of the classification data synthesis unit 628 implements the functions of a first classification data acquisition unit and a second classification data acquisition unit. The output end of the classification data synthesis unit 628 implements the function of a synthesis classification data output unit.

Details of the synthesis classification data 526 will be described later. The synthesis classification data 526 is converted into classification data 52 by the classification data conversion unit 629. Since the processing performed by the classification data conversion unit 629 is similar to that of the fourth embodiment, the description of the classification data conversion 629 will be omitted.

FIG. 22 is an explanatory view explaining the second training data. The second training data is used when the second classification trained model 622 is generated by machine learning. In the following description, a case where the second training data is created using the information processing device 20 described with reference to FIG. 3 will be described as an example. The second training data may be created using a computer or the like different from the information processing device 20.

The control unit 21 displays two types of the catheter images 51 of the RT format catheter image 518 and the XY format catheter image 519 on the display device 31. The labeler observes the displayed catheter image 51 and performs marking on two types of boundary line data of the "boundary line between the first inner cavity region and the biological tissue region" and the "visible outline of the medical instrument region".

The labeler may perform marking on the catheter image 51 of either of the RT format catheter image 518 and the XY format catheter image 519. The control unit 21 displays a boundary line corresponding to the marking at a corresponding position in the other catheter image 51. As described above, the labeler can check both the RT format catheter image 518 and the XY format catheter image 519 and perform appropriate marking.

The labeler inputs which of the "biological tissue region", the "non-biological tissue region", and the "medical instrument region" each region divided by the two types of marked boundary line data is. The control unit 21 may automatically determine the region, and the labeler may issue a correction instruction as necessary. By the above processing, the second classification data 522 clearly indicating which region of the "biological tissue region", the "non-biological tissue region", and the "medical instrument region" each portion of the catheter image 51 is classified into is created.

The second classification data 522 will be described with a specific example. A "biological tissue region label" is recorded in a pixel classified into the "biological tissue region", a "non-biological tissue region label" is recorded in a pixel classified into the "non-biological tissue region", and a "medical instrument region label" is recorded in a pixel classified into the "medical instrument region". Each label is indicated by an integer, for example. The second classification data 522 is an example of label data in which position of a pixel is associated with a label.

The control unit 21 records the catheter image 51 and the second classification data 522 in association with each other. A second training data DB is created by repeating the above processing and recording a large number of sets of data. The second classification trained model 622 can be generated by performing processing similar to the machine learning described in the fourth embodiment using the second training data DB.

The second classification trained model 622 may be a model that classifies the XY format catheter image 519 into the biological tissue region, the non-biological tissue region, and the medical instrument region. The second classification trained model 622 may be a model that classifies the RT format catheter image 518 into the biological tissue region and the non-biological tissue region. In such a case, the labeler needs not perform marking on the medical instrument region.

Creation of the second classification data 522 can be performed in a shorter time than creation of the first classification data 521. The labeler training for creating the second classification data 522 can be performed in a shorter time than the labeler training for creating the first classification data 521. As described above, a larger amount of training data can be registered in the second training data DB than in the first training data DB.

Since a large amount of training data can be used, the second classification trained model 622 that can identify the boundary between the first inner cavity region and the biological tissue region and the outer shape of the medical instrument region with relatively higher accuracy than the first classification trained model 621 can be generated. However, since the second classification trained model 622 does not train a non-biological tissue region other than the first inner cavity region, it is not possible to identify the non-biological tissue region from the biological tissue region.

The processing performed by the classification data synthesis unit 628 will be described. The same RT format catheter image 518 is input to both the first classification trained model 621 and the second classification trained model 622. The first classification data 521 is output from the medical instrument trained model 611. The second classification data 522 is output from the second classification trained model 622.

In the following description, a case where the classified label and the reliability of the label are output for each pixel of the RT format catheter image 518 in both the first classification trained model 621 and the second classification trained model 622 will be described as an example. The first classification trained model 621 and the second classification trained model 622 may output a label and a probability classified for each range of a total of 9 pixels including 3 vertical pixels and 3 horizontal pixels of the RT format catheter image 518, for example.

For a pixel whose distance from the center of the image acquisition catheter 40 is r and whose scanning angle is $\theta$, the reliability that the first classification trained model 621 is a biological tissue region is indicated by $Q1t(r, \theta)$. For a pixel classified into a region other than the biological tissue region by the first classification trained model 621, $Q1t(r, \theta) = 0$.

Similarly, for a pixel whose distance from the center of the image acquisition catheter 40 is r and whose scanning angle is $\theta$, the reliability that the second classification trained model 622 is a biological tissue region is indicated by $Q2t(r, \theta)$. For a pixel classified into a region other than the biological tissue region by the second classification trained model 622, Q2$t$ (r, θ)=0.

The classification data synthesis unit 628 calculates a synthesis value Qt (r, θ) on the basis of, for example, Expression (5-1). Qt (r, θ) is not a correct probability of the classification into the biological tissue region, but is a numerical value relatively indicating the magnitude of the reliability of being the biological tissue region.

$$Qt(r,\theta)=Q1t(r,\theta)\times Q2t(r,\theta) \tag{5-1}$$

The classification data synthesis unit 628 classifies a pixel having Qt (r, θ) of 0.5 or more into the biological tissue region.

Similarly, the reliability that the first classification trained model 621 is the medical instrument region is indicated by Q1$c$ (r, θ), and the reliability that the second classification trained model 622 is the medical instrument region is indicated by Q2$c$ (r, θ).

The classification data synthesis unit 628 calculates a synthesis value Qc (r, θ) on the basis of, for example, Expression (5-2). Qc (r, θ) is not a correct probability of the classification into the medical instrument region, but is a numerical value relatively indicating the magnitude of the reliability of being the medical instrument region.

$$Qc(r,\theta)=Q1c(r,\theta)\times Q2c(r,\theta) \tag{5-2}$$

The classification data synthesis unit 628 classifies a pixel having Qc (r, θ) of 0.5 or more into the medical instrument region. The classification data synthesis unit 628 classifies a pixel that has been classified into neither the medical instrument region nor the biological tissue region into the non-biological tissue region. As described above, the classification data synthesis unit 628 generates the synthesis classification data 526 in which the first classification data 521 and the second classification data 522 are synthesized. The synthesis classification data 526 is converted into the RT format classification data 528 by the classification data conversion unit 629.

Expressions (5-1) and (5-2) are examples. The threshold when the classification data synthesis unit 628 performs classification is also an example. The classification data synthesis unit 628 may be a trained model that receives the first classification data 521 and the second classification data 522 and outputs the synthesis classification data 526.

The first classification data 521 may be input to the classification data synthesis unit 628 after being classified into the "biological tissue region", the "first inner cavity region", the "second inner cavity region", the "non-inner cavity region", and the "medical instrument region" by the classification data conversion unit 629 described in the fourth embodiment.

The first classification trained model 621 may be a model that classifies the catheter image 51 described in the modification 4-1 into the "biological tissue region", the "first inner cavity region", the "second inner cavity region", the "non-inner cavity region", and the "medical instrument region".

When data in which the non-biological tissue region is classified into the "first inner cavity region", the "second inner cavity region", and the "non-inner cavity region" is input to the classification data synthesis unit 628, the classification data synthesis unit 628 can output the synthesis classification data 526 classified into the "biological tissue region", the "first inner cavity region", the "second inner cavity region", the "non-inner cavity region", and the "medical instrument region". In such a case, it is not necessary to input the synthesis classification data 526 to the classification data conversion unit 629 to convert the synthesis classification data into the RT format classification data 528.

Figure 23:
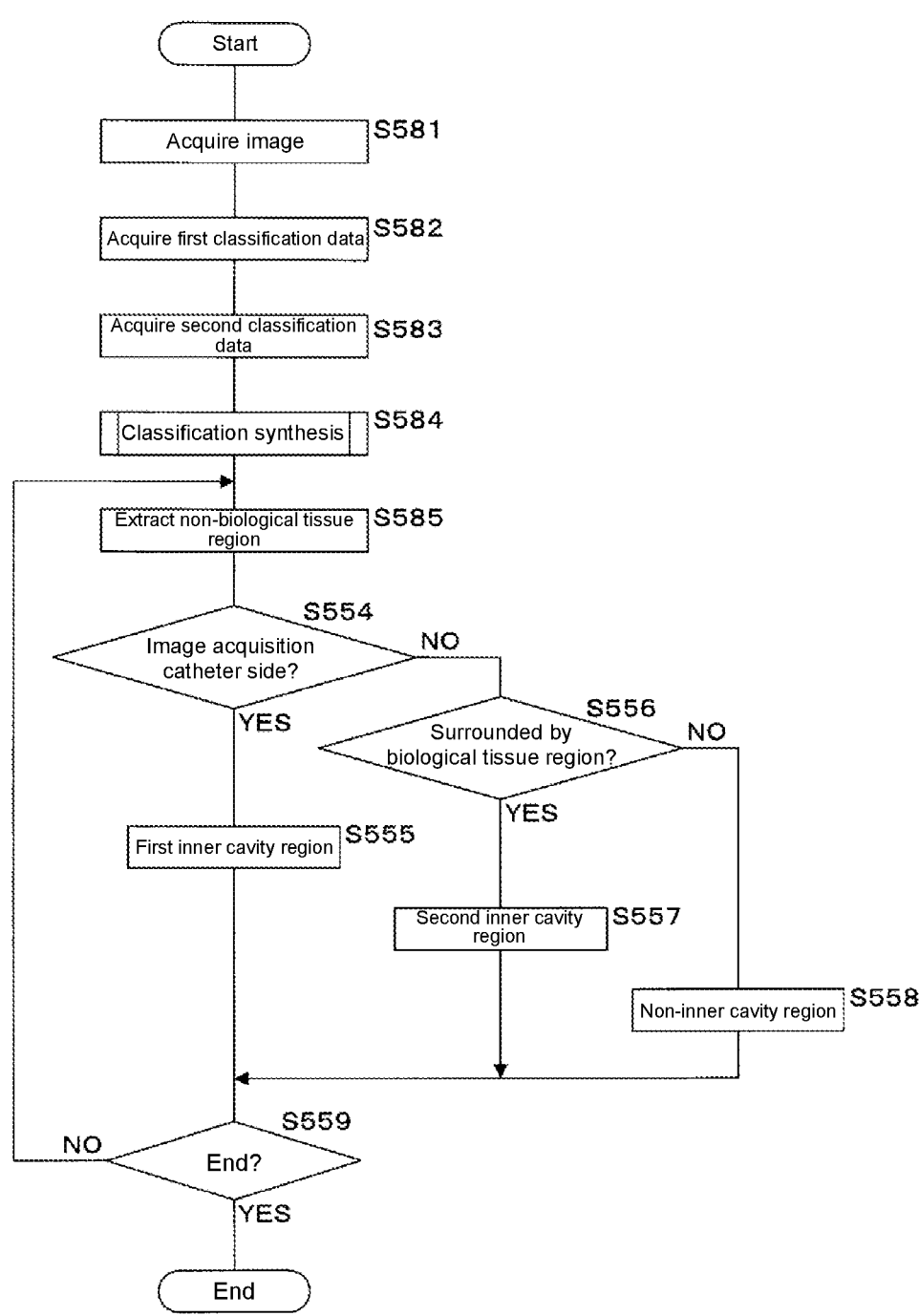
FIG. 23 is a flowchart explaining a flow of processing of a program of the fifth embodiment.

FIG. 23 is a flowchart explaining a flow of the processing of the program of the fifth embodiment. The flowchart described with reference to FIG. 23 illustrates details of the processing performed by the classification model 62 described with reference to FIG. 7.

The control unit 21 acquires one frame of the RT format catheter image 518 (S581). By S581, the control unit 21 implements the function of the image acquisition unit. The control unit 21 inputs the RT format catheter image 518 to the first classification trained model 621 and acquires the first classification data 521 (S582). The control unit 21 inputs the RT format catheter image 518 to the second classification trained model 622 and acquires the second classification data 522 (S583).

The control unit 21 starts a classification synthesis subroutine (S584). The classification synthesis subroutine is a subroutine that synthesizes first classification data 521 and second classification data 522 to generate the synthesis classification data 526. The flow of processing of the classification synthesis subroutine will be described later.

The control unit 21 extracts one continuous non-biological tissue region from the synthesis classification data 526 (S585). The processing on and after the extraction of the non-biological tissue region is desirably performed in a state where the upper end and the lower end of the RT format catheter image 518 are connected to form a cylindrical shape.

The control unit 21 determines whether or not the non-biological tissue region extracted in S585 is on a side in contact with the image acquisition catheter 40 (S554). The processing up to S559 is the same as the processing flow of the program of the fourth embodiment described with reference to FIG. 20, and thus the description of the processing up to S559 is omitted.

The control unit 21 determines whether or not to have ended the processing of all non-biological tissue regions (S559). When determining not to have ended the processing (NO in S559), the control unit 21 returns to S585. When determining that the processing has ended (YES in S559), the control unit 21 ends the processing.

Figure 24:
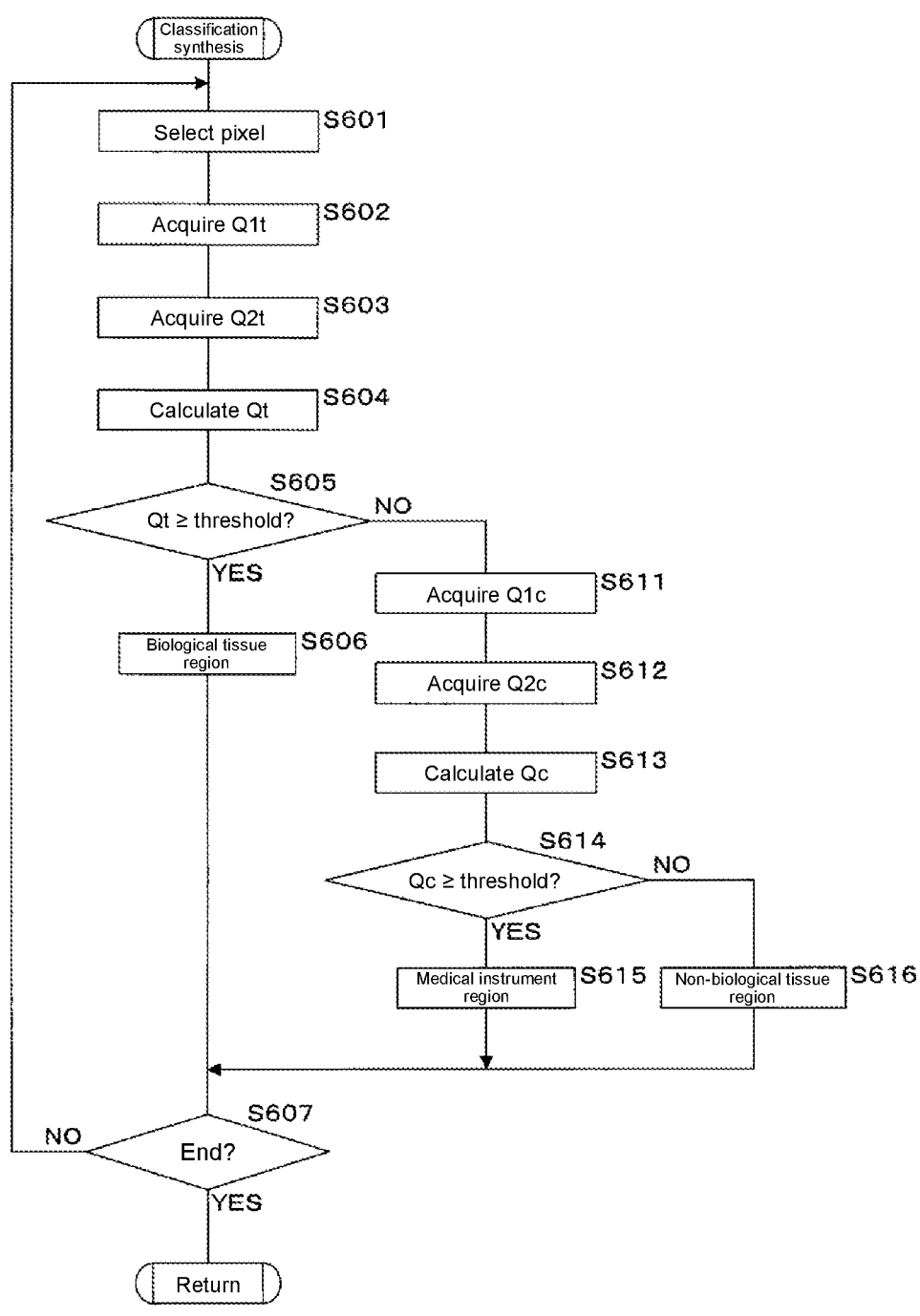
FIG. 24 is a flowchart explaining a flow of processing of a subroutine of classification synthesis.

FIG. 24 is a flowchart explaining a flow of the processing of a subroutine of classification synthesis. The classification synthesis subroutine is a subroutine that synthesizes first classification data 521 and second classification data 522 to generate the synthesis classification data 526.

The control unit 21 selects a pixel to be processed (S601). The control unit 21 acquires a reliability Q1$t$ (r, θ) that the pixel being processed is in the biological tissue region from the first classification data 521 (S602). The control unit 21 acquires a reliability Q2$t$ (r, θ) that the pixel being processed is in the biological tissue region from the second classification data 522 (S603).

The control unit 21 calculates the synthesis value Qt (r, θ) on the basis of, for example, Expression (5-1) (S604). The control unit 21 determines whether or not the synthesis value Qt (r, θ) is equal to or greater than a predetermined threshold (S605). The predetermined threshold can be, for example, 0.5.

When determining that the synthesis value is equal to or greater than the predetermined threshold (YES in S605), the control unit 21 classifies the pixel being processed into the "biological tissue region" (S606). When determining that the synthesis value is less than the predetermined threshold (NO in S605), the control unit 21 acquires a reliability Q1$c$ (r, θ) that the pixel being processed is in the medical instrument region from the first classification data 521 (S611). The control unit 21 acquires a reliability Q2c (r, θ) that the pixel being processed is in the medical instrument region from the second classification data 522 (S612).

The control unit 21 calculates the synthesis value Qc (r, θ) on the basis of, for example, Expression (5-2) (S613). The control unit 21 determines whether or not the synthesis value Qc (r, θ) is equal to or greater than a predetermined threshold (S614). The predetermined threshold can be, for example, 0.5.

When determining that the synthesis value is equal to or greater than the predetermined threshold (YES in S614), the control unit 21 classifies the pixel being processed into the "medical instrument region" (S615). When determining that the synthesis value is less than the predetermined threshold (NO in S614), the control unit 21 classifies the pixel being processed into the "non-biological tissue region" (S616).

After ending S606, S615, or S616, the control unit 21 determines whether or not to have ended the processing of all the pixels (S607). When determining not to have ended the processing (NO in S607), the control unit 21 returns to S601. When determining that the processing has ended (YES in S607), the control unit 21 ends the processing. The control unit 21 implements the function of the classification data synthesis unit 628 by a subroutine of classification synthesis.

According to the present embodiment, it is possible to provide the catheter system 10 that generates the RT format classification data 528 using the synthesis classification data 526 obtained by synthesizing the classification data 52 output from each of the two classification trained models. It is possible to provide the catheter system 10 having a relatively good balance between the generation cost of the trained model and the classification accuracy by using the second classification trained model 622 that can collect a large number of training data relatively easily and improve the classification accuracy in combination with the first classification trained model 621 that takes time and effort to collect the training data.

Sixth Embodiment

The present embodiment relates to the catheter system 10 that performs classification for each portion constituting a catheter image 51 using position information of a medical instrument as a hint. Description of parts common to the first embodiment will be omitted.

Figures 25, 26:
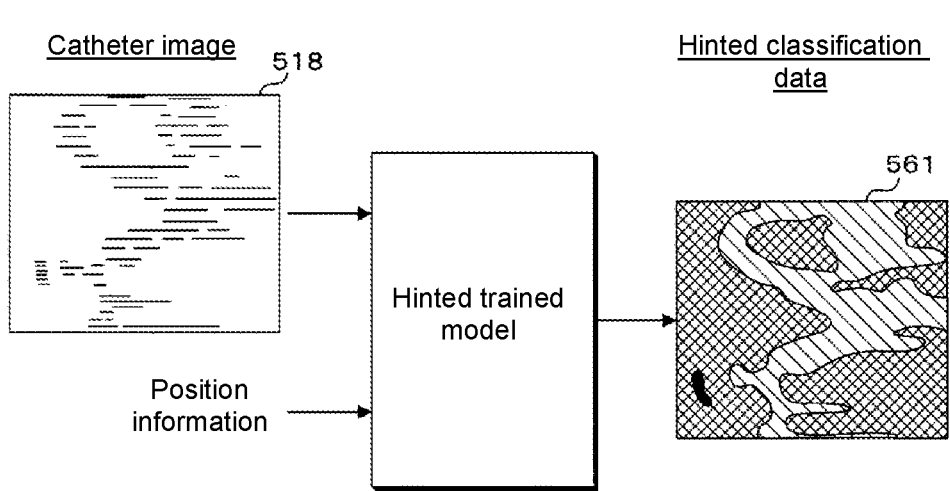
FIG. 25 is an explanatory view explaining a configuration of a hinted trained model.
FIG. 26 is an explanatory view explaining a record layout of a hinted model training data DB.

FIG. 25 is an explanatory view explaining the configuration of the hinted trained model 631. The hinted trained model 631 is used in S604 described with reference to FIG. 4 instead of the classification model 62 described with reference to FIG. 7.

The hinted trained model 631 is a model that receives the RT format catheter image 518 and the position information of the medical instrument visualized in the RT format catheter image 518 and outputs the hinted classification data 561 classified into the "biological tissue region", the "non-biological tissue region", and the "medical instrument region" for each portion constituting the RT format catheter image 518. The first classification trained model 621 further outputs the reliability of the classification result for each portion, that is, the probability that the classification result is correct.

FIG. 26 is an explanatory view explaining the record layout of a hinted model training data DB 72. The hinted training data DB 72 is a database in which the catheter image 51, the position information of the medical instrument visualized in the catheter image 51, and the classification data 52 classified for each visualized subject for each portion constituting the catheter image 51 are recorded in association with one another.

The classification data 52 is data created by the labeler on the basis of a procedure described with reference to FIG. 19, for example. The hinted trained model 631 can be generated by performing processing similar to the machine learning described in the fourth embodiment using the hinted training data DB 72.

Figure 27:
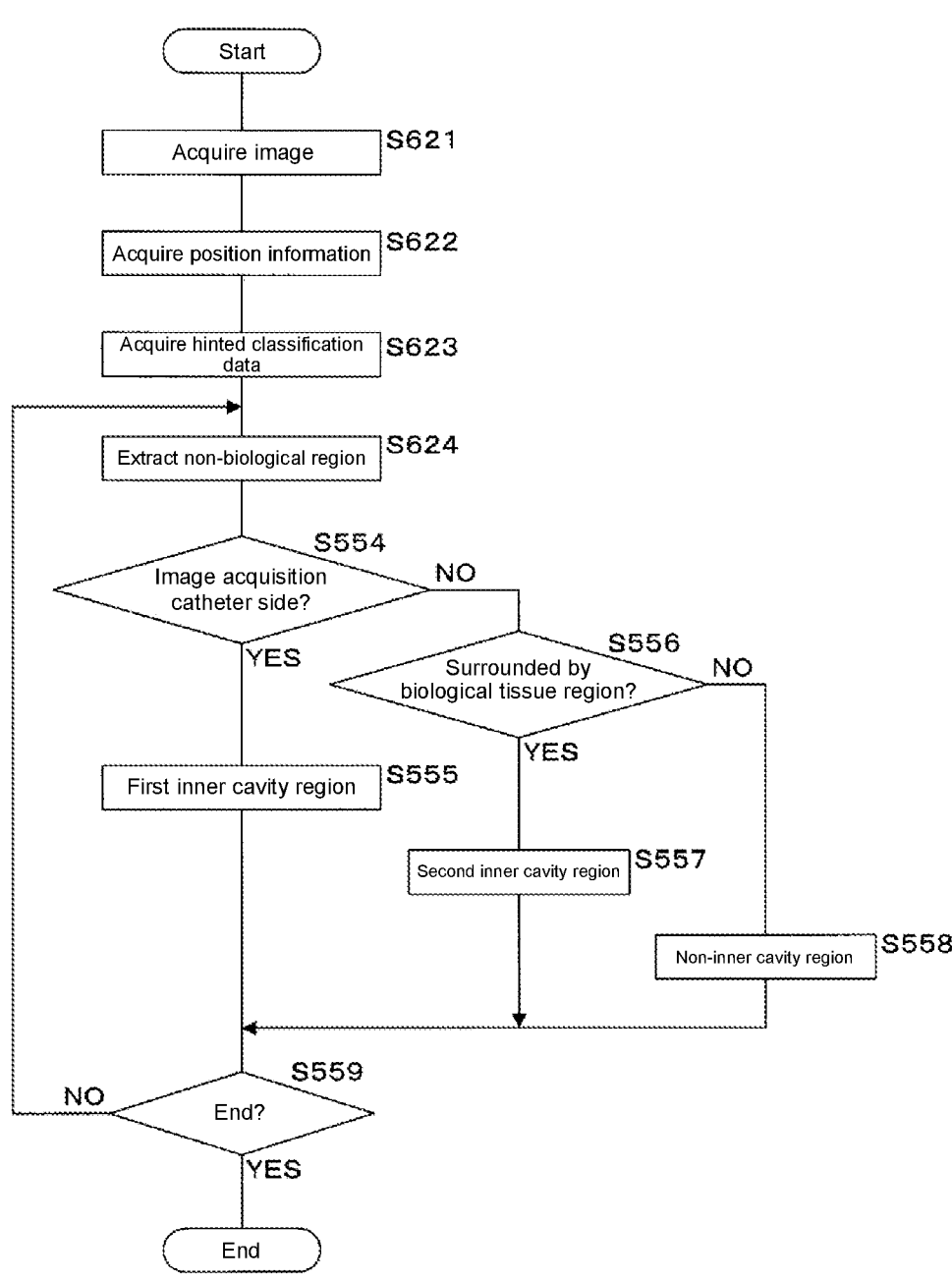
FIG. 27 is a flowchart explaining a flow of processing of a program of a sixth embodiment.

FIG. 27 is a flowchart explaining a flow of the processing of the program of the sixth embodiment. The flowchart described with reference to FIG. 27 illustrates details of the processing performed in S504 described with reference to FIG. 4.

The control unit 21 acquires one frame of the RT format catheter image 518 (S621). The control unit 21 inputs the RT format catheter image 518 to the medical instrument trained model 611 described with reference to FIG. 6, for example, and acquires the position information of the medical instrument (S622). The control unit 21 inputs the RT format catheter image 518 and the position information to the hinted trained model 631 and acquires the hinted classification data 561 (S623).

The control unit 21 extracts one continuous non-biological tissue region from the hinted classification data 561 (S624). The processing on and after the extraction of the non-biological tissue region is desirably performed in a state where the upper end and the lower end of the RT format catheter image 518 are connected to form a cylindrical shape.

The control unit 21 determines whether or not the non-biological tissue region extracted in S624 is on a side in contact with the image acquisition catheter 40 (S554). The processing up to S559 is the same as the processing flow of the program of the fourth embodiment described with reference to FIG. 20, and thus the description of the processing up to S559 is omitted.

The control unit 21 determines whether or not to have ended the processing of all non-biological tissue regions (S559). When determining not to have ended the processing (NO in S559), the control unit 21 returns to S624. When determining that the processing has ended (YES in S559), the control unit 21 ends the processing.

According to the present embodiment, it is possible to provide the catheter system 10 that accurately generates the classification data 52 by inputting the position information of the medical instrument as a hint.

Modification 6-1

Figure 28:
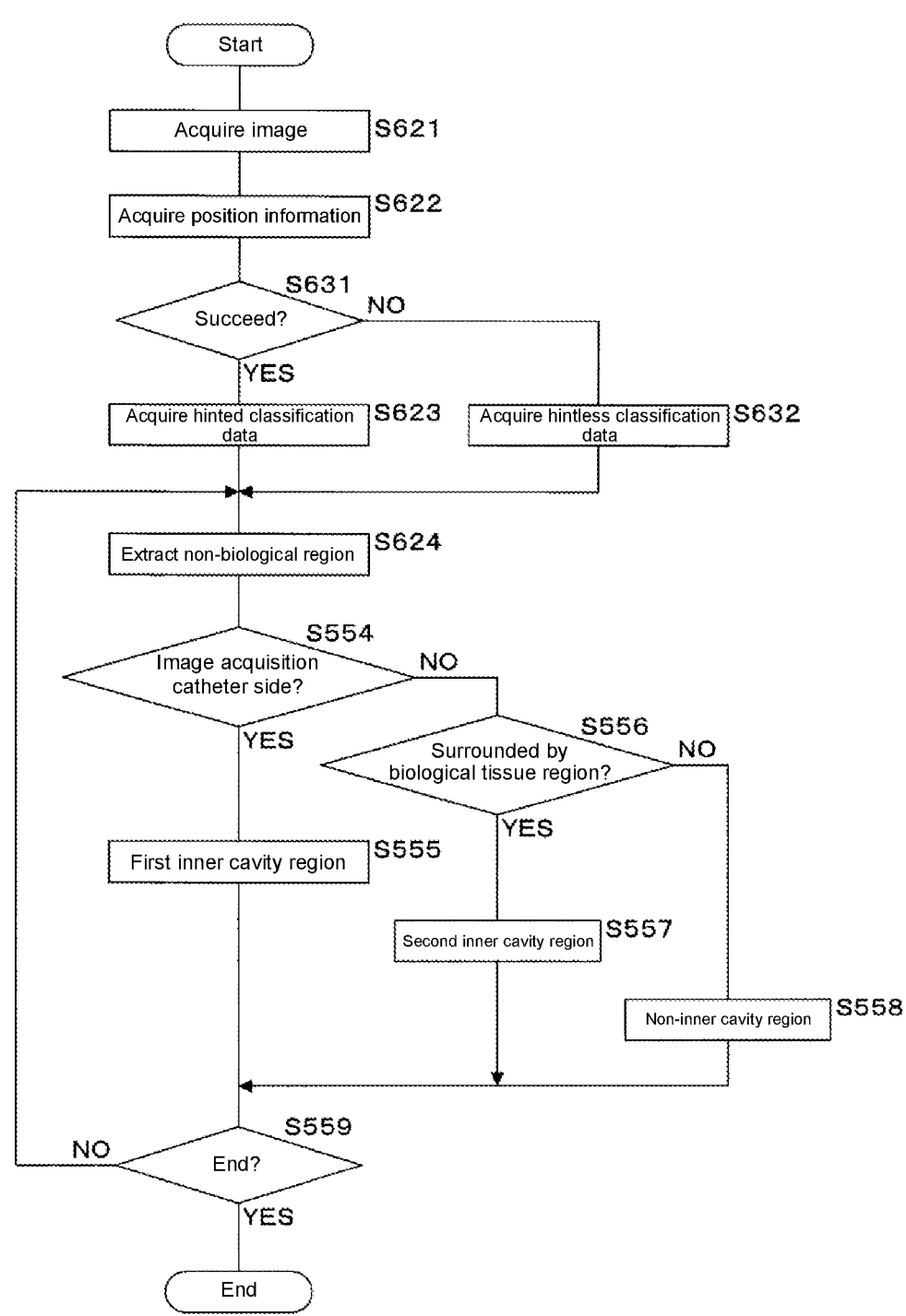
FIG. 28 is a flowchart explaining a flow of processing of a program of a modification.

FIG. 28 is a flowchart explaining a flow of the processing of the program of the modification. The processing described with reference to FIG. 28 is executed instead of the processing described with reference to FIG. 27.

The control unit 21 acquires one frame of the RT format catheter image 518 (S621). The control unit 21 acquires the position information of the medical instrument (S622). The control unit 21 determines whether or not the position information of the medical instrument has been successfully acquired (S631). For example, in a case where the reliability output from the medical instrument trained model 611 is higher than a threshold, the control unit 21 determines that the position information has been successfully acquired.

The "success" in S631 means that the medical instrument is visualized in the RT format catheter image 518, and the control unit 21 succeeds in acquisition of the position information of the medical instrument with reliability higher than the threshold. The case of "not success" includes, for example, a case where there is no medical instrument in the capturing range of the RT format catheter image 518 and a case where the medical instrument is in close contact with the surface of the biological tissue region and is not clearly visualized.

When determining that the acquisition of the position information has succeeded (YES in S631), the control unit 21 inputs the RT format catheter image 518 and the position information to the hinted trained model 631 and acquires the hinted classification data 561 (S623). When determining that the acquisition of the position information has not succeeded (NO in S631), the control unit 21 inputs the RT format catheter image 518 to a hintless trained model 632 and acquires hintless classification data (S632).

The hintless trained model 632 is, for example, the classification model 62 described with reference to FIG. 7, FIG. 18, or FIG. 21. Similarly, the hintless classification data is the classification data 52 output from the classification model 62.

After ending of S623 or S632, the control unit 21 extracts one continuous non-biological tissue region from the hinted classification data 561 or the classification model 62 (S624). Since subsequent processing is the same as the flow of processing described with reference to FIG. 27, the description of the subsequent processing as described with reference to FIG. 27 will be omitted.

The hinted classification data 561 is an example of first data. The hinted trained model 631 is an example of a first trained model that outputs the first data when the catheter image 51 and the position information of the medical instrument are input. The output layer of the hinted trained model 631 is an example of a first data output unit that outputs the first data.

The hintless classification data is an example of second data. The hintless trained model 632 is an example of the second trained model and the second model that output the second data when the catheter image 51 is input. The output layer of the hintless trained model 632 is an example of the second data output unit.

According to the present modification, when the position information has not been successfully acquired, the classification model 62 that does not require input of the position information is used. Therefore, it is possible to provide the catheter system 10 that helps prevent a malfunction caused by inputting an erroneous hint to the hinted trained model 631.

Seventh Embodiment

The present embodiment relates to the catheter system 10 that generates synthesis data 536 by synthesizing the output of the hinted trained model 631 and the output of the hintless trained model 632. Description of parts common to the sixth embodiment will be omitted. The synthesis data 536 is data used instead of the classification data 52, which is the output of S504 described with reference to FIG. 4.

Figure 29:
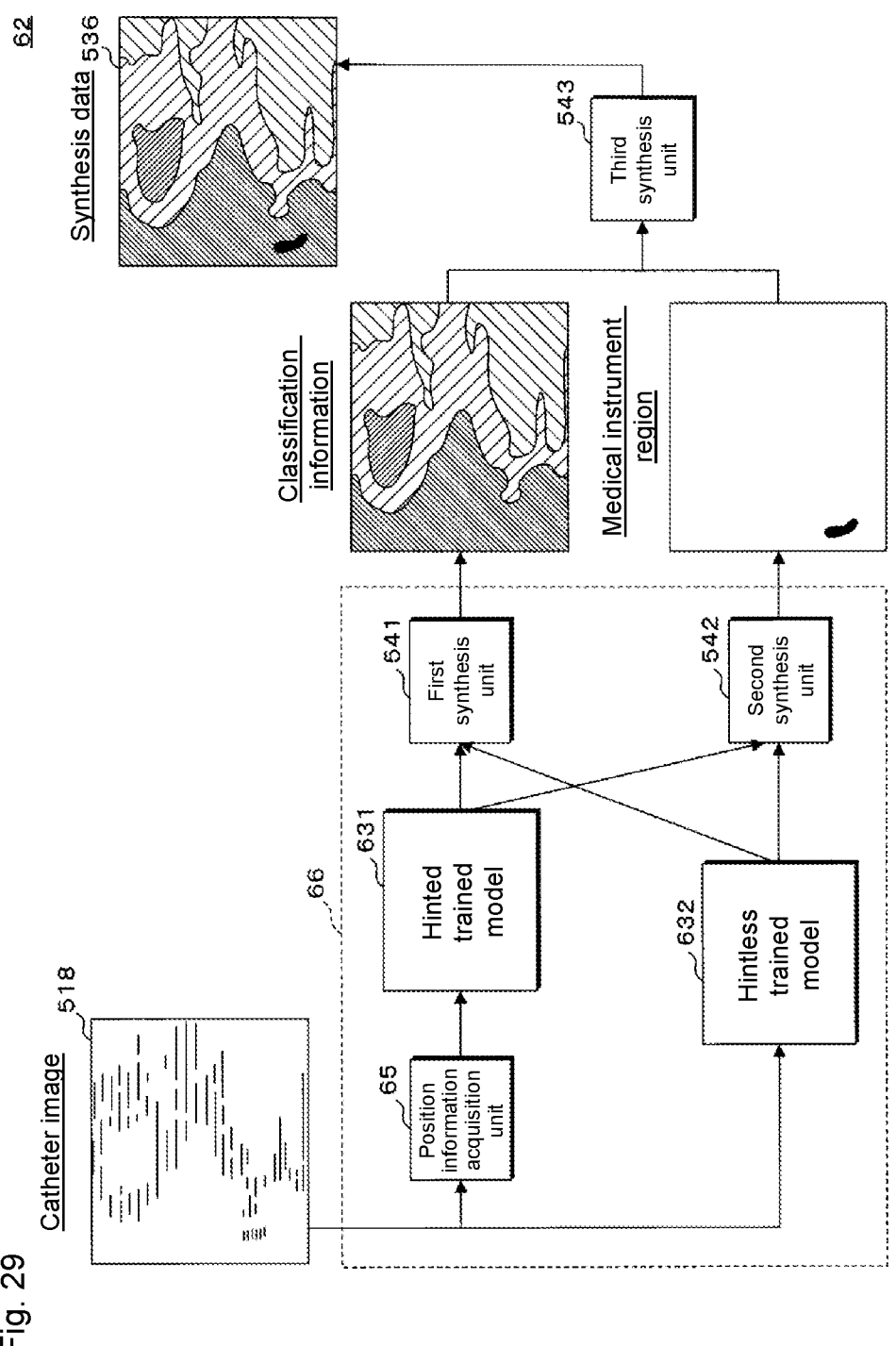
FIG. 29 is an explanatory view explaining a configuration of a classification model of a seventh embodiment.

FIG. 29 is an explanatory view explaining the configuration of the classification model 62 of the seventh embodiment. The classification model 62 includes a position classification analysis unit 66 and a third synthesis unit 543. The position classification analysis unit 66 includes a position information acquisition unit 65, the hinted trained model 631, the hintless trained model 632, a first synthesis unit 541, and a second synthesis unit 542.

The position information acquisition unit 65 acquires the position information indicating the position in which the medical instrument is visualized from the medical instrument trained model 611 described with reference to FIG. 6 or the position information model 619 described with reference to FIG. 16, for example. Since the hinted trained model 631 is similar to that of the sixth embodiment, the description of the hinted trained model 631 will be omitted. The hintless trained model 632 can be, for example, the classification model 62 described with reference to FIG. 7, FIG. 18, or FIG. 21.

The operation of the first synthesis unit 541 will be described. The first synthesis unit 541 creates classification information by synthesizing the hinted classification data 561 output from the hinted trained model 631 and the hintless classification data output from the hintless trained model 632. The input end of the first synthesis unit 541 functions as a first data acquisition unit that acquires the hinted classification data 561 and a second data acquisition unit that acquires the hintless classification data. The output end of the first synthesis unit 541 functions as a first synthesis data output unit that outputs first synthesis data in which the hinted classification data 561 and the hintless classification data are synthesized.

When data in which the non-biological tissue region is not classified into the first inner cavity region, the second inner cavity region, and the non-inner cavity region is input, the first synthesis unit 541 functions as the classification data conversion unit 629 to classify the non-biological tissue region.

For example, in a case where the position information acquisition unit 65 has succeeded in acquiring the position information, the first synthesis unit 541 makes the weight of the hinted classified data 561 from the hinted trained model 631 greater than the weight of the hintless classified data from the hintless trained model 632 and synthesizes both the classified data. Since the method of performing weighting synthesis of images is known, description of the method of performing weighting synthesis of images is omitted.

The first synthesis unit 541 may determine and synthesize weighting of the hinted classification data 561 and the hintless classification data on the basis of the reliability of the position information acquired by the position information acquisition unit 65.

The first synthesis unit 541 may synthesize the hinted classification data 561 and the hintless classification data on the basis of the reliability of the respective regions of the hinted classification data 561 and the hintless classification data. The synthesis based on the reliability of classification data 52 can be executed by processing similar to that of the classification data synthesis unit 628 described in the fifth embodiment, for example.

The first synthesis unit 541 handles the medical instrument region output from the hinted trained model 631 and the hintless trained model 632 in the same manner as the adjacent non-biological tissue regions. For example, when the medical instrument region exists in the first inner cavity region, the first synthesis unit 541 handles the medical instrument region in the same manner as the first inner cavity region. Similarly, when the medical instrument region exists in the second inner cavity region, the first synthesis unit 541 handles the medical instrument region in the same manner as the second inner cavity region.

A trained model that does not output the medical instrument region may be used for any one of the hinted trained model 631 and the hintless trained model 632. Therefore, as illustrated in the central part of FIG. 29, the classification information output from the first synthesis unit 541 does not include information regarding the medical instrument region.

The first synthesis unit 541 may function as a switch that switches between the hinted classification data 561 and the hintless classification data on the basis of whether or not the position information acquisition unit 65 succeeds in acquisition of the position information. The first synthesis unit 541 may further function as the classification data conversion unit 629.

Specifically, when the position information acquisition unit 65 succeeds in acquisition of the position information, the first synthesis unit 541 outputs the classification information on the basis of the hinted classification data 561 output from the hinted trained model 631. When the position information acquisition unit 65 does not succeed in acquisition of the position information, the first synthesis unit 541 outputs the classification information on the basis of the hintless classification data output from the hintless trained model 632.

The operation of the second synthesis unit 542 will be described. When the position information acquisition unit 65 succeeds in acquisition of the position information, the second synthesis unit 542 outputs the medical instrument region output from the hinted trained model 631. When the position information acquisition unit 65 does not succeed in acquisition of the position information, the second synthesis unit 542 outputs the medical instrument region included in the hintless classification data.

It is desirable to use the second classification trained model 622 described with reference to FIG. 21 for the hintless trained model 632. As described above, since a large number of training data can be used for training of the second classification trained model 622, the medical instrument region can be accurately extracted.

When the position information acquisition unit 65 does not succeed in acquisition of the position information, the second synthesis unit 542 may synthesize and output the medical instrument region included in the hinted classification data 561 and the medical instrument region included in the hintless classification data. The synthesis of the hinted classification data 561 and the hintless classification data can be executed by processing similar to that of the classification data synthesis unit 628 described in the fifth embodiment, for example.

The output end of the second synthesis unit 542 functions as a second synthesis data output unit that outputs second synthesis data in which the medical instrument region of the hinted classification data 561 and the medical instrument region of the hintless classification data are synthesized.

The operation of the third synthesis unit 543 will be described. The third synthesis unit 543 outputs the synthesis data 536 in which the medical instrument region output from the second synthesis unit 542 is superimposed on the classification information output from the first synthesis unit 541. In FIG. 29, the superimposed medical instrument region is indicated by black.

Instead of the first synthesis unit 541, the third synthesis unit 543 may function as the classification data conversion unit 629 that classifies the non-biological tissue region into the first inner cavity region, the second inner cavity region, and the non-inner cavity region.

Some or all of the plurality of trained models constituting the position classification analysis unit 66 may be models that receive a plurality of catheter images 51 acquired in time series and output information for the latest catheter images 51.

According to the present embodiment, it is possible to provide the catheter system 10 that acquires the position information of the medical instrument with relatively high accuracy and outputs the position information in combination with the classification information. After generating the synthesis data 536 on the basis of each of the plurality of catheter images 51 continuously captured along the long direction of the image acquisition catheter 40, the control unit 21 may construct and display three-dimensional data of the biological tissue and the medical instrument by laminating the synthesis data 536.

Modification 7-1

Figure 30:
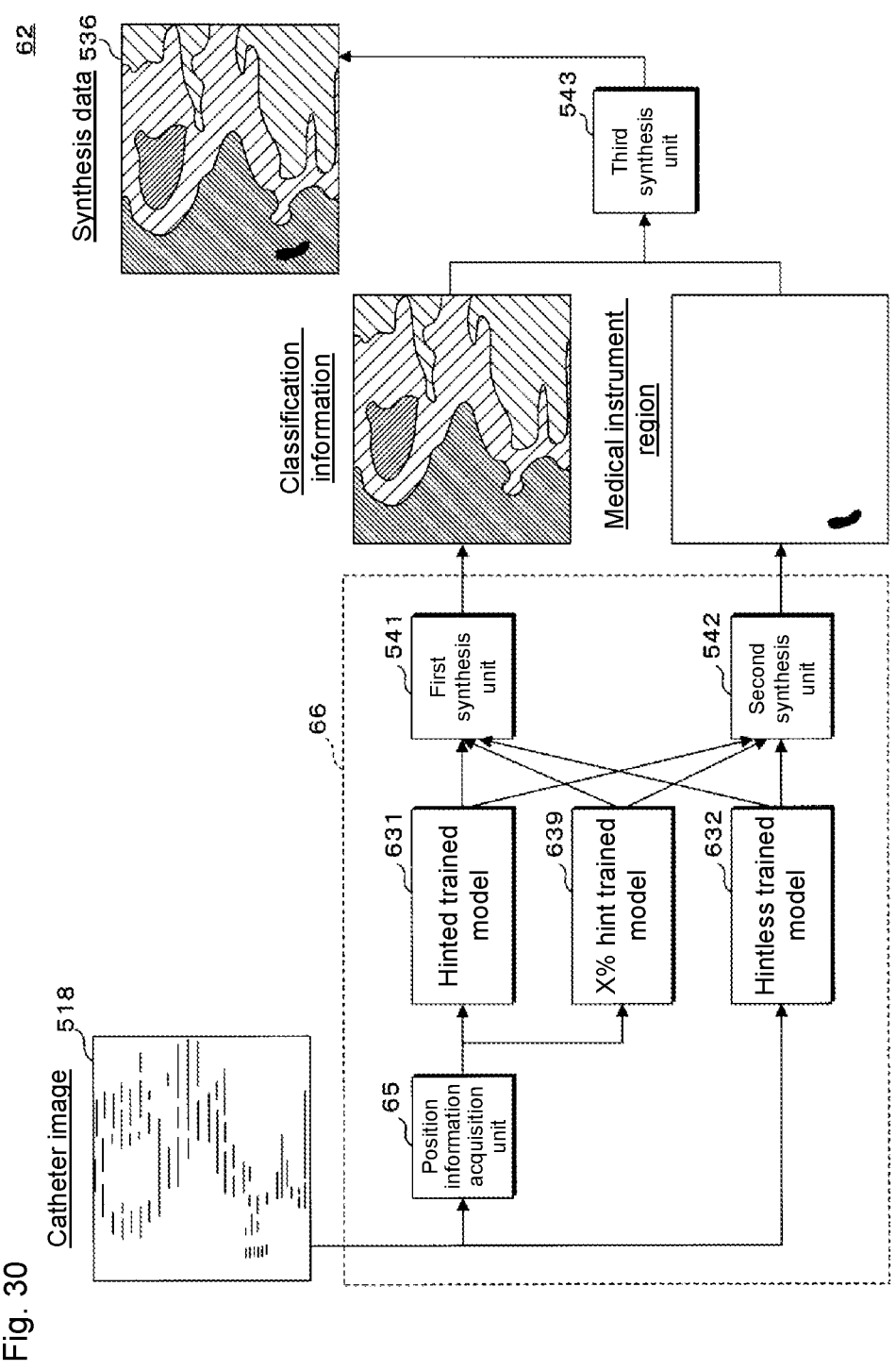
FIG. 30 is an explanatory view explaining a configuration of a classification model of a modification.

FIG. 30 is an explanatory view explaining the configuration of the classification model 62 of the modification. An X % hinted trained model 639 is added to the position classification analysis unit 66. The X % hinted trained model 639 is a model in which, when learning is performed using the hinted training data DB 72, learning is performed under a condition that the position information is input at X percent of the training data and the position information is not input at (100–X) percent. In the following description, the data output from the X % hinted trained model 639 will be referred to as X % hinted classification data.

The X % hinted trained model 639 is the same as the hinted trained model 631 when X is "100", and is the same as the hintless trained model 632 when X is "0". X can be, for example, "50".

The first synthesis unit 541 outputs data in which the classification data 52 acquired from each of the hinted trained model 631, the hintless trained model 632, and the X % hinted trained model 639 is synthesized on the basis of a predetermined weighting. The weighting varies depending on whether or not the position information acquisition unit 65 succeeds in acquisition of the position information.

For example, when the position information acquisition unit 65 succeeds in acquisition of the position information, the output of the hinted trained model 631 and the output of the X % hinted trained model 639 are synthesized. When the position information acquisition unit 65 fails to acquire the position information, the output of the hintless trained model 632 and the output of the X % hinted trained model 639 are synthesized. The weighting at the time of synthesis may change on the basis of the reliability of the position information acquired by the position information acquisition unit 65.

The position classification analysis unit 66 may include the plurality of X % hinted trained models 639. For example, the X % hinted trained model 639 with X of "20" and the X % hinted trained model 639 with X of "50" can be used in combination.

In a clinical setting, there is a case where a medical instrument region cannot be extracted from the catheter image 51. For example, the case includes a case where the medical instrument is not inserted into the first cavity and a case where the medical instrument is in close contact with the surface of the biological tissue. According to the present modification, the classification model 62 that matches such an actual situation in a clinical setting can be implemented. Therefore, it is possible to provide the catheter system 10 that can relatively accurately detect and classify the position information.

Eighth Embodiment

Figure 31:
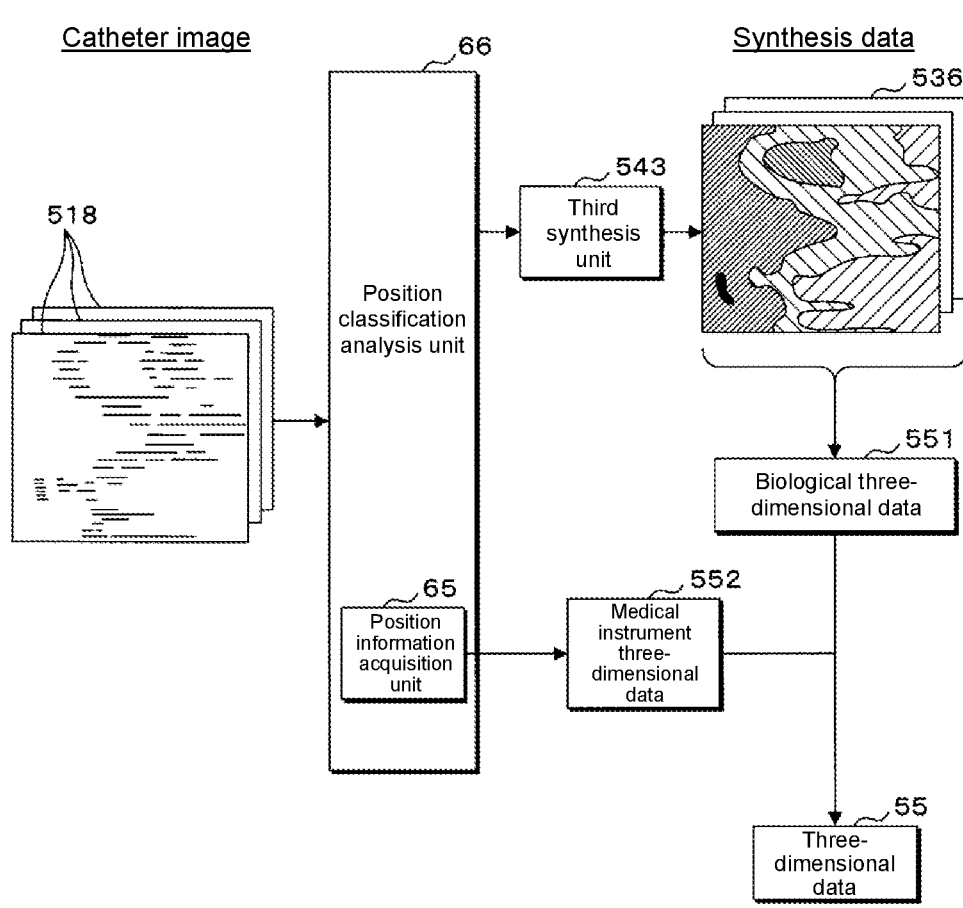
FIG. 31 is an explanatory view explaining an outline of processing of an eighth embodiment.

The present embodiment relates to three-dimensional display of the catheter image 51. Description of parts common to the seventh embodiment will be omitted. FIG. 31 is an explanatory view explaining an outline of the processing of the eighth embodiment.

In the present embodiment, a plurality of RT format catheter images 518 continuously captured along the long direction of the image acquisition catheter 40 are used. The control unit 21 inputs the plurality of RT format catheter images 518 to the position classification analysis unit 66 described in the seventh embodiment. The classification information and the medical instrument region corresponding to the respective RT format catheter images 518 are output from the position classification analysis unit 66. The control unit 21 inputs the classification information and the medical instrument information to the third synthesis unit 543 to synthesize the synthesis data 536.

The control unit 21 creates biological three-dimensional data 551 indicating the three-dimensional structure of the biological tissue on the basis of a plurality of pieces of the synthesis data 536. The biological three-dimensional data 551 is voxel data in which values indicating the biological tissue label, the first inner cavity region label, the second inner cavity region label, the non-inner cavity region label, and the like are recorded for each volume lattice in a three-dimensional space, for example. The biological three-dimensional data 551 may be polygon data configured by a plurality of polygons indicating the boundary of each region. Since the method of creating three-dimensional data 55 on the basis of a plurality of pieces of data in the RT format is known, the description of the method of creating three-dimensional data 55 on the basis of a plurality of pieces of data in the RT format will be omitted.

The control unit 21 acquires position information indicating the position of the medical instrument visualized in each RT format catheter image 518 from the position information acquisition unit 65 included in the position classification analysis unit 66. The control unit 21 creates medical instrument three-dimensional data 552 indicating the three-dimensional shape of the medical instrument on the basis of the plurality of pieces of position information. Details of the medical instrument three-dimensional data 552 will be described later.

The control unit 21 synthesizes the biological three-dimensional data 551 and the medical instrument three-dimensional data 552 to generate the three-dimensional data 55. The three-dimensional data 55 is used for "3D display" in S513 described with reference to FIG. 4. In synthesizing the three-dimensional data 55, the control unit 21 replaces the medical instrument region included in the synthesis data 536 with a blank region or a non-biological region, and then synthesizes the medical instrument three-dimensional data 552. The control unit 21 may generate the biological three-dimensional data 551 using the classification information output from the first synthesis unit 541 included in the position classification analysis unit 66.

FIGS. 32A to 32D are explanatory views explaining an outline of the correction process of the position information. FIGS. 32A to 32D are schematic diagrams illustrating, in time series, a state in which the catheter image 51 is captured while the image acquisition catheter 40 is pulled in the right direction of the figure. The thick cylinder schematically illustrates the inner surface of the first cavity.

Figure 32A:
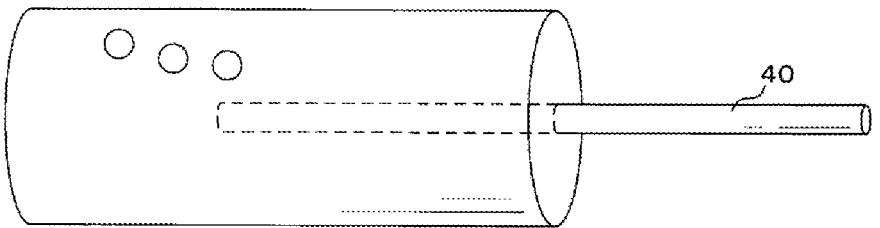
FIG. 32A is an explanatory view explaining an outline of a correction process of the position information.
Figure 32B:
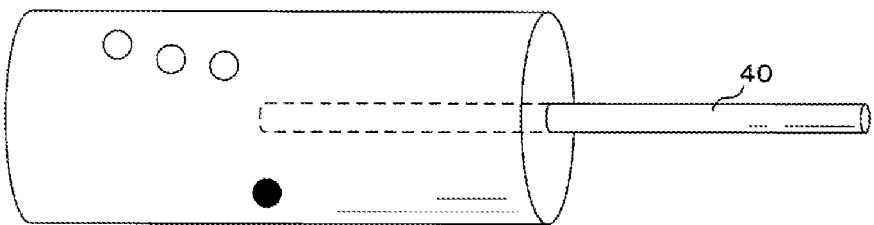
FIG. 32B is an explanatory view explaining an outline of the correction process of the position information.

In FIG. 32A, three catheter images 51 have been captured. The position information of the medical instrument extracted from each catheter image 51 is indicated by a white circle. FIG. 32B illustrates a state in which the fourth catheter image 51 is captured. The position information of the medical instrument extracted from the fourth catheter image 51 is indicated by the black circle.

The medical instrument is detected in a place different from the previously captured three catheter images 51. In general, a medical instrument used in IVR has a certain degree of rigidity and it is less likely to be rapidly bent. Therefore, there is a relatively high possibility that the position information indicated by the black circle is erroneously detected.

Figure 32C:
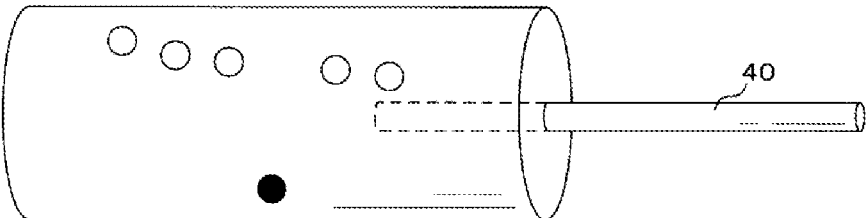
FIG. 32C is an explanatory view explaining an outline of the correction process of the position information.

In FIG. 32C, two more catheter images 51 have been captured. The position information of the medical instrument extracted from each catheter image 51 is indicated by a white circle. The five white circles are arranged in substantially a line along the long direction of the image acquisition catheter 40, but the black circle is far away, and it is obvious that the detection is erroneous.

Figure 32D:
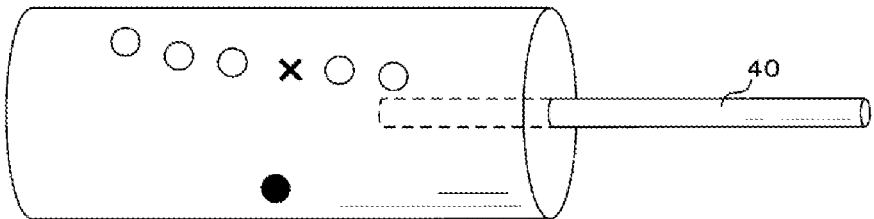
FIG. 32D is an explanatory view explaining an outline of the correction process of the position information.

In FIG. 32D, the position information complemented on the basis of the five white circles is indicated by the cross mark (x). By using the position information indicated by the cross mark (x) instead of the position information indicated by the black circle, the shape of the medical instrument in the first cavity can be correctly displayed in the three-dimensional image.

When the position information acquisition unit 65 does not succeed in acquisition of the position information, the control unit 21 may use, as the position information, the representative point of the medical instrument region acquired from the second synthesis unit 542 included in the position classification analysis unit 66. For example, the center of gravity of the medical instrument region can be used as the representative point.

Figure 33:
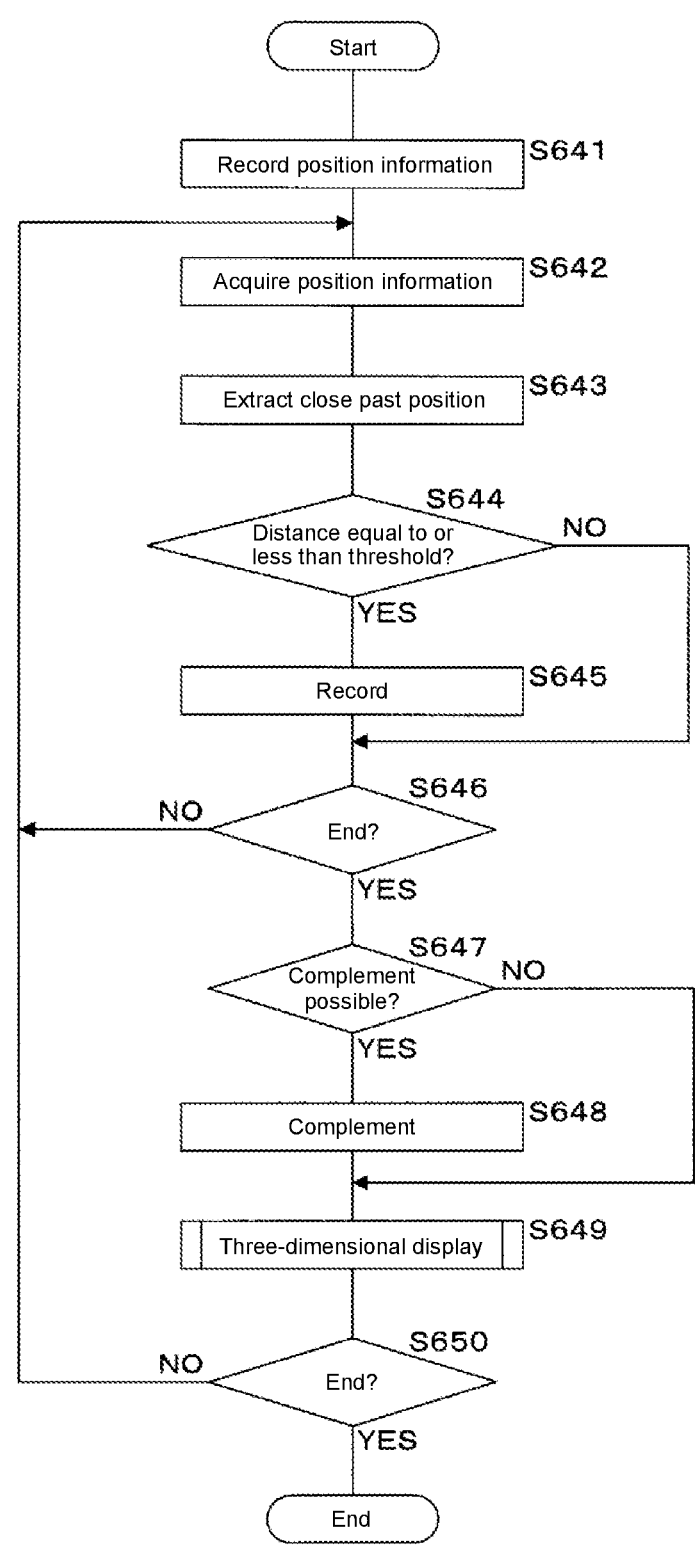
FIG. 33 is a flowchart explaining a flow of processing of a program of the eighth embodiment.

FIG. 33 is a flowchart explaining a flow of the processing of the program of the eighth embodiment. The program described with reference to FIG. 33 is a program to be executed when it is determined in S505 described with reference to FIG. 4 that the user designates three-dimensional display (3D in S505).

The program of FIG. 33 can be executed in the middle of capturing the plurality of catheter images 51 along the longitudinal direction of the image acquisition catheter 40. A case where prior to execution of the program of FIG. 33, classification information and position information have been generated for each of the captured catheter images 51 and are stored in the auxiliary storage device 23 or the external mass storage device will be described as an example.

The control unit 21 acquires the position information corresponding to one catheter image 51 and records the position information in the main storage device 22 or the auxiliary storage device 23 (S641). The control unit 21 sequentially performs processing from catheter images 51 stored earlier among the series of catheter images 51. In S641, the control unit 21 may acquire and record the position information from the first several catheter images 51 among the series of catheter images 51.

The control unit 21 acquires the position information corresponding to the next one catheter image 51 (S642). In the following description, the position information being processed is referred to as first position information. The control unit 21 extracts the position information closest to the first position information from the position information acquired in S641 and past S641 (S643). In the following description, the position information extracted in S643 is referred to as second position information.

In S642, the distance between the pieces of position information is compared in a state where the plurality of catheter images 51 are projected on one plane orthogonal to the image acquisition catheter 40. That is, when the second position information is extracted, the distance in the longitudinal direction of the image acquisition catheter 40 is not considered.

The control unit 21 determines whether or not the distance between the first position information and the second position information is equal to or less than a predetermined threshold (S644). The threshold can be, for example, 3 millimeters. When determining that the distance is equal to or less than the threshold (YES in S644), the control unit 21 records the second position information in the main storage device 22 or the auxiliary storage device 23 (S645).

When determining that the distance exceeds the threshold (NO in S644), or after the end of S645, the control unit 21 determines whether or not to have ended the processing of the recorded position information (S646). When determining not to have ended the processing (NO in S646), the control unit 21 returns to S642.

The position information indicated by black circle in FIG. 32 is an example of the position information determined to exceed the threshold in S644. The control unit 21 ignores such position information without recording it in S645. The control unit 21 implements the function of an exclusion unit that excludes the position information not satisfying a predetermined condition by the processing in the case of determining NO in S644. The control unit 21 may add a flag indicating "error" to the position information determined to exceed the threshold in S644 and record the position information.

When determining has ended (YES in S646), the control unit 21 determines whether or not to be able to complement the position information on the basis of the position information recorded in S641 and S645 (S647). When determining that it is possible (YES in S647), the control unit 21 complements the position information (S648).

In S648, the control unit 21 complements the position information substituting for the position information determined to exceed the threshold in S644, for example. The control unit 21 may complement the position information between the catheter images 51. The complement can be performed using an optional method such as linear interpolation, spline interpolation, Lagrangian interpolation, or Newton interpolation. The control unit 21 implements the function of a complement unit that adds complement information to the position information in S648.

When determining to be unable to perform complementation of the position information (NO in S647), or after the end of S648, the control unit 21 starts a subroutine of three-dimensional display (S649). The subroutine of three-dimensional display is a subroutine that performs three-dimensional display based on the series of catheter images 51. The flow of processing of the subroutine of three-dimensional display will be described later.

The control unit 21 determines whether or not to end the processing (S650). For example, when the MDU 33 starts a new pull-back operation, that is, capturing of the catheter image 51 used for generation of a three-dimensional image, the control unit 21 determines to end the processing.

When determining not to end the processing (NO in S650), the control unit 21 returns to S642. When determining to end the processing (YES in S650), the control unit 21 ends the processing.

In parallel with the execution of the program of FIG. 33, the control unit 21 generates and records classification information and position information on the basis of the newly captured catheter image 51. That is, when it is determined in S646 that the processing has ended, S647 and the subsequent are executed, but there is a possibility that new position information and classification information are generated during the execution of S647 to S650.

FIG. 34 is a flowchart explaining a flow of the processing of the subroutine of three-dimensional display. The subroutine of three-dimensional display is a subroutine that performs three-dimensional display based on the series of catheter images 51. The control unit 21 implements the function of the three-dimensional output unit by the subroutine of three-dimensional display.

The control unit 21 acquires the synthesis data 536 corresponding to the series of catheter images 51 (S661). The control unit 21 creates the biological three-dimensional data 551 indicating the three-dimensional structure of the biological tissue on the basis of the series of synthesis data 536 (S662).

As described above, when synthesizing the three-dimensional data 55, the control unit 21 replaces the medical instrument region included in the synthesis data 536 with a blank region or a non-biological region, and then synthesizes the medical instrument three-dimensional data 552. The control unit 21 may generate the biological three-dimensional data 551 using the classification information output from the first synthesis unit 541 included in the position classification analysis unit 66. The control unit 21 may generate the biological three-dimensional data 551 on the basis of the first classification data 521 described with reference to FIG. 18. That is, the control unit 21 can generate the biological three-dimensional data 551 directly on the basis of the plurality of pieces of first classification data 521.

The control unit 21 may generate the biological three-dimensional data 551 indirectly on the basis of the plurality of pieces of first classification data 521. The expression "indirectly on the basis of" means that the biological three-dimensional data 551 is generated on the basis of the plurality of pieces of synthesis data 536 generated using the plurality of pieces of first classification data 521, as described with reference to FIG. 31, for example. The control unit 21 may generate the biological three-dimensional data 551 on the basis of a plurality of pieces of data different from the synthesis data 536 generated using the first plurality of pieces of classification data 521.

The control unit 21 gives thickness information to a curve defined by a series of position information recorded in S641 and S645 and the complement information complemented in S648 of the program described with reference to FIG. 33 (S663). The thickness information is desirably a thickness of the medical instrument generally used in the IVR manipulation. The control unit 21 may receive information regarding the medical instrument in use and give thickness information corresponding to the medical instrument. By giving the thickness information, the three-dimensional shape of the medical instrument is reproduced.

The control unit 21 synthesizes the biological three-dimensional data 551 generated in S662 with the three-dimensional shape of the medical instrument generated in S662 (S664). The control unit 21 displays the synthesized three-dimensional data 55 on the display device 31 (S665).

The control unit 21 receives, from the user, an instruction such as rotation, change of a cross section, enlargement, and reduction with respect to the three-dimensionally displayed image, and changes the display. Since reception of an instruction with respect to a three-dimensionally displayed image and a change in display have been conventionally performed, a description of the reception of an instruction with respect to a three-dimensionally displayed image and a change in display will be omitted. The control unit 21 ends the processing.

According to the present embodiment, it is possible to provide the catheter system 10 that removes the influence of erroneous detection of position information and displays a medical instrument having a shape. For example, the user can rather easily grasp the positional relationship between the Brockenbrough needle and the fossa ovalis and perform the IVR manipulation.

Instead of performing the processing from S643 to S645, a plurality of pieces of position information may be subjected to clustering processing to remove abnormal position information largely separated from other position information.

Modification 8-1

The present modification relates to the catheter system 10 that performs three-dimensional display on the basis of the medical instrument region detected from the catheter image 51 when the medical instrument is not erroneously detected. Description of parts common to the eighth embodiment will be omitted.

In S663 of the subroutine described with reference to FIG. 34, the control unit 21 determines the thickness of the medical instrument on the basis of the medical instrument region output from the hinted trained model 631 or the hintless trained model 632, for example. However, for the catheter image 51 whose position information is determined to be erroneous, the thickness information is complemented on the basis of the medical instrument regions of the preceding and following catheter images 51.

According to the present modification, it is possible to provide the catheter system 10 that appropriately displays, in a three-dimensional image, a medical instrument whose thickness changes in the middle, such as a medical instrument in a state where a needle protrudes from a sheath.

Ninth Embodiment

The present embodiment relates to padding processing suitable for a trained model that processes the RT format catheter image 518 acquired using a radial scanning type image acquisition catheter 40. Description of parts common to the first embodiment will be omitted.

The padding processing is processing of adding data around the input data before performing convolution processing. In the convolution processing immediately after the input layer that receives input of the image, the input data is the input image. In the convolution processing other than immediately after the input layer, the input data is a feature map extracted in the previous stage. In the trained model that processes image data, what is called zero padding processing of giving data of "0" to the periphery of the input data input to the convolution layer is generally performed.

FIG. 35 is an explanatory view explaining the padding processing in the ninth embodiment. The right end of FIG. 35 is a schematic diagram of the input data to be input to a convolution layer. The convolution layer can be, for example, an example of a first convolution layer included in the medical instrument trained model 611 and a second convolution layer included in the angle trained model 612. The convolution layer may be a convolution layer included in an optional trained model used for processing of the catheter image 51 captured using the radial scanning type image acquisition catheter 40.

The input data is in RT format, with the lateral direction corresponding to the distance from the sensor 42 and the longitudinal direction corresponding to the scanning angle. An enlarged schematic diagram of the upper right end part and the lower left end part of the input data is illustrated in the center of FIG. 35. Each frame corresponds to a pixel, and the numerical value in the frame corresponds to a pixel value.

The right end of FIG. 35 is a schematic diagram of data after the padding processing of the present embodiment is performed. The numerical value indicated in italics indicates data added by the padding processing. Data of "0" is added to the left and right ends of the input data. The data indicated by "A" at the lower end of the data is copied to the upper end of the input data before the padding processing is performed. The data indicated by "B" at the upper end of the data is copied to the lower end of the input data before the padding processing is performed.

That is, in the right end of FIG. 35, the same data as the data on the side with the larger scanning angle is added to the outer side of the side with the smaller scanning angle, and the same data as the data on the side with the smaller scanning angle is added to the outer side of the side with the larger scanning angle. In the following description, the padding processing described with reference to FIG. 35 is referred to as polar padding processing.

In the radial scanning type image acquisition catheter 40, the upper end and the lower end of the RT format catheter image 518 are substantially the same. For example, one medical instrument, a lesion, or the like may be separated above and below the RT format catheter image 518. The polar padding processing is processing using such feature.

According to the present embodiment, it is possible to generate a trained model that sufficiently reflects upper and lower information of an image in the RT format.

The polar padding processing may be performed in all the convolution layers included in the trained model, or the polar padding processing may be performed in some of the convolution layers.

FIG. 35 illustrates an example of performing the padding processing of adding one data to each of four directions of input data, but the padding processing may be processing of adding a plurality of pieces of data. The number of pieces of data to be added by the polar padding processing is selected according to the size and stride amount of the filter used in the convolution processing.

Modification 9-1

FIG. 36 is an explanatory view explaining the polar padding processing of the modification. The polar padding processing of the present modification is effective for the convolution layer at the stage of first processing of the RT format catheter image 518.

The upper side of FIG. 36 schematically illustrates a state in which radial scanning is performed while pulling the sensor 42 rightward. One RT format catheter image 518 schematically illustrated at the lower left of FIG. 36 is generated on the basis of the scanning line data acquired during one rotation of the sensor 42. The RT format catheter image 518 is formed from the upper side to the lower side according to the rotation of the sensor 42.

The lower right of FIG. 36 schematically illustrates a state in which the padding processing is performed on the RT format catheter image 518. The data of a terminal portion of the RT format catheter image 518 before one rotation indicated by left-downward hatching is added to the upper side of the RT format catheter image 518. The data of a start portion of the RT format catheter image 518 after one rotation indicated by right-downward hatching is added to the lower side of the RT format catheter image 518. Data of "0" is added to the left and right of the RT format catheter image 518.

According to the present modification, since the padding processing based on the actual scanning line data is performed, it is possible to generate the trained model that sufficiently reflects the information above and below the image in the RT format more accurately.

Tenth Embodiment

FIG. 37 is an explanatory view explaining the configuration of the catheter system 10 of the tenth embodiment. The present embodiment relates to a mode for achieving the catheter system 10 of the present embodiment by operating the catheter control device 27, the MDU 33, the image acquisition catheter 40, a general-purpose computer 90, and a program 97 in combination. Description of parts common to the first embodiment will be omitted.

The catheter control device 27 is an ultrasound diagnosis device for IVUS that performs control of the MDU 33, control of the sensor 42, generation of a lateral tomographic image and a longitudinal tomographic image based on a signal received from the sensor 42, and the like. Since the function and configuration of the catheter control device 27 are similar to those of a conventionally used ultrasound diagnosis device, the description of the catheter control device 27 will be omitted.

The catheter system 10 of the present embodiment includes the computer 90. The computer 90 includes the control unit 21, the main storage device 22, the auxiliary storage device 23, the communication unit 24, the display unit 25, the input unit 26, a reading unit 29, and the bus. The computer 90 can be, for example, an information device such as a general-purpose personal computer, a tablet, a smartphone, or a server computer.

The program 97 is recorded in a portable recording medium 96. The control unit 21 reads the program 97 via the reading unit 29 and saves the program in the auxiliary storage device 23. The control unit 21 may read the program 97 stored in a semiconductor memory 98 such as a flash memory mounted in the computer 90. Furthermore, the control unit 21 may download the program 97 from another server computer not illustrated connected via the communication unit 24 and a network not illustrated, and save the program in the auxiliary storage device 23.

The program 97 is installed as a control program of the computer 90, and is loaded and executed on the main storage device 22. Due to this, the computer 90 functions as the information processing device 20 described above.

The computer 90 can be, for example, a general-purpose personal computer, a tablet, a smartphone, a large computer, a virtual machine operating on a large computer, a cloud computing system, or a quantum computer. The computer 90 may be a plurality of personal computers or the like that performs distributed processing.

Eleventh Embodiment

FIG. 38 is a functional block diagram of the information processing device 20 of the eleventh embodiment. The information processing device 20 includes an image acquisition unit 81, a position information acquisition unit 84, and a first data output unit 85. The image acquisition unit 81 acquires the catheter image 51 including the inner cavity obtained by the image acquisition catheter 40. The position information acquisition unit 84 acquires position information regarding the position of the medical instrument inserted into the inner cavity included in the catheter image 51.

In a case where the catheter image 51 and the position information are input, the first data output unit 85 inputs the acquired catheter image 51 and the acquired position information to the first trained model 631 that outputs the first data 561 in which each region of the catheter image 51 is classified into at least three of the biological tissue region, the medical instrument region where the medical instrument exists, and the non-biological tissue region, and outputs the first data 561.

Note A1

An information processing device including: an image acquisition unit that acquires a catheter image obtained by an image acquisition catheter inserted into a first cavity; and a first classification data output unit that inputs the acquired catheter image to a first classification trained model that, upon receiving input of the catheter image, outputs first classification data in which a non-biological tissue region including a first inner cavity region that is inside the first cavity and a second inner cavity region that is inside a second cavity where the image acquisition catheter is not inserted, and a biological tissue region are classified as different regions, and outputs the first classification data, in which the first classification trained model is generated using first training data that clearly indicates at least the non-biological tissue region including the first inner cavity region and the second inner cavity region and the biological tissue region.

Note A2

The information processing device according to Note A1 including: an inner cavity region extraction unit that extracts each of the first inner cavity region and the second inner cavity region from the non-biological tissue region in the first classification data; and a first mode output unit that changes the first classification data into a mode in which the first inner cavity region, the second inner cavity region, and the biological tissue region can be distinguished from one another, and outputs the first classification data.

Note A3

The information processing device according to Note A1 or A2 including a second mode output unit that extracts a non-inner cavity region that is neither the first inner cavity region nor the second inner cavity region from the non-biological tissue region in the first classification data, and changes the first classification data into a mode in which the first inner cavity region, the second inner cavity region, the non-inner cavity region, and the biological tissue region can be distinguished from one another and outputs the first classification data.

Note A4

The information processing device according to Note A3, in which the first classification trained model outputs the first classification data in which the biological tissue region, the first inner cavity region, the second inner cavity region, and the non-inner cavity region are classified as different regions from one another when the catheter image is input.

Note A5

The information processing device according to any one of Notes A1 to A4, in which the image acquisition catheter is a radial scanning type tomographic image acquisition catheter, and the catheter image is an RT format image in which a plurality of pieces of scanning line data acquired from the image acquisition catheter are arrayed in parallel in order of a scanning angle, and the first classification data is a classification result of each pixel in the RT format image.

Note A6

The information processing device according to Note A5, in which the first classification trained model includes a plurality of convolution layers, and at least one of the plurality of convolution layers is trained by performing padding processing of adding same data as that on a side with a large scanning angle to an outer side of a side with a small scanning angle and adding same data as that on a side with a small scanning angle to an outer side of a side with a large scanning angle.

Note A7

The information processing device according to any one of Notes A1 to A6, in which in a case where the plurality of catheter images acquired in time series are input, the first classification trained model outputs the first classification data in which the non-biological tissue region and the biological tissue region are classified regarding a latest catheter image among the plurality of catheter images.

Note A8

The information processing device according to Note A7, in which the first classification trained model includes a memory portion that holds information regarding the catheter image input in past, and outputs the first classification data on a basis of information held in the memory portion and the latest catheter image among the plurality of catheter images.

Note A9

The information processing device according to any one of Notes A1 to A8, in which the first classification trained model outputs the first classification data in which the biological tissue region, the non-biological tissue region, and a medical instrument region indicating a medical instrument inserted into the first cavity or the second cavity are classified as different regions, when the catheter image is input.

Note A10

The information processing device according to any one of Notes A1 to A9 including: a second classification data acquisition unit that inputs the acquired catheter image to a second classification trained model that, upon receiving input of the catheter image, outputs second classification data in which the non-biological tissue region including the first inner cavity region and the biological tissue region are classified as different regions, and acquires second classification data to be output; and a synthesis classification data output unit that outputs synthesis classification data in which the second classification data is synthesized with the first classification data, in which the second classification trained model is generated using second training data that clearly indicates only the first inner cavity region of the non-biological tissue region.

Note A11

The information processing device according to Note A10, in which the second classification trained model outputs the second classification data in which the biological tissue region, the non-biological tissue region, and a medical instrument region indicating a medical instrument inserted into the first cavity or the second cavity are classified as different regions from one another, when the catheter image is input.

Note A12

The information processing device according to Notes A10 or A11, in which the first classification trained model further outputs a probability that each portion of the catheter image is the biological tissue region or a probability that each portion of the catheter image is the non-biological tissue region, the second classification trained model further outputs a probability that each portion of the catheter image is the biological tissue region or a probability that each portion of the catheter image is the non-biological tissue region, and the synthesis classification data output unit outputs synthesis classification data in which the second classification data is synthesized with the first classification data on a basis of a result of calculating a probability that each portion of the catheter image is the biological tissue region or a probability that each portion of the catheter image is the non-biological tissue region.

Note A13

The information processing device according to any one of Notes A1 to A12, in which the image acquisition catheter is a three-dimensional scanning catheter that sequentially acquires the plurality of catheter images along a long direction of the image acquisition catheter.

Note A14

The information processing device according to Note A13 including a three-dimensional output unit that outputs a three-dimensional image generated on a basis of a plurality of pieces of the first classification data generated from the plurality of respective acquired catheter images.

Note A15

An information processing method for causing a computer to execute processing of acquiring a catheter image obtained by an image acquisition catheter inserted into a first cavity, and inputting the acquired catheter image to a first classification trained model that is generated using first training data that clearly indicates a non-biological tissue region at least including a first inner cavity region that is inside of the first cavity and a second inner cavity region that is inside of a second cavity in which the image acquisition catheter is not inserted and a biological tissue region, and outputs first classification data in which the non-biological tissue region and the biological tissue region are classified as different regions when the catheter image is input, and outputting the first classification data.

Note A16

A non-transitory computer-readable medium storing a program, which when executed by a computer, performs processing comprising: acquiring a catheter image obtained by an image acquisition catheter inserted into a first cavity, and inputting the acquired catheter image to a first classification trained model that is generated using first training data that clearly indicates a non-biological tissue region at least including a first inner cavity region that is inside of the first cavity and a second inner cavity region that is inside of a second cavity in which the image acquisition catheter is not inserted and a biological tissue region, and outputs first classification data in which the non-biological tissue region and the biological tissue region are classified as different regions when the catheter image is input, and outputting the first classification data.

Note A17

A generation method for a trained model comprising: acquiring a plurality of sets of training data in which a catheter image obtained by an image acquisition catheter inserted into a first cavity, label data given a plurality of labels having a biological tissue region label indicating a biological tissue region for each portion of the catheter image, and a non-biological tissue region label including a first inner cavity region indicating being inside of the first cavity, a second inner cavity region indicating being inside of a second cavity where the image acquisition catheter is not inserted, and a non-inner cavity region that is neither the first inner cavity region nor the second inner cavity region are recorded in association with each other; and generating a trained model that outputs the biological tissue region label and the non-biological tissue region label for each portion of the catheter image in a case where the catheter image is input with the catheter image as input and the label data as output using the plurality of sets of training data.

Note A18

The generation method for a trained model according to Note A17, in which the non-biological tissue region label of the plurality of sets of training data includes a first inner cavity region label indicative of the first inner cavity region, a second inner cavity region label indicative of the second inner cavity region, and a non-inner cavity region label indicative of the non-inner cavity region, and a trained model is generated, the trained model outputting the biological tissue region label, the first inner cavity region label, the second inner cavity region label, and the non-inner cavity region label for each portion of the catheter image in a case where the catheter image is input with the catheter image as input and the label data as output using the plurality of sets of training data.

Note A19

A generation method for a trained model comprising: acquiring a plurality of sets of training data in which a catheter image obtained by an image acquisition catheter inserted into a first cavity, label data given a plurality of labels having a biological tissue region label indicating a biological tissue region generated on a basis of boundary line data indicating a boundary line inside the first cavity in the catheter image, and a non-biological tissue region label including a first inner cavity region indicating being inside of the first cavity are recorded in association with each other; and generating a trained model that outputs the biological tissue region label and the non-biological tissue region label for each portion of the catheter image in a case where the catheter image is input with the catheter image as input and the label data as output using the plurality of sets of training data.

Note A20

The generation method for a trained model according to any one of Notes A17 to A19, in which the catheter image is an RT format image in which scanning line data for one rotation obtained by the radial scanning type image acquisition catheter are arrayed in parallel in order of a scanning angle, the trained model includes a plurality of convolution layers, and at least one of the plurality of convolution layers is trained by performing padding processing of adding same data as that on a side with a large scanning angle to an outer side of a side with a small scanning angle and adding same data as that on a side with a small scanning angle to an outer side of a side with a large scanning angle.

Note B1

An information processing device including: an image acquisition unit that acquires a catheter image obtained by a radial scanning type image acquisition catheter; and a first position information output unit that inputs the acquired catheter image to a medical instrument trained model that, upon receiving input of the catheter image, outputs first position information regarding a position of a medical instrument included in the catheter image, and outputs the first position information.

Note B2

The information processing device according to Note B1, in which the first position information output unit outputs the first position information by using a position of one pixel included in the catheter image.

Note B3

The information processing device according to Note B1 or B2, in which the first position information output unit includes a first position information acquisition unit that acquires the first position information in time series corresponding to each of the plurality of catheter images obtained in time series, an exclusion unit that excludes the first position information that does not satisfy a predetermined condition from the time-series first position information, and a complement unit that adds complement information satisfying a predetermined condition to the time-series first position information.

Note B4

The information processing device according to any one of Notes B1 to B3, in which the medical instrument trained model outputs the first position information regarding a latest catheter image among the plurality of catheter images in a case where the plurality of catheter images acquired in time series are input.

Note B5

The information processing device according to Note B4, in which the medical instrument trained model includes a memory portion that holds information regarding the catheter image input in past, and outputs the first position information on a basis of information held in the memory portion and the latest catheter image among the plurality of catheter images.

Note B6

The information processing device according to any one of Notes B1 to B5, in which the medical instrument trained model receives an input of the catheter image in an RT format image in which a plurality of pieces of scanning line data acquired from the image acquisition catheter are arrayed in parallel in order of a scanning angle, and includes a plurality of first convolution layers, and at least one of the plurality of first convolution layers is trained by performing padding processing of adding same data as that on a side with a large scanning angle to an outer side of a side with a small scanning angle and adding same data as that on a side with a small scanning angle to an outer side of a side with a large scanning angle.

Note B7

The information processing device according to any one of Notes B1 to B6 including: a scanning angle information acquisition unit that inputs the acquired catheter image to an angle trained model that, upon receiving input of the catheter image, outputs scanning angle information regarding a position of a medical instrument included in the catheter image, and acquires the output scanning angle information; and a second position information output unit that outputs second position information regarding a position of a medical instrument included in the catheter image on a basis of the first position information output from the medical instrument trained model and the scanning angle information output from the angle trained model.

Note B8

The information processing device according to Note B7, in which the angle trained model receives an input of the catheter image in an RT format image in which a plurality of pieces of scanning line data acquired from the image acquisition catheter are arrayed in parallel in order of a scanning angle, and includes a plurality of second convolution layers, and at least one of the plurality of second convolution layers is trained by performing padding processing of adding same data as that on a side with a large scanning angle to an outer side of a side with a small scanning angle and adding same data as that on a side with a small scanning angle to an outer side of a side with a large scanning angle.

Note B9

The information processing device according to any one of Notes B1 to B8, in which the medical instrument trained model is generated using a plurality of sets of training data in which the catheter image and a position of a medical instrument included in the catheter image are recorded in association with each other.

Note B10

The information processing device according to Note B9, in which the training data is generated by processing of displaying the catheter image obtained by the image acquisition catheter, receiving a position of a medical instrument included in the catheter image by one click operation or one tap operation on the catheter image, and storing the catheter image and a position of a medical instrument in association with each other.

Note B11

The information processing device according to Note B9, wherein the training data is generated by processing of inputting the catheter image to the medical instrument trained model, displaying the first position information output from the medical instrument trained model superimposed on the catheter image having been input, storing, as the training data, non-correction data in which the catheter image and the first position information are associated with each other, in a case of not receiving a correction instruction regarding a position of a medical instrument included in the catheter image, and storing, as the training data, correction data in which the catheter image and information regarding a position of a medical instrument on a basis of the correction instruction are associated with each other in a case of receiving a correction instruction regarding a position of a medical instrument included in the catheter image.

Note B12

A generation method for a trained model including acquiring a plurality of sets of training data in which a catheter image obtained by an image acquisition catheter and first position information regarding a position of a medical instrument included in the catheter image are recorded in association with each other; and generating a trained model that outputs first position information regarding a position of a medical instrument included in the catheter image when the catheter image is input on a basis of the plurality of sets of the training data.

Note B13

The generation method for a trained model according to Note B12, in which the first position information is information regarding a position of one pixel included in the catheter image.

Note B14

A training data generation method for causing a computer to execute processing of displaying a catheter image including an inner cavity obtained by an image acquisition catheter, receiving first position information regarding a position of a medical instrument inserted into the inner cavity included in the catheter image by one click operation or one tap operation on the catheter image, and storing training data in which the catheter image and the first position information are associated with each other.

Note B15

The training data generation method according to Note B14, in which the first position information is information regarding a position of one pixel included in the catheter image.

Note B16

The training data generation method according to Note B14 or B15, in which when the first position information is received for the catheter image, another catheter images obtained continuously in time series is displayed.

Note B17

The training data generation method according to any one of Notes B14 to B16, in which the image acquisition catheter is a radial scanning type tomographic image acquisition catheter, the catheter image is displayed in such a manner that two images are displayed side by side, the two images being an RT format image in which a plurality of pieces of scanning line data acquired from the image acquisition catheter are arrayed in parallel in order of a scanning angle and an XY format image in which data based on the scanning line data are arranged radially around the image acquisition catheter, and the first position information is received from any of the RT format image and the XY format image.

Note B18

A training data generation method for causing a computer to execute processing of inputting a catheter image to a medical instrument trained model that outputs first position information regarding a position of the medical instrument included in the catheter image when the catheter image obtained by the image acquisition catheter is input, displaying the first position information output from the medical instrument trained model superimposed on the catheter image having been input, storing, as training data, non-correction data in which the catheter image and the first position information are associated with each other, in a case of not receiving a correction instruction regarding a position of a medical instrument included in the catheter image, and storing, as the training data, correction data in which the catheter image and information regarding a position of a medical instrument having been received are associated with each other in a case of receiving a correction instruction regarding a position of a medical instrument included in the catheter image.

Note B19

The training data generation method according to Note B18, in which the non-correction data and the corrected data are data regarding a position of one pixel included in the catheter image.

Note B20

The training data generation method according to Note B18 or B19, in which the plurality of catheter images obtained in time series are input to the medical instrument trained model in order, and are displayed in order superimposed on the input catheter image in which each positions having been output is input.

Note B21

The training data generation method according to any one of Notes B18 to B20, in which a position of the medical instrument is received by one click operation or one tap operation.

Note B22

The training data generation method according to any one of Notes B18 to B21, in which the image acquisition catheter is a radial scanning type tomographic image acquisition catheter, the catheter image is displayed in such a manner that two images are displayed side by side, the two images being an RT format image in which a plurality of pieces of scanning line data acquired from the image acquisition catheter are arrayed in parallel in order of a scanning angle and an XY format image in which data based on the scanning line data are arranged radially around the image acquisition catheter, and a position of the medical instrument is received from any of the RT format image and the XY format image.

Note C1

An information processing device including: an image acquisition unit that acquires a catheter image including an inner cavity obtained by an image acquisition catheter; a position information acquisition unit that acquires position information regarding a position of a medical instrument inserted into the inner cavity included in the catheter image; and a first data output unit that inputs the acquired catheter image and the acquired position information to a first trained model that, upon receiving input of the catheter image and the position information, outputs first data in which each region of the catheter image is classified into at least three of a biological tissue region, a medical instrument region where the medical instrument exists, and a non-biological tissue region, and outputs the first data.

Note C2

The information processing device according to Note C1, in which the position information acquisition unit inputs the acquired catheter image to a medical instrument trained model that, upon receiving input of the catheter image, outputs the position information included in the catheter image, and acquires the position information from the medical instrument trained model.

Note C3

The information processing device according to Note C2 including: a second data acquisition unit that inputs a catheter image having been acquired to a second model that, upon receiving input of the catheter image without receiving input of the position information, outputs second data in which each region of the catheter image is classified into at least three of a biological tissue region, a medical instrument region where the medical instrument exists, and a non-biological tissue region, and acquires the second data; and a synthesis data output unit that outputs synthesis data in which the first data and the second data are synthesized.

Note C4

The information processing device according to Note C3, in which the synthesis data output unit includes a first synthesis data output unit that outputs, of the first data and the second data, first synthesis data in which data regarding a biological tissue-related region classified into the biological tissue region and the non-biological tissue region is synthesized, and a second synthesis data output unit that outputs, of the first data and the second data, second synthesis data in which data regarding the medical instrument region is synthesized.

Note C5

The information processing device according to Note C4, in which the second synthesis data output unit outputs the second synthesis data using data regarding the medical instrument region included in the first data in a case where the position information can be acquired from the medical instrument trained model, and outputs the second synthesis data using data regarding the medical instrument region included in the second data in a case where the position information cannot be acquired from the medical instrument trained model.

Note C6

The information processing device according to Note C4, in which the synthesis data output unit outputs the second synthesis data in which data regarding the medical instrument region is synthesized on the basis of weighting according to the reliability of the first data and the reliability of the second data.

Note C7

The information processing device according to Note C6, in which the reliability is determined on the basis of whether or not the position information has been acquired from the medical instrument trained model.

Note C8

The information processing device according to Note C6, in which the synthesis data output unit sets the reliability of the first data higher than the reliability of the second data in a case where the position information can be acquired from the medical instrument trained model, and sets the reliability of the first data lower than the reliability of the second data in a case where the position information cannot be acquired from the medical instrument trained model.

Note C9

The information processing device according to any one of Notes C1 to C8, in which the image acquisition catheter is a three-dimensional scanning catheter that sequentially acquires the plurality of catheter images along a long direction of the image acquisition catheter.

Note C10

An information processing method for causing a computer to execute processing of acquiring a catheter image including an inner cavity obtained by an image acquisition catheter, acquiring position information regarding a position of a medical instrument inserted into the inner cavity included in the catheter image, and inputting the acquired catheter image and acquired position information to a first trained model that, upon receiving input of the catheter image and the position information regarding the position of the medical instrument included in the catheter image, outputs first data in which each region of the catheter image is classified into at least three of a biological tissue region, a medical instrument region in which the medical instrument exists, and a non-biological tissue region, and outputting the first data.

Note C11

A non-transitory computer-readable medium storing a program, which when executed by a computer, performs processing comprising: acquiring a catheter image including an inner cavity obtained by an image acquisition catheter, acquiring position information regarding a position of a medical instrument inserted into the inner cavity included in the catheter image, and inputting the acquired catheter image and acquired position information to a first trained model that, upon receiving input of the catheter image and the position information regarding the position of the medical instrument included in the catheter image, outputs first data in which each region of the catheter image is classified into at least three of a biological tissue region, a medical instrument region in which the medical instrument exists, and a non-biological tissue region, and outputting the first data.

The technical features (components) described in the embodiments can be combined with one another, and new technical features can be formed by combination.

The detailed description above describes embodiments of an information processing device, an information processing method, and a program. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An information processing device comprising:

an image acquisition unit configured to acquire a catheter image including an inner cavity obtained by an image acquisition catheter;

a position information acquisition unit configured to acquire position information regarding a position of a medical instrument inserted into the inner cavity included in the catheter image;

a first data output unit configured to input the acquired catheter image and the acquired position information to a first trained model that, upon receiving input of the catheter image and the position information, outputs first data in which each region of the catheter image is classified into at least three of a biological tissue region, a medical instrument region where the medical instrument exists, and a non-biological tissue region, and to output the first data; and wherein the catheter image comprises an RT-format image in which a plurality of scanning line data acquired from a radial scanning type image acquisition catheter are arranged in parallel in order of a scanning angle, and the first data is a classification result of each pixel in the RT format image, and wherein the first trained model includes a plurality of convolution layers, and at least one of the plurality of convolution layers is trained by performing padding processing of adding same data as that on a side with a large scanning angle to an outer side of a side with a small scanning angle and adding same data as that on a side with a small scanning angle to an outer side of a side with a large scanning angle.

2. The information processing device according to claim 1, wherein the position information acquisition unit is configured to:

input the acquired catheter image into a medical instrument trained model that, upon receiving input of the catheter image and calculating probability that the medical instrument is visualized for each pixel on the catheter image, as the position information, (i) outputs a position of the pixel having a highest probability in the catheter image, (ii) outputs a position of a center of gravity of a region of pixels in the catheter image where the probability exceeds a predetermined threshold, or (iii) outputs a region in which the probability exceeds a predetermined threshold; and acquire the position information from the medical instrument trained model.

3. The information processing device according to claim 2, further comprising:

a second data acquisition unit that is configured to input the RT format image to a second model that, upon receiving input of the RT image without receiving input of the position information, outputs, as a classification result of each pixel in the RT format, second data in which each region of the catheter image is classified into at least three of a biological tissue region, a medical instrument region where the medical instrument exists, and a non-biological tissue region, and to acquire the second data; and a synthesis data output unit that is configured to output synthesis data in which the first data and the second data are synthesized.

4. The information processing device according to claim 3, wherein the synthesis data output unit includes:

a first synthesis data output unit that is configured to output, of the first data and the second data, first synthesis data in which data regarding a biological tissue-related region classified into the biological tissue region and the non-biological tissue region is synthesized; and a second synthesis data output unit that is configured to output, of the first data and the second data, second synthesis data in which data regarding the medical instrument region is synthesized.

5. The information processing device according to claim 4, wherein the second synthesis data output unit is configured to:

output the second synthesis data using data regarding the medical instrument region included in the first data in a case where the position information can be acquired from the medical instrument trained model; and output the second synthesis data using data regarding the medical instrument region included in the second data in a case where the position information cannot be acquired from the medical instrument trained model.

6. The information processing device according to claim 4, wherein the synthesis data output unit is configured to output the second synthesis data in which data regarding the medical instrument region is synthesized on a basis of weighting according to a reliability of the first data and a reliability of the second data.

7. The information processing device according to claim 1, wherein the image acquisition catheter is a three-dimensional scanning catheter that sequentially acquires the plurality of catheter images along a long direction of the image acquisition catheter.

8. The information processing device according to claim 1, wherein the first trained model includes a memory portion that holds information regarding the catheter image input in past, and outputs the first classification data on a basis of information held in the memory portion and the latest catheter image among the plurality of catheter images.

9. The information processing device according to claim 1, further comprising:

a three-dimensional output unit that outputs a three-dimensional image generated on a basis of a plurality of pieces of the first classification data generated from the plurality of respective acquired catheter images.

10. An information processing method for causing a computer to execute a process comprising:

acquiring a catheter image including an inner cavity obtained by an image acquisition catheter;

acquiring position information regarding a position of a medical instrument inserted into the inner cavity included in the catheter image;

inputting the acquired catheter image and acquired position information to a first trained model that, upon receiving input of the catheter image and the position information regarding the position of the medical instrument included in the catheter image, outputs first data in which each region of the catheter image is classified into at least three of a biological tissue region, a medical instrument region in which the medical instrument exists, and a non-biological tissue region, and outputting the first data; and wherein the catheter image comprises an RT-format image in which a plurality of scanning line data acquired from a radial scanning type image acquisition catheter are arranged in parallel in order of a scanning angle, and the first data is a classification result of each pixel in the RT format image, and wherein the first trained model includes a plurality of convolution layers, and at least one of the plurality of convolution layers is trained by performing padding processing of adding same data as that on a side with a large scanning angle to an outer side of a side with a small scanning angle and adding same data as that on a side with a small scanning angle to an outer side of a side with a large scanning angle.

11. The information processing method according to claim 10, further comprising:

inputting the acquired catheter image into a medical instrument trained model that, upon receiving input of the catheter image and calculating probability that the medical instrument is visualized for each pixel on the catheter image, as the position information, (i) outputs a position of the pixel having a highest probability in the catheter image, (ii) outputs a position of a center of gravity of a region of pixels in the catheter image where the probability exceeds a predetermined threshold, or (iii) outputs a region in which the probability exceeds a predetermined threshold; and acquiring the position information from the medical instrument trained model.

12. The information processing method according to claim 11, further comprising:

inputting the RT format image to a second model that, upon receiving input of the RT image without receiving input of the position information, outputs, as a classification result of each pixel in the RT format image, second data in which each region of the catheter image is classified into at least three of a biological tissue region, a medical instrument region where the medical instrument exists, and a non-biological tissue region, and acquiring the second data; and outputting synthesis data in which the first data and the second data are synthesized.

13. The information processing method according to claim 12, further comprising:

outputting, of the first data and the second data, first synthesis data in which data regarding a biological tissue-related region classified into the biological tissue region and the non-biological tissue region is synthesized; and outputting, of the first data and the second data, second synthesis data in which data regarding the medical instrument region is synthesized.

14. The information processing method according to claim 13, further comprising:

outputting the second synthesis data using data regarding the medical instrument region included in the first data in a case where the position information can be acquired from the medical instrument trained model; and outputting the second synthesis data using data regarding the medical instrument region included in the second data in a case where the position information cannot be acquired from the medical instrument trained model.

15. The information processing method according to claim 13, further comprising:

outputting the second synthesis data in which data regarding the medical instrument region is synthesized on a basis of weighting according to a reliability of the first data and a reliability of the second data.

16. The information processing method according to claim 10, wherein the image acquisition catheter is a three-dimensional scanning catheter that sequentially acquires the plurality of catheter images along a long direction of the image acquisition catheter.

17. The information processing method according to claim 10, wherein the first trained model includes a memory portion that holds information regarding the catheter image input in past, and outputs the first classification data on a basis of information held in the memory portion and the latest catheter image among the plurality of catheter images.

18. The information processing method according to claim 10, further comprising:

outputting a three-dimensional image generated on a basis of a plurality of pieces of the first classification data generated from the plurality of respective acquired catheter images.

19. A non-transitory computer-readable medium storing a program, which when executed by a computer, performs processing comprising:

acquiring a catheter image including an inner cavity obtained by an image acquisition catheter;

acquiring position information regarding a position of a medical instrument inserted into the inner cavity included in the catheter image;

inputting the acquired catheter image and acquired position information to a first trained model that, upon receiving input of the catheter image and the position information regarding the position of the medical instrument included in the catheter image, outputs first data in which each region of the catheter image is classified into at least three of a biological tissue region, a medical instrument region in which the medical instrument exists, and a non-biological tissue region, and outputting the first data; and wherein the catheter image comprises an RT-format image in which a plurality of scanning line data acquired from a radial scanning type image acquisition catheter are arranged in parallel in order of a scanning angle, and the first data is a classification result of each pixel in the RT format image, and wherein the first trained model includes a plurality of convolution layers, and at least one of the plurality of convolution layers is trained by performing padding processing of adding same data as that on a side with a large scanning angle to an outer side of a side with a small scanning angle and adding same data as that on a side with a small scanning angle to an outer side of a side with a large scanning angle.

20. The non-transitory computer-readable medium according to claim 19, further comprising:

inputting the acquired catheter image into a medical instrument trained model that, upon receiving input of the catheter image and calculating probability that the medical instrument is visualized for each pixel on the catheter image, as the position information, (i) outputs a position of the pixel having a highest probability in the catheter image, (ii) outputs a position of a center of gravity of a region of pixels in the catheter image where the probability exceeds a predetermined threshold, or (iii) outputs a region in which the probability exceeds a predetermined threshold; and acquiring the position information from the medical instrument trained model.

* * * * *